(12) United States Patent
Varadachari

(10) Patent No.: US 8,999,031 B2
(45) Date of Patent: Apr. 7, 2015

(54) POLYPHOSPHATE FERTILIZER COMBINATIONS

(75) Inventor: Chandrika Varadachari, West Bengal (IN)

(73) Assignee: Agtec Innovations, Inc., Los Altos, CA (US)

(*) Notice: Subject to any disclaimer, the term of this patent is extended or adjusted under 35 U.S.C. 154(b) by 0 days.

(21) Appl. No.: 13/816,089

(22) PCT Filed: Aug. 8, 2011

(86) PCT No.: PCT/IN2011/000519
§ 371 (c)(1),
(2), (4) Date: Feb. 11, 2013

(87) PCT Pub. No.: WO2012/020427
PCT Pub. Date: Feb. 16, 2012

(65) Prior Publication Data
US 2013/0143737 A1 Jun. 6, 2013

Related U.S. Application Data

(60) Provisional application No. 61/390,574, filed on Oct. 6, 2010.

(30) Foreign Application Priority Data

Aug. 10, 2010 (IN) .............................. 886/KOL/2010

(51) Int. Cl.
| C05B 17/00 | (2006.01) |
|---|---|
| C05B 13/06 | (2006.01) |
| C05B 17/02 | (2006.01) |
| C05D 9/02 | (2006.01) |

(52) U.S. Cl.
CPC .................. *C05B 17/00* (2013.01); *C05B 13/06* (2013.01); *C05B 17/02* (2013.01)

(58) Field of Classification Search
CPC ...... C01B 25/301; C01B 25/412; C05B 7/00; C05B 9/00; C05B 13/06; C05B 17/02; C05C 9/00; C05G 3/0047; A01N 25/26; A01N 59/26
USPC .......... 71/29, 33, 44, 48, 49, 41, 51; 423/305, 423/306, 352; 504/101; 47/57.6
See application file for complete search history.

(56) References Cited

U.S. PATENT DOCUMENTS

| 2,713,536 | A | 1/1955 | Driskell |
|---|---|---|---|
| 3,201,222 | A | 8/1965 | Wilson |
| 3,208,821 | A | 9/1965 | Lehr et al. |
| 3,244,500 | A | 4/1966 | Stinson et al. |
| 3,453,074 | A | 7/1969 | Mustian et al. |
| 3,533,737 | A | 10/1970 | Farr et al. |
| 3,574,591 | A | 4/1971 | Lyons et al. |
| 3,656,931 | A | 4/1972 | Dancy |
| 3,762,909 | A | 10/1973 | Davie et al. |
| 3,856,500 | A | 12/1974 | Cox |
| 3,956,464 | A | 5/1976 | Drechsel et al. |
| 4,321,078 | A | 3/1982 | Michaud |
| 4,585,751 | A | 4/1986 | Kukes et al. |
| 5,433,766 | A | 7/1995 | Ming et al. |
| 5,749,935 | A | 5/1998 | Takehara et al. |
| 6,322,607 | B1 | 11/2001 | Brown et al. |
| 6,575,155 | B2 | 6/2003 | Brennan |
| 7,497,891 | B2 | 3/2009 | Peacock |
| 7,670,405 | B2 | 3/2010 | Varadachari |
| 7,691,171 | B2 | 4/2010 | Varadachari |
| 7,850,758 | B2 * | 12/2010 | Birthisel et al. ............... 71/64.1 |
| 8,216,337 | B2 * | 7/2012 | Varadachari ....................... 71/42 |
| 8,506,670 | B2 * | 8/2013 | Varadachari ....................... 71/21 |
| 2006/0260372 | A1 | 11/2006 | Liu et al. |
| 2007/0062232 | A1 | 3/2007 | Urano et al. |
| 2008/0236033 | A1 | 10/2008 | Sun et al. |
| 2010/0240533 | A1 * | 9/2010 | Varadachari .................. 504/101 |
| 2013/0133387 | A1 * | 5/2013 | Varadachari ....................... 71/48 |

FOREIGN PATENT DOCUMENTS

| CN | 1467182 | | 1/2004 | |
|---|---|---|---|---|
| CN | 1467182 | A * | 1/2004 | .............. C05G 1/00 |
| EP | 2393381 | | 12/2011 | |
| GB | 800417 | A | 8/1958 | |
| IN | 172800 | A | 4/1993 | |
| IN | 175597 | A | 7/1995 | |
| IN | 177205 | A | 7/1996 | |
| IN | 194747 | A | 12/2010 | |
| SU | 1270148 | A | 11/1986 | |

(Continued)

OTHER PUBLICATIONS

Bhattacharya et al., "Development of a Novel Slow-Releasing Iron-Manganese Fertilizer Compound," 2007, Ind. Eng. Chem. Res., 46:2870-2876.*
Bandyopadhyay et al., A New Slow-Releasing Molybdenum Fertilizer, Journal of Agricultural & Food Chemistry, 2008, 56: 1343-1349.
Bhattacharya et al., Development of a Novel Slow-Releasing Iron-Manganese Fertilizer Compound, Ind. Eng. Chem. Res., 2007, 46: 2870-2876.
Chandra et al., A New Slow-Releasing Iron Fertilizer, Chemical Eng. Journal, 2009, 155: 451-456.
Mortvedt et al., Macronutrients in Agriculture, Soil Science Society of America, 1972, 356-365.
Ray et al., Novel Slow-Releasing Micronutrient Fertilizers 2, Journal of Agriculture & Food Chemistry, 1997, 1447-1453.
Ray et al., Novel Slow-Releasing Micronutrient Fertilizers, American Chemical Society, 1993, 32: 1218-1227.

(Continued)

*Primary Examiner* — Jane C Oswecki
(74) *Attorney, Agent, or Firm* — Bryan Cave LLP

(57) ABSTRACT

A composite particle and a population of particles comprising a water-insoluble polyphosphate composition, methods of producing, and methods of using the same are provided. The polyphosphate composition may comprise at least one alkaline earth metal selected from calcium and magnesium and optionally at least one nutrient ion selected from the group consisting of potassium, ammonium, zinc, iron, manganese, copper, boron, chlorine, iodine, molybdenum, selenium or sulfur.

50 Claims, No Drawings

(56) References Cited

FOREIGN PATENT DOCUMENTS

| WO | 81/00010 | | 1/1981 | | |
|---|---|---|---|---|---|
| WO | 94/26660 | | 11/1994 | | |
| WO | 2005/014505 | A1 | 2/2005 | | |
| WO | 2005/014506 | A2 | 2/2005 | | |
| WO | WO2005/014506 | A2 * | 2/2005 | ............... | C05G 3/00 |
| WO | 2006/137084 | A2 | 12/2006 | | |
| WO | 2007/095393 | A2 | 8/2007 | | |
| WO | 2008/069676 | A2 | 6/2008 | | |
| WO | 2008/083390 | A2 | 7/2008 | | |
| WO | 2008/131535 | A1 | 11/2008 | | |
| WO | 2010089766 | | 8/2010 | | |
| WO | 2010089776 | A1 | 8/2010 | | |
| WO | 2012/020428 | A1 | 2/2012 | | |

OTHER PUBLICATIONS

Ray et al., Removing Micronutrient Metal Cation Interferences Prior to Titrimetric Determination of Polyphosphate Chain Length, Journal of Agriculture & Food Chemistry, 1998, 46: 2222-2226.

Roberts, G.J., FeO—K2O—P2O5 Glasses as a Source of Micronutrient Iron in Soil, Amer. Ceramic Society Bulletin, 1975, 54: 1069.

Roberts, G.J., Preparation and Properties of Glasses in the System FeO—K2O—P2O5, Amer. Ceramic Society Bulletin, 1973, 52: 383.

Varadachari et al., Bio-Release Multinutrient Fertilizers for High-Altitude Agriculture; Mountain Research & Development (Switzerland), 2009, 29(3): 241-249.

Varadachari, Phosphoric Acids, Phosphates and Fertilizers for the Future, Indian Nat. Sci. Academy Proceedings (Part B), 1992, 58: 119-126.

Varadachari, Novel Slow-Releasing Micronutrient Fertilizers, Fertilizer News, 1992, 37: 49-53.

Varadachari et al., Polyphosphates: The Future of Fertilizer Development, Everyman's Science, 1993, 28: 64-66.

Varadachari et al., Phosphoric Acid Polymerization and its Role in Fertilizer Development, Indian Fertilizer Scene Annual, 1992, 125-126.

International Search Report for PCT/IN2011/000519, dated Jan. 4, 2012, 4 pages.

International Search Report for PCT/IN2010/000062, dated Jun. 24, 2010, 6 pages.

Database WPI Week and SU 833927 Al, May 30, 1981 abstract, Thomson Scientific, London, Great Britian.

Volfkovich, S. I. Polymeric Fertilizers, J. Appl. Chem. (USSR) 1972, 45.2479-2487.

International Search Report for PCT/IN2011/000520, dated Dec. 28, 2011, 4 pages.

Ray et al., Novel Slow-releasing micronutrient fertilizers. 1. Zinc compounds, Ind. Eng. Chem. Res., 1993, 32: 1218-1227.

* cited by examiner

POLYPHOSPHATE FERTILIZER COMBINATIONS

FIELD OF THE INVENTION

The present invention generally relates to fertilizers and, in particular, to composites comprising a polyphosphate fertilizer composition.

BACKGROUND OF THE INVENTION

Phosphates are macronutrients generally thought to be essential building blocks for plants and animals. Plant fertilization with phosphates, alone or in combination with nitrogen and potash fertilization, generally results in better crop yields and more nutritious food.

Prior phosphate fertilizers include diammonium phosphate (DAP), monoammonium phosphate (MAP), triple super phosphate (TSP) and others. These water-soluble compounds, however, tend to leach from the soil, leading some to apply an amount that is several times the actual crop uptake, leading to poor efficiency and the contamination of water bodies.

SUMMARY OF THE INVENTION

Among the various aspects of the present invention is the provision of populations of particles comprising a water-insoluble, dilute acid-soluble polyphosphate composition having a defined size, the provision of composite particles comprising a water-insoluble, dilute acid-soluble polyphosphate composition and at least one chemically distinct composition, the provision of fertilizer compositions comprising such populations and/or composites, and the provision of polyphosphate fertilizers optionally containing at least one nutrient ion selected from the group consisting of potassium, sodium, ammonium, boron, chromium, cobalt, copper, iodine, iron, manganese, molybdenum, selenium, sulfur and zinc.

Briefly, the present invention is directed to a composite particle having a size greater than 80 mesh BS, the particle comprising a water-insoluble, dilute acid-soluble polyphosphate composition.

Briefly, the present invention is directed to a composite particle having a size greater than 0.2 mm, the particle comprising a water-insoluble, dilute acid-soluble polyphosphate composition.

Briefly, the present invention is directed to a composite particle having a size greater than 0.25 mm, the particle comprising a water-insoluble, dilute acid-soluble polyphosphate composition.

The present invention is further directed to a composite particle having a size greater than 0.2 mm, the particle comprising a water-insoluble, dilute acid-soluble inorganic polyphosphate composition in solid form, the inorganic polyphosphate composition containing 5 to 70 wt % orthophosphate, and optionally one or more micronutrient metals selected from the group consisting of chromium, cobalt, copper, iron, manganese, and zinc. The inorganic polyphosphate polymer has a number average chain length of greater than 2 and less than 50 repeat units when the orthophosphate content of the inorganic polyphosphate polymer is excluded from the average chain length calculation and a number average chain length of at least 1.1 but less than 50 repeat units when the orthophosphate content of the inorganic polyphosphate polymer is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a composite particle having a size greater than 0.2 mm, the particle comprising a water-insoluble, dilute acid-soluble inorganic polyphosphate composition in solid form, the inorganic polyphosphate composition containing ammonium, calcium, magnesium, sodium or potassium or a combination thereof, 5 to 70 wt % orthophosphate, and optionally one or more micronutrient metals selected from the group consisting of chromium, cobalt, copper, iron, manganese, and zinc. The inorganic polyphosphate polymer composition has a number average chain length of greater than 2 and less than 50 repeat units when the orthophosphate content of the inorganic polyphosphate polymer composition is excluded from the average chain length calculation and a number average chain length of at least 1.1 but less than 50 repeat units when the orthophosphate content of the inorganic polyphosphate polymer composition is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a population of particles having an average size of greater than 80 mesh BS, the particles comprising a water-insoluble, dilute acid-soluble polyphosphate composition.

The present invention is further directed to a population of particles having an average size of greater than 80 mesh BS, the particles comprising a water-insoluble, dilute acid-soluble inorganic polyphosphate composition in solid form, the inorganic polyphosphate composition containing 5 to 70 wt % orthophosphate, and optionally one or more micronutrient metals selected from the group consisting of chromium, cobalt, copper, iron, manganese, and zinc. The inorganic polyphosphate polymer has a number average chain length of greater than 2 and less than 50 repeat units when the orthophosphate content of the inorganic polyphosphate polymer is excluded from the average chain length calculation and a number average chain length of at least 1.1 but less than 50 repeat units when the orthophosphate content of the inorganic polyphosphate polymer is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a population of particles having an average size of greater than 80 mesh BS, the particles comprising a water-insoluble, dilute acid-soluble inorganic polyphosphate composition in solid form, the inorganic polyphosphate composition containing ammonium, calcium, magnesium, sodium or potassium or a combination thereof, 5 to 70 wt % orthophosphate, and optionally one or more micronutrient metals selected from the group consisting of chromium, cobalt, copper, iron, manganese, and zinc. The inorganic polyphosphate polymer composition has a number average chain length of greater than 2 and less than 50 repeat units when the orthophosphate content of the inorganic polyphosphate polymer composition is excluded from the average chain length calculation and a number average chain length of at least 1.1 but less than 50 repeat units when the orthophosphate content of the inorganic polyphosphate polymer composition is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a population of particles having an average size of at least 0.25 mm, the particles comprising a water-insoluble, dilute acid-soluble polyphosphate composition.

The present invention is further directed to a population of particles having an average size of at least 0.2 mm, the particles comprising a water-insoluble, dilute acid-soluble inorganic polyphosphate composition in solid form, the inorganic polyphosphate composition containing 5 to 70 wt % orthophosphate, and optionally one or more micronutrient metals selected from the group consisting of chromium, cobalt, copper, iron, manganese, and zinc. The inorganic polyphosphate polymer has a number average chain length of greater than 2 and less than 50 repeat units when the orthophosphate content of the inorganic polyphosphate polymer is excluded from the average chain length calculation and a number average chain length of at least 1.1 but less than 50 repeat units when the orthophosphate content of the inorganic polyphosphate polymer is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a population of particles having an average size of at least 0.2 mm, the particles comprising a water-insoluble, dilute acid-soluble inorganic polyphosphate composition in solid form, the inorganic polyphosphate composition containing ammonium, calcium, magnesium, sodium or potassium or a combination thereof, 5 to 70 wt % orthophosphate, and optionally one or more micronutrient metals selected from the group consisting of chromium, cobalt, copper, iron, manganese, and zinc. The inorganic polyphosphate polymer composition has a number average chain length of greater than 2 and less than 50 repeat units when the orthophosphate content of the inorganic polyphosphate polymer composition is excluded from the average chain length calculation and a number average chain length of at least 1.1 but less than 50 repeat units when the orthophosphate content of the inorganic polyphosphate polymer composition is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a population of particles having an average size of greater than 80 mesh BS, the particles comprising at least 0.01 wt. % of a water-insoluble, dilute acid-soluble polyphosphate composition.

The present invention is further directed to a population of particles having an average size of greater than 80 mesh BS, the particles comprising at least 0.01 wt. % of a water-insoluble, dilute acid-soluble inorganic polyphosphate composition in solid form, the inorganic polyphosphate composition containing 5 to 70 wt % orthophosphate, and optionally one or more micronutrient metals selected from the group consisting of chromium, cobalt, copper, iron, manganese, and zinc. The inorganic polyphosphate polymer has a number average chain length of greater than 2 and less than 50 repeat units when the orthophosphate content of the inorganic polyphosphate polymer is excluded from the average chain length calculation and a number average chain length of at least 1.1 but less than 50 repeat units when the orthophosphate content of the inorganic polyphosphate polymer is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a population of particles having an average size of greater than 80 mesh BS, the particles comprising at least 0.01 wt. % of a water-insoluble, dilute acid-soluble inorganic polyphosphate composition in solid form, the inorganic polyphosphate composition containing ammonium, calcium, magnesium, sodium or potassium or a combination thereof, 5 to 70 wt % orthophosphate, and optionally one or more micronutrient metals selected from the group consisting of chromium, cobalt, copper, iron, manganese, and zinc. The inorganic polyphosphate polymer composition has a number average chain length of greater than 2 and less than 50 repeat units when the orthophosphate content of the inorganic polyphosphate polymer composition is excluded from the average chain length calculation and a number average chain length of at least 1.1 but less than 50 repeat units when the orthophosphate content of the inorganic polyphosphate polymer composition is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a population of particles having an average size of at least 0.25 mm, the particles comprising at least 0.01 wt. % of a water-insoluble, dilute acid-soluble polyphosphate composition.

The present invention is further directed to a population of particles having an average size of at least 0.2 mm, the particles comprising at least 0.01 wt. % of a water-insoluble, dilute acid-soluble inorganic polyphosphate composition in solid form, the inorganic polyphosphate composition containing 5 to 70 wt % orthophosphate, and optionally one or more micronutrient metals selected from the group consisting of chromium, cobalt, copper, iron, manganese, and zinc. The inorganic polyphosphate polymer has a number average chain length of greater than 2 and less than 50 repeat units when the orthophosphate content of the inorganic polyphosphate polymer is excluded from the average chain length calculation and a number average chain length of at least 1.1 but less than 50 repeat units when the orthophosphate content of the inorganic polyphosphate polymer is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

The present invention is further directed to a population of particles having an average size of at least 0.2 mm, the particles comprising at least 0.01 wt. % of a water-insoluble, dilute acid-soluble inorganic polyphosphate composition in solid form, the inorganic polyphosphate composition containing ammonium, calcium, magnesium, sodium or potassium or a combination thereof, 5 to 70 wt % orthophosphate, and optionally one or more micronutrient metals selected from the group consisting of chromium, cobalt, copper, iron, manganese, and zinc. The inorganic polyphosphate polymer composition has a number average chain length of greater than 2 and less than 50 repeat units when the orthophosphate content of the inorganic polyphosphate polymer composition is excluded from the average chain length calculation and a number average chain length of at least 1.1 but less than 50 repeat units when the orthophosphate content of the inorganic polyphosphate polymer composition is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1.

Another aspect of the present invention is a population of particles having an average size of at least 0.2 mm comprising an inorganic polyphosphate composition in solid form, characterized by having an X-ray diffraction reflection at one or more of the following positions: 5.96 (±0.03), 5.37 (±0.03), 5.01 (±0.025), 4.73, 4.61, 4.5, 4.15, 4.04, 3.7, 3.66(±0.01), 3.58(±0.01), 3.47(±0.01), 3.39(±0.01), 3.35(±0.01), 3.19(±0.01), 3.13(±0.01), 3.09(±0.01), 3.05(±0.01), 2.96(±0.009), 2.94(±0.009), 2.82(±0.009), 2.76(±0.008), 2.73(±0.008), 2.59(±0.007), 2.53(±0.007), 2.5(±0.007), 2.43 (±0.007), 2.41(±0.007), 2.37(±0.007), 2.34(±0.006), 2.25(±0.006), 2.2(±0.006), 2.18(±0.005), 2.16(±0.005), 2.14 (±0.005), 2.12(±0.005), 2.09(±0.005), 2.08(±0.005), 2.03(±0.005), 1.99(±0.004), 1.93(±0.004), 1.91(±0.004), 1.85(±0.003), 1.8(±0.003), 1.76(±0.003), 1.72(±0.003), 1.68 (±0.0028), 1.64(±0.0027), 1.59(±0.0025), 1.57(±0.0024) Å.

Another aspect of the present invention is a population of particles having an average size of at least 0.2 mm comprising an inorganic polyphosphate composition in solid form, characterized by having an X-ray diffraction reflection at one or more of the following positions: 7.54(±0.03), 6.74(±0.03), 5.96 (±0.03), 5.37 (±0.03), 5.01 (±0.025), 4.73, 4.61, 4.5, 4.15, 4.04, 3.7, 3.66(±0.01), 3.58(±0.01), 3.47(±0.01), 3.39 (±0.01), 3.35(±0.01), 3.19(±0.01), 3.13(±0.01), 3.09(±0.01), 3.05(±0.01), 2.96(±0.009), 2.94(±0.009), 2.82(±0.009), 2.76 (±0.008), 2.73(±0.008), 2.59(±0.007), 2.53(±0.007), 2.5(±0.007), 2.43(±0.007), 2.41(±0.007), 2.37(±0.007), 2.34 (±0.006), 2.25(±0.006), 2.2(±0.006), 2.18(±0.005), 2.16(±0.005), 2.14(±0.005), 2.12(±0.005), 2.09(±0.005), 2.08(±0.005), 2.03(±0.005), 1.99(±0.004), 1.93(±0.004), 1.91(±0.004), 1.85(±0.003), 1.8(±0.003), 1.76(±0.003), 1.72 (±0.003), 1.68(±0.0028), 1.64(±0.0027), 1.59(±0.0025), 1.57 (±0.0024) Å.

Another aspect of the present invention is a population of particles comprising an inorganic polyphosphate containing at least 5 wt. % calcium, magnesium, sodium, potassium or ammonium, in combination, and optionally, one or more nutrients selected from boron, chromium, cobalt, copper, iodine, iron, manganese, molybdenum, selenium, and zinc, the inorganic polyphosphate composition having a solubility in room-temperature (25° C.) deionized water such that the combined amount of ammonium, calcium, chromium, cobalt, copper, iron, magnesium, manganese, potassium, selenium, sodium, and zinc that dissolves from the inorganic polyphosphate composition during a 30 minute period in deionized water at room-temperature (25° C.) is less than 20% of the combined amount of ammonium, calcium, chromium, cobalt, copper, iron, magnesium, manganese, potassium, selenium, sodium, and zinc that dissolves from the inorganic polyphosphate composition during a 30 minute period in 0.1N HCl at room-temperature (25° C.).

Another aspect of the present invention is a population of particles comprising an inorganic polyphosphate containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in room-temperature (25° C.) dilute citric acid such that the combined amount of ammonium, calcium, chromium, cobalt, copper, iron, magnesium, manganese, potassium, selenium, sodium, and zinc that dissolves from the inorganic polyphosphate composition during a 20 minute period in citric acid having a citric acid concentration not in excess of 6.9 wt. % citric acid at room-temperature (25° C.) is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1N HCl at room-temperature (25° C.).

Another aspect of the present invention is a population of particles comprising an inorganic polyphosphate containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in room-temperature (25° C.) dilute citric acid such that the combined amount of ammonium, calcium, chromium, cobalt, copper, iron, magnesium, manganese, potassium, selenium, sodium, and zinc that dissolves from the inorganic polyphosphate composition during a 20 minute period in citric acid having a citric acid concentration not in excess of 2 wt. % citric acid at room-temperature (25° C.) is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1N HCl at room-temperature (25° C.).

Another aspect of the present invention is a population of particles comprising an inorganic polyphosphate containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in room-temperature (25° C.) dilute citric acid such that the combined amount of ammonium, calcium, chromium, cobalt, copper, iron, magnesium, manganese, potassium, selenium, sodium, and zinc that dissolves from the inorganic polyphosphate composition during a 20 minute period in citric acid having a citric acid concentration not in excess of 0.1 wt. % citric acid at room-temperature (25° C.) is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1 N HCl at room-temperature (25° C.).

Another aspect of the present invention is a population of particles comprising an inorganic polyphosphate containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in room-temperature (25° C.) dilute ethylenediaminetetraacetic acid (EDTA) such that the combined amount of ammonium, calcium, chromium, cobalt, copper, iron, magnesium, manganese, potassium, selenium, sodium, and zinc that dissolves from the inorganic polyphosphate composition during a 20 minute period in 0.005M EDTA at room-temperature (25° C.) is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1N HCl at room-temperature (25° C.).

Another aspect of the present invention is a population of particles comprising an inorganic polyphosphate containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in room-temperature (25° C.) dilute diethylenetriaminepentaacetic acid (DTPA) such that the combined amount of ammonium, calcium, chromium, cobalt, copper, iron, magnesium, manganese, potassium, selenium, sodium, and zinc that dissolves from the inorganic polyphosphate composition during a 20 minute period in 0.005M DTPA at room-temperature (25° C.) is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1N HCl at room-temperature (25° C.).

Another aspect of the present invention is a population of particles comprising an inorganic polyphosphate containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in room-temperature (25° C.) dilute hydrochloric acid such that the combined amount of ammonium, calcium, chromium, cobalt, copper, iron, magnesium, manganese, potassium, selenium, sodium, and zinc that dissolves from the inorganic polyphosphate composition during a 20 minute period in 0.01 N HCl at room-temperature (25° C.) is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1N HCl at room-temperature (25° C.).

Another aspect of the present invention is a population of particles comprising an inorganic polyphosphate containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in room-temperature (25° C.) dilute citric acid, dilute ethylenediaminetetraacetic acid (EDTA), dilute diethylenetriaminepentaacetic acid (DTPA) and dilute hydrochloric acid such that the combined amount of ammonium, calcium, chromium, cobalt, copper, iron, magnesium, manganese, potassium, selenium, sodium, and zinc that dissolves from the inorganic polyphosphate composition during a 20 minute period in each of 0.1 wt. % citric acid, 0.005M EDTA and 0.01 N HCl at room-temperature (25° C.) is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1N HCl at room-temperature (25° C.).

DETAILED DESCRIPTION OF THE PREFERRED EMBODIMENTS

The present invention is generally directed to populations of particles having a defined size and comprising a water-insoluble, dilute acid-soluble polyphosphate composition and to composite particles comprising a water-insoluble, dilute acid-soluble polyphosphate composition and at least one chemically distinct composition. In one embodiment, the population of particles comprises the composite particles. In another embodiment, the population of particles comprises particles of a water-insoluble, dilute acid-soluble polyphosphate composition, optionally containing micronutrients. Thus, for example, the water-insoluble, dilute acid-soluble polyphosphate may be an alkaline earth metal polyphosphate (as described in greater detail elsewhere herein) containing micronutrient amounts of a micronutrient selected from the group consisting of boron, chromium, cobalt, copper, iodine, iron, manganese, molybdenum, selenium, sulfur, zinc and combinations thereof or a polyphosphate composition (as described elsewhere herein) optionally containing such micronutrients. In one embodiment, the water-insoluble, dilute acid-soluble polyphosphate contains at least 5 wt. % alkali metal, alkaline earth metal, ammonium, or a combination thereof. In one embodiment, the water-insoluble, dilute acid-soluble polyphosphate contains at least 5 wt. % of calcium, magnesium, sodium, potassium or ammonium, in combination, In general, the composite particles contain a water-insoluble, dilute acid-soluble polyphosphate composition and a chemically distinct composition. Within the composite particle, the chemically distinct compositions may reside in discrete layers. For example, the water-insoluble, dilute acid-soluble polyphosphate composition may reside in a layer overlying the chemically distinct composition or in a layer underlying the chemically distinct composition. By way of further example, the composite particles may comprise a core having a first composition, and an outer layer over the core of a second, distinct composition; in this embodiment, the water-insoluble, dilute acid-soluble polyphosphate composition may reside in the core and the chemically distinct composition resides in the outer layer or vice versa. Alternatively, the water-insoluble, dilute acid-soluble polyphosphate composition and the chemically distinct composition are combined in the particles without being segregated into discrete layers; for example, the water-insoluble, dilute acid-soluble polyphosphate composition and the chemically distinct composition may be combined by co-granulation or other technique to form particles having discontinuous regions of discrete composition.

In general, populations of particles of the present invention comprising a water-insoluble, dilute acid-soluble polyphosphate composition have an average size of greater than 80 mesh BS. For example, in one embodiment, the population of particles has a size greater than 60 mesh BS. By way of further example, in one embodiment the population of particles has an average size greater than 30 mesh BS. By way of further example, in one embodiment the population of particles has an average size 16 mesh BS. By way of further example, in one embodiment the population of particles has an average size greater than 10 mesh BS. By way of further example, in one embodiment the population of particles has an average size greater than 8 mesh BS. By way of further example, in one embodiment the population of particles has an average size greater than 7 mesh BS. By way of further example, in one embodiment the population of particles has an average size greater than 6 mesh BS. By way of further example, in one embodiment the population of particles has an average size greater than 5 mesh BS. In each of the foregoing embodiments, the population may comprise composite particles of the present invention, it may comprise particles of the water-insoluble, dilute acid-soluble polyphosphate composition, per se, i.e., particles consisting of a water-insoluble, dilute acid-soluble polyphosphate composition, or a combination comprising the composite particles and the water-insoluble, dilute acid-soluble polyphosphate composition, per se.

In one embodiment, particles within the population of particles of the present invention comprise a water-insoluble, dilute acid-soluble polyphosphate composition and have a size of at least 0.2 mm (i.e., at least one dimension of the particles is greater than 0.2 mm). For example, in one embodiment, the particles within the population have a size of at least 0.25 mm. By way of further example, in one embodiment the particles within the population have a size of at least 0.35 mm. By way of further example, in one embodiment the particles within the population have a size of at least 0.5 mm. By way of further example, in one embodiment the particles within the population have a size of at least 0.75 mm. By way of further example, in one embodiment the particles within the population have a size of at least 1 mm. By way of further example, in one embodiment the particles within the population have a size of at least 1.5 mm. By way of further example, in one embodiment the particles within the population have a size of at least 1.75 mm. By way of further example, in one embodiment the particles within the population have a size of at least 2 mm. By way of further example, in one embodiment the particles within the population have a size of at least 2.5 mm. By way of further example, in one embodiment the particles within the population have a size of at least 2.75 mm. By way of further example, in one embodiment the particles within the population have a size of at least 3 mm. By way of further example, in one embodiment the particles within the population have a size of at least 3.25 mm.

In general, the composite particles have a size of greater than 80 mesh BS. For example, in one embodiment, the particles have a size greater than 60 mesh BS. By way of further example, in one embodiment the particles have a size greater than 30 mesh BS. By way of further example, in one embodiment the particles have a size greater than 16 mesh BS. By way of further example, in one embodiment the particles have a size greater than 10 mesh BS. By way of further example, in one embodiment the particles have a size greater than 8 mesh BS. By way of further example, in one embodiment the particles have a size greater than 7 mesh BS. By way of further example, in one embodiment the particles have a size greater than 6 mesh BS. By way of further example, in one embodiment the particles have a size greater than 5 mesh BS.

The composite particles may be combined to form a population (or mass) of free-flowing particles having an average particle size greater than 80 mesh. For example, in one embodiment, the population of particles has an average particle size greater than 60 mesh BS. By way of further example, in one embodiment the population of particles has an average particle size greater than 30 mesh BS. By way of further example, in one embodiment the population of particles has an average particle size greater than 16 mesh BS. By way of further example, in one embodiment the population of particles has an average particle size greater than 10 mesh BS. By way of further example, in one embodiment the population of particles has an average particle size greater than 8 mesh BS. By way of further example, in one embodiment the population of particles has an average particle size greater than 7 mesh BS. By way of further example, in one embodiment the population of particles has an average particle size greater than 6 mesh BS. By way of further example, in one embodiment the population of particles has an average particle size greater than 5 mesh BS.

In one embodiment, the composite particles have a size of at least 0.2 mm (i.e., at least one dimension of the particles is greater than 0.2 mm). For example, in one embodiment, the composite particles may have a size of at least 0.25 mm. By way of further example, in one embodiment the composite particles have a size of at least 0.35 mm. By way of further example, in one embodiment the composite particles have a size of at least 0.5 mm. By way of further example, in one embodiment the composite particles have a size of at least 0.75 mm. By way of further example, in one embodiment the composite particles have a size of at least 1 mm. By way of further example, in one embodiment the composite particles have a size of at least 1.5 mm. By way of further example, in one embodiment the composite particles have a size of at least 1.75 mm. By way of further example, in one embodiment the composite particles have a size of at least 2 mm. By way of further example, in one embodiment the composite particles have a size of at least 2.5 mm. By way of further example, in one embodiment the composite particles have a size of at least 2.75 mm. By way of further example, in one embodiment the composite particles have a size of at least 3 mm. By way of further example, in one embodiment the composite particles have a size of at least 3.25 mm.

In one embodiment, the composite particles are combined to form a population of particles having an average size of at least 0.2 mm (i.e., at least one dimension of the particles is greater than 0.2 mm). For example, in one embodiment, the population of particles may have an average size of at least 0.25 mm. By way of further example, in one embodiment the population of particles has an average size of at least 0.35 mm. By way of further example, in one embodiment the population of particles has an average size of at least 0.5 mm. By way of further example, in one embodiment the population of particles has an average size of at least 0.75 mm. By way of further example, in one embodiment the population of particles has an average size of at least 1 mm. By way of further example, in one embodiment the population of particles has an average size of at least 1.5 mm. By way of further example, in one embodiment the population of particles has an average size of at least 1.75 mm. By way of further example, in one embodiment the population of particles has an average size of at least 2 mm. By way of further example, in one embodiment the population of particles has an average size of at least 2.5 mm. By way of further example, in one embodiment the population of particles has an average size of at least 2.75 mm. By way of further example, in one embodiment the population of particles has an average size of at least 3 mm. By way of further example, in one embodiment the population of particles has an average size of at least 3.25 mm.

In general, populations of particles of the present invention comprise at least about 0.01% by weight of a polyphosphate polymer composition described herein. For example, in one embodiment the population comprises at least 0.05 wt. % of the polyphosphate composition. By way of further example, in one embodiment the population comprises at least 0.1 wt. % of the polyphosphate composition. By way of further example, in one embodiment the population comprises at least 0.25 wt. % of the polyphosphate composition. By way of further example, in one embodiment the population comprises at least 0.5 wt. % of the polyphosphate composition. By way of further example, in one embodiment the population comprises at least 0.75 wt. % of the polyphosphate composition. By way of further example, in one embodiment the population comprises at least 1 wt. % of the polyphosphate composition. Typically, however, the population comprises will comprise less than 99 wt. % of the polyphosphate composition. For example, in some embodiments, the population comprises less than 90 wt. % of the polyphosphate composition. For example, in some embodiments, the population comprises less than 80 wt. % of the polyphosphate composition. For example, in some embodiments, the population comprises less than 70 wt. % of the polyphosphate composition. For example, in some embodiments, the population comprises less than 60 wt. % of the polyphosphate composition. By way of further example, in some embodiments the population comprises less than 50 wt. % of the polyphosphate composition. By way of further example, in some embodiments the population comprises less than 40 wt. % of the polyphosphate composition. By way of further example, in some embodiments the population comprises less than 30 wt. % of the polyphosphate composition. By way of further example, in some embodiments the population comprises less than 20 wt. % of the polyphosphate composition. In certain embodiments, therefore, the population comprises about 0.01 to about 99 wt. % of the polyphosphate composition. In certain embodiments, the population comprises about 0.01 to about 75 wt. % of the polyphosphate composition. In certain embodiments, the population comprises about 0.01 to about 50 wt. % of the polyphosphate composition. In certain embodiments, the population comprises about 0.1 to about 99 wt. % of the polyphosphate composition. In certain embodiments, the population comprises about 0.1 to about 75 wt. % of the polyphosphate composition. In certain embodiments, the population comprises about 0.1 to about 50 wt. % of the polyphosphate composition. In certain embodiments, the population comprises about 1 to about 99 wt. % of the polyphosphate composition. In certain embodiments, the population comprises about 1 to about 95 wt. % of the polyphosphate composition. In certain embodiments, therefore, the population comprises about 1 to about 75 wt. % of the polyphosphate composition. In certain embodiments, therefore, the population comprises about 1 to about 99 wt. % of the polyphosphate composition. In certain embodiments, therefore, the population comprises about 0.5 to about 20 wt. % of the polyphosphate composition. In certain embodiments, therefore, the population comprises about 0.5 to about 15 wt. % of the polyphosphate composition. In certain embodiments, therefore, the population comprises about 0.5 to about 10 wt. % of the polyphosphate composition.

In general, the composite particles comprise at least about 0.01% by weight of a polyphosphate polymer composition described herein. For example, in one embodiment the composite particles comprise at least 0.05 wt. % of a polyphosphate composition. By way of further example, in one embodiment the composite particles comprise at least 0.1 wt. % of a polyphosphate composition. By way of further example, in one embodiment the composite particles comprise at least 0.25 wt. % of a polyphosphate composition. By way of further example, in one embodiment the composite particles comprise at least 0.5 wt. % of a polyphosphate composition. By way of further example, in one embodiment the composite particles comprise at least 0.75 wt. % of a polyphosphate composition. By way of further example, in one embodiment the composite particles comprise at least 1 wt. % of a polyphosphate composition. Typically, however, the composite particles will comprise less than 99 wt. % of a polyphosphate composition. For example, in some embodiments, the composite particles comprise less than 90 wt. % of a polyphosphate composition. For example, in some embodiments, the composite particles comprise less than 80 wt. % of a polyphosphate composition. For example, in some embodiments, the composite particles comprise less than 70 wt. % of a polyphosphate composition. For example, in some embodiments, the composite particles comprise less than 60 wt. % of a polyphosphate composition. By way of further example, in some embodiments the composite particles comprise less than 50 wt. % of a polyphosphate composition. By way of further example, in some embodiments the composite particles comprise less than 40 wt. % of a polyphosphate composition. By way of further example, in some embodiments the composite particles comprise less than 30 wt. % of a polyphosphate composition. By way of further example, in some embodiments the composite particles comprise less than 20 wt. % of a polyphosphate composition. In certain embodiments, therefore, the composite particles comprise about 0.01 to about 99 wt. % of a polyphosphate composition. In certain embodiments, the composite particles comprise about 0.01 to about 75 wt. % of a polyphosphate composition. In certain embodiments, the composite particles comprise about 0.01 to about 50 wt. % of a polyphosphate composition. In certain embodiments, the composite particles comprise about 0.1 to about 99 wt. % of a polyphosphate composition. In certain embodiments, the composite particles comprise about 0.1 to about 75 wt. % of a polyphosphate composition. In certain embodiments, the composite particles comprise about 0.1 to about 50 wt. % of a polyphosphate composition. In certain embodiments, the composite particles comprise about 1 to about 99 wt. % of a polyphosphate composition. In certain embodiments, the composite particles comprise about 1 to about 95 wt. % of a polyphosphate composition. In certain embodiments, therefore, the composite particles comprise about 1 to about 75 wt. % of a polyphosphate composition. In certain embodiments, therefore, the composite particles comprise about 1 to about 99 wt. % of a polyphosphate composition. In certain embodiments, therefore, the composite particles comprise about 0.5 to about 20 wt. % of a polyphosphate composition. In certain embodiments, therefore, the composite particles comprise about 0.5 to about 15 wt. % of a polyphosphate composition. In certain embodiments, therefore, the composite particles comprise about 0.5 to about 10 wt. % of a polyphosphate composition.

In addition to the polyphosphate composition described herein, the composite particles may comprise a nitrogen-source, a phosphorous source, a potassium-source, a secondary or micronutrient source. Exemplary nitrogen sources include urea, ammonium sulfate and derivatives thereof. Exemplary phosphorus sources include single superphosphates, triple superphosphates, calcium phosphates, nitrophosphates, potassium phosphates, ammonium phosphates, ammoniated superphosphates and the like and mixtures thereof. Exemplary potassium sources include muriate of potash, potassium sulfates, potassium phosphates, potassium hydroxides, potassium nitrates, potassium carbonates and bicarbonates, potassium magnesium sulfates and the like and mixtures thereof. Suitable secondary nutrient sources for use herein include elemental sulfur, calcium and magnesium salts such as phosphates, oxides, sulfates, carbonates, chlorides, nitrates and the like and mixtures thereof. Suitable micronutrient sources include iron, manganese, copper, boron, zinc and molybdenum salts such as phosphates, oxides, sulfates, carbonates, chlorides, nitrates, borates, molybdates and the like and mixtures thereof as well as chelates of micronutrients such as EDTA chelates and the like. For example, the following representative materials may be used as micronutrient sources in the present invention: calcium nitrate, magnesium sulfate, magnesium nitrate, ferrous sulfate, ferrous nitrate, manganese sulfate, manganese nitrate, copper sulfate, copper nitrate, boric acid, sodium borate, zinc sulfate, zinc nitrate, sodium molybdate, ammonium molybdate and the like. For example, in such embodiments, the composite particles may also comprise in addition to the nitrogen, phosphorous, potassium, secondary or micronutrient source about 0.01 to about 75 wt. % of a polyphosphate composition. By way of further example, in such embodiments, the composite particles may also comprise in addition to the nitrogen, phosphorous, potassium, secondary or micronutrient source about 0.01 to about 50 wt. % of a polyphosphate composition. By way of further example, in such embodiments, the composite particles may also comprise in addition to the nitrogen, phosphorous, potassium, secondary or micronutrient source about 0.01 to about 25 wt. % of a polyphosphate composition. By way of further example, in such embodiments, the composite particles may also comprise in addition to the nitrogen, phosphorous, potassium, secondary or micronutrient source about 0.1 to about 25 wt. % of a polyphosphate composition. By way of further example, in such embodiments, the composite particles may also comprise in addition to the nitrogen, phosphorous, potassium, secondary or micronutrient source about 0.5 to about 25 wt. % of a polyphosphate composition. By way of further example, in such embodiments, the composite particles may also comprise in addition to the nitrogen, phosphorous, potassium, secondary or micronutrient source about 0.5 to about 10 wt. % of a polyphosphate composition.

In another embodiment, the composite particles comprise a pesticide. The pesticide may be, for example, a herbicide, insecticide, fungicide, or combination thereof. Non-limiting examples of pesticides include 2-4D, parathion, malation, and s-triazines. For example, in such embodiments, the composite particles may also comprise in addition to the pesticide about 0.01 to about 75 wt. % of a polyphosphate composition described herein. By way of further example, in such embodiments, the composite particles may also comprise in addition to the pesticide about 0.01 to about 50 wt. % of a polyphosphate composition. By way of further example, in such embodiments, the composite particles may also comprise in addition to the pesticide about 0.01 to about 25 wt. % of a polyphosphate composition. By way of further example, in such embodiments, the composite particles may also comprise in addition to the pesticide about 0.1 to about 25 wt. % of a polyphosphate composition. By way of further example, in such embodiments, the composite particles may also comprise in addition to the pesticide about 0.5 to about 25 wt. % of a polyphosphate composition. By way of further example, in such embodiments, the composite particles may also comprise in addition to the pesticide about 0.5 to about 10 wt. % of a polyphosphate composition.

In one embodiment, the composite particles contain agrichemicals such as manure, gypsum, dolomite, and plant growth hormones. For example, in such embodiments, the composite particles may also comprise in addition to the agrichemicals about 0.01 to about 95 wt. % of a polyphosphate composition described herein. By way of further example, in such embodiments, the composite particles may also comprise in addition to the agrichemicals about 20 to about 95 wt. % of a polyphosphate composition. By way of further example, in such embodiments, the composite particles may also comprise in addition to the agrichemicals about 40 to about 95 wt. % of a polyphosphate composition. By way of further example, in such embodiments, the composite particles may also comprise in addition to the agrichemicals about 50 to about 95 wt. % of a polyphosphate composition. By way of further example, in such embodiments, the composite particles may also comprise in addition to the agrichemicals about 60 to about 95 wt. % of a polyphosphate composition. By way of further example, in such embodiments, the composite particles may also comprise in addition to the agrichemicals about 60 to about 95 wt. % of a polyphosphate composition.

In one embodiment, the composite particles contain granules of a macronutrient fertilizer, granules of china clay, bentonite, attapulgite, organic wastes, agricultural wastes having a size greater than 0.5 mm. In one embodiment, such particles have a size greater than 1 mm. In another embodiment, such particles have a size greater than 2 mm. In another embodiment, such particles have a size greater than 3 mm. Additionally, in such embodiments, the composite particles may also comprise about 10 to about 95 wt. % of a polyphosphate composition described herein. By way of further example, in such embodiments, the composite particles may also comprise about 30 to about 95 wt. % of a polyphosphate composition. By way of further example, in such embodiments, the composite particles may also comprise about 40 to about 95 wt. % of a polyphosphate composition. By way of further example, in such embodiments, the composite particles may also comprise about 50 to about 95 wt. % of a polyphosphate composition. By way of further example, in such embodiments, the composite particles may also comprise about 60 to about 95 wt. % of a polyphosphate composition. By way of further example, in such embodiments, the composite particles may also comprise about 60 to about 95 wt. % of a polyphosphate composition.

In one embodiment, the composite particles comprise plant seeds. For example, the composite particles may comprise soybean, corn, rice or wheat seeds. Alternatively, the composite particles may comprise seeds of a plant other than soybean, corn, rice and wheat. Regardless of the type of seed, in such embodiments, the composite particles may also comprise in addition to one or more seeds about 0.01 to about 75 wt. % of a polyphosphate composition described herein. By way of further example, in such embodiments, the composite particles may also comprise in addition to one or more seeds about 0.01 to about 50 wt. % of a polyphosphate composition. By way of further example, in such embodiments, the composite particles may also comprise in addition to one or more seeds about 0.01 to about 25 wt. % of a polyphosphate composition. By way of further example, in such embodiments, the composite particles may also comprise in addition to one or more seeds about 0.1 to about 25 wt. % of a polyphosphate composition. By way of further example, in such embodiments, the composite particles may also comprise in addition to one or more seeds about 0.5 to about 25 wt. % of a polyphosphate composition. By way of further example, in such embodiments, the composite particles may also comprise in addition to one or more seeds about 0.5 to about 10 wt. % of a polyphosphate composition.

In another embodiment, the composite particles comprise $Al_2O_3$, $ZnO$, an iron oxide, $MnO_2$, $FeTiO_3$, $MgAl_2O_4$, $(ZnFeMn)(FeMn)_2O_4$, quarry fines, a dredge material, kaolin, glass, foundry sand, red mud, silica fines, coal fines, mine tailings, bauxite, recycled concrete, recovered drywall, brucite, manganite, gibbsite, diaspare, bachmite, goethite, carnallite, boracite, epsomite, newberryite, magnasite, olivine, dolomite, metal slag, calcium-containing dredge containing an oxide and/or carbonate of calcium, agricultural fiber, ocean sand, ash, collected particles from metal processes involving combustion, a waste metal slurry, a metal slurry, a metal shaving, graphite, or recycled asphalt. Regardless of the type of material, in such embodiments, the composite particles may also comprise in addition to one or more of above materials, about 0.01 to about 95 wt. % of a polyphosphate composition described herein. By way of further example, in such embodiments, the composite particles may also comprise about 10 to about 95 wt. % of a polyphosphate composition. By way of further example, in such embodiments, the composite particles may also comprise about 30 to about 95 wt. % of a polyphosphate composition. By way of further example, in such embodiments, the composite particles may also comprise about 40 to about 95 wt. % of a polyphosphate composition. By way of further example, in such embodiments, the composite particles may also comprise about 50 to about 95 wt. % of a polyphosphate composition. By way of further example, in such embodiments, the composite particles may also comprise about 60 to about 95 wt. % of a polyphosphate composition. By way of further example, in such embodiments, the composite particles may also comprise about 0.5 to about 10 wt. % of a polyphosphate composition.

In a preferred embodiment, the composite particles are formed by combining a mass of a polyphosphate composition described herein having an average size of less than 80 mesh BS with a mass of particles having an average particle size greater than 80 mesh BS and mixing until a layer of the polyphosphate composition is formed on the surface of the mass of larger particles or the polyphosphate particles adhere to the surface of the larger particles. For example, in one embodiment a mass of polyphosphate particles having an average particle size less than 80 mesh BS are adhered to the surface of particles having an average particle greater than 80 mesh. Without wishing to be bound by any particular theory, and based upon experimental evidence obtained to-date, it appears that this occurs as a result of electrostatic attraction of opposite charges or difference in acidity between the surfaces of the smaller polyphosphate and the larger particles. To exploit this, the polyphosphates may be synthesized to facilitate this adsorption by adjusting the pH of the polyphosphate during synthesis. For example, if a polyphosphate is to be adsorbed to the surface of a particle that is alkaline, such as urea (which has an alkaline surface), the polyphosphate preferably has a pH of less than 5, preferably in the range of pH 4 to 5 (the pH may be controlled, for example, by controlling the extent of neutralization during synthesis of the polyphosphate). If, however, the polyphosphate is to be adsorbed to the surface of a particle that is acidic, such as monoammonium phosphate (MAP) (which has an acidic surface), the polyphosphate preferably has a pH of at least 5, preferably in the range of pH 5 to 7. Using such techniques, the amount of polyphosphate adsorbed to the surface of the larger particle be 80 wt % or even more of the mass of the larger particle. For example, in one embodiment, a mass of polyphosphate particles having an average particle size of less than 150 mesh is mixed with a mass of particles having an average particle size greater than 0.5 mm until a layer of the polyphosphate composition is formed on the mass of larger particles. By way of further example, in one embodiment, a mass of polyphosphate particles having an average particle size of less than 150 mesh is mixed with a mass of particles having an average particle size greater than 1.5 mm until a layer of the polyphosphate composition is formed on the mass of larger particles. By way of further example, in one embodiment, a mass of polyphosphate particles having an average particle size of less than 150 mesh is mixed with a mass of particles having an average particle size greater than 2 mm until a layer of the polyphosphate composition is formed on the mass of larger particles. By way of further example, in one embodiment, a mass of polyphosphate particles having an average particle size of less than 150 mesh is mixed with a mass of particles having an average particle size greater than 3 mm until a layer of the polyphosphate composition is formed on the mass of larger particles.

In one exemplary embodiment, the composite particles are formed by combining a mass of a polyphosphate composition described herein having an average size of less than 80 mesh BS with a mass of particles having an average particle size greater than 80 mesh BS, mixing, moistening the mixture with water and drying until a layer of the polyphosphate composition is formed on the surface of the mass of larger particles. For example, in one embodiment, a mass of polyphosphate particles having an average particle size of less than 150 mesh is mixed with a mass of particles such as monoammonium phosphate, diammonium phosphate, triple super phosphate, single superphosphate, or combinations thereof, having an average particle size greater than 0.5 mm, moistened with water and dried until a layer of the polyphosphate composition is formed on the mass of larger particles. In another embodiment, a mass of polyphosphate particles having an average particle size of less than 150 mesh is mixed with a mass of particles having an average particle size greater than 1 mm, moistened with water and dried until a layer of the polyphosphate composition is formed on the mass of larger particles. In another embodiment, a mass of polyphosphate particles having an average particle size of less than 150 mesh is mixed with a mass of particles having an average particle size greater than 2 mm, moistened with water and dried until a layer of the polyphosphate composition is formed on the mass of larger particles. In another embodiment, a mass of polyphosphate particles having an average particle size of less than 150 mesh is mixed with a mass of particles having an average particle size greater than 3 mm, moistened with water and dried until a layer of the polyphosphate composition is formed on the mass of larger particles.

In one exemplary embodiment, a population of particles having an average size of greater than 80 mesh is formed by granulating smaller particles of the polyphosphate composition (i.e., having a size of less than 80 mesh) with or without a binder. For example, in one embodiment, a mass of polyphosphate particles having an average particle size of less than 80 mesh, is mixed with water, granulated in a granulator and dried until an average particle size greater than 0.25 mm is formed. Alternatively, granulation is done with the suspension of the polyphosphate after its synthesis and prior to it being dried. To enable granulation without the use of a binder, the polyphosphate has a pH below 5 and preferably in the range of pH 4 to 5. Inclusion of ammonium ion in the polyphosphate (by the use of ammonia during neutralization) improves granule strength.

In an alternative embodiment, the composite particles are formed by co-granulating the polyphosphate composition described herein with any of the other materials disclosed herein using conventional granulation techniques. In this embodiment, the polyphosphate composition may function as a binder. For example, in one such embodiment, the composite particles are formed by combining a mass of a polyphosphate composition described herein having an average size of less than 80 mesh BS with a mass of particles having an average particle size either less than 80 mesh BS or greater than 80 mesh BS or both (such as muriate of potash fines, urea, or any of the other chemically distinct materials described herein for combination with the polyphosphate composition), mixing, moistening the mixture with water, granulating in a granulator and drying until a composite mass of larger particles is formed. Typically, binding is enhanced when the polyphosphate has a pH below 5 and when ammonium is incorporated in the polyphosphate. Without wishing to be bound to any particular theory and based upon experimental evidence obtained to-date, it appears that ammonium improves hydrogen bonding between the particles and thereby improves adhesive strength.

In each of the granulation methods described herein, conventional binders may be included in the granulation step to enhance the binding of the polyphosphate particles to other particles. Exemplary binders include bentonite, starch, cellulose and its derivatives, polyvinyl acetates, polyvinyl acetate copolymers, polyvinyl alcohols, polyvinyl alcohol copolymers, celluloses, including ethylcelluloses and methylcelluloses, hydroxymethyl celluloses, hydroxypropylcelluloses, hydroxymethylpropyl-celluloses, polyvinylpyrolidones, dextrins, malto-dextrins, polysaccharides, fats, oils, proteins, gum arabics, shellacs, vinylidene chloride, vinylidene chloride copolymers, calcium lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene and syrups or mixtures thereof. Other suitable binders include polymers and copolymers of vinyl acetate, methyl cellulose, vinylidene chloride, acrylic, cellulose, polyvinylpyrrolidone and polysaccharide. Still other suitable binders include polymers and copolymers of vinylidene chloride and vinyl acetate-ethylene copolymers. Conventional granulation techniques are followed.

Polyphosphate Compositions

The composite particles and populations of composite particles described herein comprise water-insoluble, dilute acid-soluble inorganic polyphosphate compositions. In general, the polyphosphate composition comprises ammonium, calcium, magnesium, sodium, potassium or a combination thereof and, optionally, at least one micronutrient (also sometimes referred to herein as nutrients or nutrient ions) selected from among ammonium, boron, chromium, cobalt, copper, iodine, iron, manganese, molybdenum, potassium, selenium, sodium, sulfur, zinc, and combinations thereof. For example, in one embodiment the polyphosphate composition comprises calcium, magnesium or a combination thereof and, optionally, at least one micronutrient (also sometimes referred to herein as nutrients or nutrient ions) selected from among ammonium, boron, chromium, cobalt, copper, iodine, iron, manganese, molybdenum, potassium, selenium, sodium, sulfur, zinc, and combinations thereof.

In general, the inorganic polyphosphate compositions are relatively short-chain polyphosphates produced by incomplete polymerization of orthophosphates. Typically, therefore, the inorganic polyphosphate will contain at least about 5 wt. % orthophosphate. Although the inorganic polyphosphate may contain as much as 70 wt. % orthophosphate, it is generally preferred that the inorganic polyphosphate comprise substantially less. Thus, for example, in one embodiment the inorganic polyphosphate may contain 5 to 50 wt. % orthophosphate. By way of further example, in one embodiment the inorganic polyphosphate may contain 7.5 to 50 wt. % orthophosphate. By way of further example, in one embodiment the inorganic polyphosphate may contain 10 to 45 wt. % orthophosphate. By way of further example, in some embodiments, the inorganic polyphosphate may contain 7.5 to 30 wt. % orthophosphate. By way of further example, in some embodiments, the inorganic polyphosphate may contain 10 to 30 wt. % orthophosphate. By way of further example, in some embodiments, the inorganic polyphosphate may contain 15 to 30 wt. % orthophosphate. By way of further example, in some embodiments, the inorganic polyphosphate may contain 10 to 25 wt. % orthophosphate. By way of further example, in some embodiments, the inorganic polyphosphate may contain 15 to 25 wt. % orthophosphate.

The inorganic polyphosphate compositions contain phosphate repeat units and may optionally also contain sulfate, borate, molybdate or selenate repeat units, or a combination thereof. Typically, the ratio of phosphate repeat units to the combined total of sulfate, borate, molybdate and selenate repeat units in the inorganic polyphosphate composition is at least 2:1 (phosphate:sulfate+borate+molybdate+selenate). For example, in certain embodiments, the ratio of phosphate repeat units to the combined total of sulfate, borate, molybdate and selenate repeat units in the inorganic polyphosphate composition is at least 2.5:1. By way of further example, in some embodiments the ratio of phosphate repeat units to the combined total of sulfate, borate, molybdate and selenate repeat units in the inorganic polyphosphate composition is at least 3:1. By way of further example, in some embodiments the ratio of phosphate repeat units to the combined total of sulfate, borate, molybdate and selenate repeat units in the inorganic polyphosphate composition will be between 2:1 and 5:1. By way of further example, in some embodiments the ratio of phosphate repeat units to the combined total of sulfate, borate, molybdate and selenate repeat units in the inorganic polyphosphate composition will be between 2:1 and 10:1. By way of further example, in some embodiments the ratio of phosphate repeat units to the sulfate repeat units in the inorganic polyphosphate composition will be between 2:1 and 5:1. By way of further example, in some embodiments the ratio of phosphate repeat units to the sulfate repeat units in the inorganic polyphosphate composition will be between 2:1 and 10:1.

Depending upon the extent of polymerization, the inorganic polyphosphates may have a range of chain lengths. When the calculation is based upon total phosphate content (i.e., including the orthophosphate content of the polyphosphate), the average chain length (number average) may be in the range of about 1.1 to 50 repeat units (phosphate, sulfate, borate, molybdate and/or selenate repeat units) per chain. For example, in one embodiment the average chain length (number average) may be 1.2 to 50 repeat units (phosphate, sulfate, borate, molybdate and/or selenate repeat units) per chain based upon total phosphate content. By way of further example, in one embodiment the average chain length (number average) may be 1.2 to 25 repeat units (phosphate, sulfate, borate, molybdate and/or selenate repeat units) per chain based upon total phosphate content. By way of further example, in one embodiment the average chain length (number average) may be 1.2 to 20 repeat units (phosphate, sulfate, borate, molybdate and/or selenate repeat units) per chain based upon total phosphate content. By way of further example, in one embodiment the average chain length (number average) may be 1.2 to 15 repeat units (phosphate, sulfate, borate, molybdate and/or selenate repeat units) per chain based upon total phosphate content. By way of further example, in one embodiment the average chain length (number average) may be 2 to 20 repeat units (phosphate, sulfate, borate, molybdate and/or selenate repeat units) per chain based upon total phosphate content. By way of further example, in one embodiment the average chain length (number average) may be 2 to 15 repeat units (phosphate, sulfate, borate, molybdate and/or selenate repeat units) per chain based upon total phosphate content. By way of further example, in one embodiment the average chain length (number average) may be 2 to 10 repeat units (phosphate, sulfate, borate, molybdate and/or selenate repeat units) per chain based upon total phosphate content. By way of further example, in one embodiment the average chain length (number average) may be 2.5 to 15 repeat units (phosphate, sulfate, borate, molybdate and/or selenate repeat units) per chain based upon total phosphate content. By way of further example, in one embodiment the average chain length (number average) may be 2.5 to 10 repeat units (phosphate, sulfate, borate, molybdate and/or selenate repeat units) per chain based upon total phosphate content. By way of further example, in one embodiment the average chain length (number average) may be 3 to 15 repeat units (phosphate, sulfate, borate, molybdate and/or selenate repeat units) per chain based upon total phosphate content. By way of further example, in one embodiment the average chain length (number average) may be 3 to 10 repeat units (phosphate, sulfate, borate, molybdate and/or selenate repeat units) per chain based upon total phosphate content. By way of further example, in one embodiment the average chain length (number average) may be 1.2 to 5 repeat units (phosphate, sulfate, borate, molybdate and/or selenate repeat units) per chain based upon total phosphate content. By way of further example, in one embodiment the average chain length (number average) may be 1.3 to 4 repeat units (phosphate, sulfate, borate, molybdate and/or selenate repeat units) per chain based upon total phosphate content. By way of further example, in one embodiment the average chain length (number average) may be 1.3 to 2.9 repeat units (phosphate, sulfate, borate, molybdate and/or selenate repeat units) per chain based upon total phosphate content.

In certain embodiments, when the calculation is based upon total phosphate content (i.e., including the orthophosphate content of the polyphosphate), the average chain length (number average) may be in the range of about 1.2 and 50 phosphate units (phosphorus atoms) per chain. For example, in one embodiment the average chain length (number average) may be 1.2 to 25 phosphate units (phosphorus atoms) per chain based upon total phosphate content. By way of further example, in one embodiment the average chain length (number average) may be 1.2 to 20 phosphate units (phosphorus atoms) per chain based upon total phosphate content. By way of further example, in one embodiment the average chain length (number average) may be 1.2 to 15 phosphate units (phosphorus atoms) per chain based upon total phosphate content. By way of further example, in one embodiment the average chain length (number average) may be 2 to 20 phosphate units (phosphorus atoms) per chain based upon total phosphate content. By way of further example, in one embodiment the average chain length (number average) may be 2 to 15 phosphate units (phosphorus atoms) per chain based upon total phosphate content. By way of further example, in one embodiment the average chain length (number average) may be 2 to 10 phosphate units (phosphorus atoms) per chain based upon total phosphate content. By way of further example, in one embodiment the average chain length (number average) may be 2.5 to 15 phosphate units (phosphorus atoms) per chain based upon total phosphate content. By way of further example, in one embodiment the average chain length (number average) may be 2.5 to 10 phosphate units (phosphorus atoms) per chain based upon total phosphate content. By way of further example, in one embodiment the average chain length (number average) may be 3 to 15 phosphate units (phosphorus atoms) per chain based upon total phosphate content. By way of further example, in one embodiment the average chain length (number average) may be 3 to 10 phosphate units (phosphorus atoms) per chain based upon total phosphate content. By way of further example, in one embodiment the average chain length (number average) may be 1.1 to 5 phosphate units (phosphorus atoms) per chain based upon total phosphate content. By way of further example, in one embodiment the average chain length (number average) may be 1.2 to 5 phosphate units (phosphorus atoms) per chain based upon total phosphate content. By way of further example, in one embodiment the average chain length (number average) may be 1.3 to 4 phosphate units (phosphorus atoms) per chain based upon total phosphate content. By way of further example, in one embodiment the average chain length (number average) may be 1.3 to 2.9 phosphate units (phosphorus atoms) per chain based upon total phosphate content.

When the calculation is based upon the non-orthophosphate fraction of the polyphosphate, (i.e., excluding the orthophosphate fraction of the polyphosphate from the calculation), the average chain length (number average) may be in the range of about 2 and the average chain length (number average) may be in the range of about 1.2 and 50 repeat units (phosphate, sulfate, borate, molybdate and/or selenate repeat units) per chain based upon the non-orthophosphate fraction of the polyphosphate. For example, in one embodiment the average chain length (number average) may be 1.2 to 25 repeat units (phosphate, sulfate, borate, molybdate and/or selenate repeat units) per chain based upon the non-orthophosphate fraction of the polyphosphate. By way of further example, in one embodiment the average chain length (number average) may be 1.2 to 20 repeat units (phosphate, sulfate, borate, molybdate and/or selenate repeat units) per chain based upon the non-orthophosphate fraction of the polyphosphate. By way of further example, in one embodiment the average chain length (number average) may be 1.2 to 15 repeat units (phosphate, sulfate, borate, molybdate and/or selenate repeat units) per chain based upon the non-orthophosphate fraction of the polyphosphate. By way of further example, in one embodiment the average chain length (number average) may be 2 to 20 repeat units (phosphate, sulfate, borate, molybdate and/or selenate repeat units) per chain based upon the non-orthophosphate fraction of the polyphosphate. By way of further example, in one embodiment the average chain length (number average) may be 2 to 15 repeat units (phosphate, sulfate, borate, molybdate and/or selenate repeat units) per chain based upon the non-orthophosphate fraction of the polyphosphate. By way of further example, in one embodiment the average chain length (number average) may be 2 to 10 repeat units (phosphate, sulfate, borate, molybdate and/or selenate repeat units) per chain based upon the non-orthophosphate fraction of the polyphosphate. By way of further example, in one embodiment the average chain length (number average) may be 2.5 to 15 repeat units (phosphate, sulfate, borate, molybdate and/or selenate repeat units) per chain based upon the non-orthophosphate fraction of the polyphosphate. By way of further example, in one embodiment the average chain length (number average) may be 2.5 to 10 repeat units (phosphate, sulfate, borate, molybdate and/or selenate repeat units) per chain based upon the non-orthophosphate fraction of the polyphosphate. By way of further example, in one embodiment the average chain length (number average) may be 3 to 15 repeat units (phosphate, sulfate, borate, molybdate and/or selenate repeat units) per chain based upon the non-orthophosphate fraction of the polyphosphate. By way of further example, in one embodiment the average chain length (number average) may be 3 to 10 repeat units (phosphate, sulfate, borate, molybdate and/or selenate repeat units) per chain based upon the non-orthophosphate fraction of the polyphosphate. By way of further example, in one embodiment the average chain length (number average) may be 2.1 to 10 repeat units (phosphate, sulfate, borate, molybdate and/or selenate repeat units) per chain based upon the non-orthophosphate fraction of the polyphosphate. By way of further example, in one embodiment the average chain length (number average) may be 2.5 to 7 repeat units (phosphate, sulfate, borate, molybdate and/or selenate repeat units) per chain based upon the non-orthophosphate fraction of the polyphosphate. By way of further example, in one embodiment the average chain length (number average) may be 2.5 to 5 repeat units (phosphate, sulfate, borate, molybdate and/or selenate repeat units) per chain based upon the non-orthophosphate fraction of the polyphosphate.

In some embodiments in which the calculation is based upon the non-orthophosphate fraction of the polyphosphate, (i.e., excluding the orthophosphate fraction of the polyphosphate from the calculation), the average chain length (number average) may be in the range of about 2 and 50 phosphate units (phosphorus atoms) per chain. For example, in one embodiment the average chain length (number average) may be 2 to 25 phosphate units (phosphorus atoms) per chain based upon the non-orthophosphate fraction of the polyphosphate. By way of further example, in one embodiment the average chain length (number average) may be 2 to 20 phosphate units (phosphorus atoms) per chain based upon the non-orthophosphate fraction of the polyphosphate. By way of further example, in one embodiment the average chain length (number average) may be 2 to 15 phosphate units (phosphorus atoms) per chain based upon the non-orthophosphate fraction of the polyphosphate. By way of further example, in one embodiment the average chain length (number average) may be 2 to 10 phosphate units (phosphorus atoms) per chain based upon the non-orthophosphate fraction of the polyphosphate. By way of further example, in one embodiment the average chain length (number average) may be 2.5 to 20 phosphate units (phosphorus atoms) per chain based upon the non-orthophosphate fraction of the polyphosphate. By way of further example, in one embodiment the average chain length (number average) may be 2.5 to 15 phosphate units (phosphorus atoms) per chain based upon the non-orthophosphate fraction of the polyphosphate. By way of further example, in one embodiment the average chain length (number average) may be 2.5 to 10 phosphate units (phosphorus atoms) per chain based upon the non-orthophosphate fraction of the polyphosphate. By way of further example, in one embodiment the average chain length (number average) may be 3 to 20 phosphate units (phosphorus atoms) per chain based upon the non-orthophosphate fraction of the polyphosphate. By way of further example, in one embodiment the average chain length (number average) may be 3 to 15 phosphate units (phosphorus atoms) per chain based upon the non-orthophosphate fraction of the polyphosphate. By way of further example, in one embodiment the average chain length (number average) may be 3 to 10 phosphate units (phosphorus atoms) per chain based upon the non-orthophosphate fraction of the polyphosphate. By way of further example, in one embodiment the average chain length (number average) may be 3.5 to 20 phosphate units (phosphorus atoms) per chain based upon the non-orthophosphate fraction of the polyphosphate. By way of further example, in one embodiment the average chain length (number average) may be 3.5 to 15 phosphate units (phosphorus atoms) per chain based upon the non-orthophosphate fraction of the polyphosphate. By way of further example, in one embodiment the average chain length (number average) may be 3.5 to 10 phosphate units (phosphorus atoms) per chain based upon the non-orthophosphate fraction of the polyphosphate. By way of further example, in one embodiment the average chain length (number average) may be 4 to 20 phosphate units (phosphorus atoms) per chain based upon the non-orthophosphate fraction of the polyphosphate. By way of further example, in one embodiment the average chain length (number average) may be 4 to 15 phosphate units (phosphorus atoms) per chain based upon the non-orthophosphate fraction of the polyphosphate. By way of further example, in one embodiment the average chain length (number average) may be 4 to 10 phosphate units (phosphorus atoms) per chain based upon the non-orthophosphate fraction of the polyphosphate. By way of further example, in one embodiment the average chain length (number average) may be 4 to 9 phosphate units (phosphorus atoms) per chain based upon the non-orthophosphate fraction of the polyphosphate. By way of further example, in one embodiment the average chain length (number average) may be 4 to 8 phosphate units (phosphorus atoms) per chain based upon the non-orthophosphate fraction of the polyphosphate. By way of further example, in one embodiment the average chain length (number average) may be greater than 2 and less than 50 phosphate units (phosphorus atoms) per chain based upon the non-orthophosphate fraction of the polyphosphate. By way of further example, in one embodiment the average chain length (number average) may be 2.1 to 10 phosphate units (phosphorus atoms) per chain based upon the non-orthophosphate fraction of the polyphosphate. By way of further example, in one embodiment the average chain length (number average) may be 2.5 to 7 phosphate units (phosphorus atoms) per chain based upon the non-orthophosphate fraction of the polyphosphate. By way of further example, in one embodiment the average chain length (number average) may be 2.5 to 5 phosphate units (phosphorus atoms) per chain based upon the non-orthophosphate fraction of the polyphosphate.

On a molar basis, the polyphosphate composition also preferably contains at least 0.5 phosphate/sulfate/borate/molybdate/selenate repeat units (i.e., the combined total of phosphate, sulfate, borate, molybdate and selenate repeat units) for each atom of calcium and magnesium (in combination). In one exemplary embodiment, the polyphosphate composition contains at least 0.66 phosphate/sulfate/borate/molybdate/selenate repeat units (i.e., the combined total of phosphate, sulfate, borate, molybdate and selenate repeat units) for each atom of calcium and magnesium (in combination). By way of further example, in one embodiment, the polyphosphate composition contains at least 0.75 phosphate/sulfate/borate/molybdate/selenate repeat units for each atom of calcium and magnesium (in combination). By way of further example, in one embodiment, the polyphosphate composition contains at least 0.825 phosphate/sulfate/borate/molybdate/selenate repeat units for each atom of calcium and magnesium (in combination). By way of further example, in one embodiment, the polyphosphate composition contains at least 0.95 phosphate/sulfate/borate/molybdate/selenate repeat units for each atom of calcium and magnesium (in combination). By way of further example, in one embodiment, the polyphosphate composition contains no more than one alkaline earth metal atom selected from the group consisting of calcium, magnesium and a combination thereof for each phosphate/sulfate/borate/molybdate/selenate repeat units of the inorganic polyphosphate composition. By way of further example, in one embodiment, the polyphosphate composition contains at least 1.11 phosphate/sulfate/borate/molybdate/selenate repeat units for each atom of calcium and magnesium (in combination). By way of further example, in one embodiment, the polyphosphate composition may contain about 1.33 phosphate/sulfate/borate/molybdate/selenate repeat units for each atom of calcium and magnesium (in combination). By way of further example, in one embodiment, the polyphosphate composition may contain about 1.67 phosphate/sulfate/ borate/molybdate/selenate repeat units for each atom of calcium and magnesium (in combination). By way of further example, in one embodiment, the polyphosphate composition may contain about 2.22 phosphate/sulfate/borate/molybdate/selenate repeat units for each atom of calcium and magnesium (in combination). In general, however, the upper limit of the ratio of phosphate/sulfate/borate/molybdate/selenate repeat units to calcium and magnesium atoms is the ratio that would lead to the formation of the corresponding dihydrogen orthophosphate.

In one embodiment, on a molar basis, the polyphosphate composition preferably contains at least 0.5 phosphate repeat units for each atom of calcium and magnesium (in combination). In one exemplary embodiment, the polyphosphate composition contains at least 0.66 phosphate units (phosphorous atom) for each atom of calcium and magnesium (in combination). By way of further example, in one embodiment, the polyphosphate composition contains at least 0.75 phosphate units (phosphorous atom) for each atom of calcium and magnesium (in combination). By way of further example, in one embodiment, the polyphosphate composition contains at least 0.825 phosphate units (phosphorous atom) for each atom of calcium and magnesium (in combination). By way of further example, in one embodiment, the polyphosphate composition contains at least 0.95 phosphate units (phosphorous atom) for each atom of calcium and magnesium (in combination). By way of further example, in one embodiment, the polyphosphate composition contains no more than one alkaline earth metal atom selected from the group consisting of calcium, magnesium and a combination thereof for each phosphate unit (phosphorous atom) of the inorganic polyphosphate composition. In one exemplary embodiment, the polyphosphate composition contains By way of further example, in one embodiment, the polyphosphate composition contains at least 1.11 phosphate units (phosphorous atom) for each atom of calcium and magnesium (in combination). By way of further example, in one embodiment, the polyphosphate composition may contain about 1.33 phosphate units (phosphorous atoms) for each atom of calcium and magnesium (in combination). By way of further example, in one embodiment, the polyphosphate composition may contain about 1.67 phosphate units (phosphorous atoms) for each atom of calcium and magnesium (in combination). By way of further example, in one embodiment, the polyphosphate composition may contain about 2.22 phosphate units (phosphorous atoms) for each atom of calcium and magnesium (in combination). In general, however, the upper limit of the ratio of phosphate units (phosphorous atoms) to calcium and magnesium atoms is the ratio that would lead to the formation of the corresponding dihydrogen orthophosphate.

In general, it is preferred that inorganic polyphosphate composition contain calcium, magnesium, or a combination thereof, and that the inorganic polyphosphate have a ratio, A:Z, having a value of at least 0.3:1, wherein A is the combined number of equivalents of calcium and magnesium incorporated in the inorganic polyphosphate composition and Z is the combined number of equivalents of phosphate, sulfate, borate, molybdate, and selenate repeat units incorporated in the inorganic polyphosphate composition. In one exemplary embodiment, A:Z is at least 0.4:1. In another exemplary embodiment, A:Z is at least 0.45:1. In another exemplary embodiment, A:Z is at least 0.5:1. In another exemplary embodiment, A:Z is at least 0.52:1. In another exemplary embodiment, A:Z is at least 0.5:1. In another exemplary embodiment, A:Z is at least 0.5:1. In another exemplary embodiment, A:Z is at least 0.6:1. In another exemplary embodiment, A:Z is at least 0.5:1. In another exemplary embodiment, A:Z is at least 0.65:1. In another exemplary embodiment, A:Z is at least 0.7:1. In another exemplary embodiment, A:Z is at least 0.5:1. In another exemplary embodiment, A:Z is at least 0.8:1. In another exemplary embodiment, A:Z is at least 0.9:1. In general, however, A:Z will not exceed 1.25:1, with ratios in the range of about 0.5:1 to about 1:1 or even about 0.5:1 to about 0.75:1 being more typical. For example, in each of the foregoing embodiments, the inorganic polyphosphate composition may comprise phosphate repeat units and sulfate repeat units. By way of further example, in each of the foregoing embodiments, the inorganic polyphosphate composition may comprise phosphate repeat units and sulfate repeat units with the ratio of phosphate repeat units to sulfate repeat units being between 10:1 and 2:1.

In some embodiments, the ratio of the number of equivalents of calcium and magnesium, in combination, for each equivalent of phosphate in the polyphosphate composition is two-thirds of the value of the corresponding molar ratio. Stated differently, in one embodiment the inorganic polyphosphate composition contains calcium, magnesium, or a combination thereof, and that the inorganic polyphosphate have a ratio, A:P, having a value of at least 0.3:1, wherein A is the combined number of equivalents of calcium and magnesium incorporated in the inorganic polyphosphate composition and P is the number of equivalents of phosphorous, P, incorporated in the inorganic polyphosphate composition. In one exemplary embodiment, A:P is at least 0.4:1. In another exemplary embodiment, A:P is at least 0.45:1. In another exemplary embodiment, A:P is at least 0.5:1. In another exemplary embodiment, A:P is at least 0.52:1. In another exemplary embodiment, A:P is at least 0.5:1. In another exemplary embodiment, A:P is at least 0.5:1. In another exemplary embodiment, A:P is at least 0.6:1. In another exemplary embodiment, A:P is at least 0.5:1. In another exemplary embodiment, A:P is at least 0.65:1. In another exemplary embodiment, A:P is at least 0.7:1. In another exemplary embodiment, A:P is at least 0.5:1. In another exemplary embodiment, A:P is at least 0.8:1. In another exemplary embodiment, A:P is at least 0.9:1. In another exemplary embodiment, A:P has a value of 0.3:1 to 1:1. In general, however, A:P will not exceed 1:1, with ratios in the range of about 0.5:1 to about 0.75:1 being more typical.

Considered on a weight basis, in some embodiments the inorganic polyphosphate composition comprises at least 7 weight percent of an alkaline earth metal selected from calcium, magnesium and a combination thereof, based upon the total weight of the polyphosphate. Typically, however, the polyphosphate composition will contain less than about 35 weight percent of calcium and magnesium, in combination. For example, the polyphosphate composition may contain less than about 25 weight percent of calcium and magnesium, in combination. By way of further example, in one embodiment the polyphosphate composition comprises at least 7 wt. % calcium and no, or only trace amounts of magnesium. By way of further example, in this embodiment, the polyphosphate composition may contain at least 10 wt. % calcium and no, or only trace amounts of magnesium. By way of further example, in this embodiment, the polyphosphate composition may contain at least 12 wt. % calcium and no, or only trace amounts of magnesium. By way of further example, in this embodiment, the polyphosphate composition may contain at least 15 wt. % calcium and no, or only trace amounts of magnesium. By way of further example, in this embodiment, the polyphosphate composition may contain at least 20 wt. % calcium and no, or only trace amounts of magnesium. Alternatively, in one embodiment, the polyphosphate composition comprises at least 7 wt. % magnesium and no, or only trace amounts of calcium. By way of further example, in this embodiment, the polyphosphate composition may contain at least 10 wt. % magnesium and no, or only trace amounts of calcium. By way of further example, in this embodiment, the polyphosphate composition may contain at least 12 wt. % magnesium and no, or only trace amounts of calcium. By way of further example, in this embodiment, the polyphosphate composition may contain at least 15 wt. % magnesium and no, or only trace amounts of calcium. By way of further example, in this embodiment, the polyphosphate composition may contain at least 20 wt. % magnesium and no, or only trace amounts of calcium. In yet another embodiment, the polyphosphate composition contains more than trace amounts of each of calcium and magnesium and, in combination, calcium and magnesium constitute at least 7 wt. % of the total weight of the composition. For example, in one embodiment, the polyphosphate composition contains more than trace amounts of each of calcium and magnesium and, in combination, calcium and magnesium constitute at least 12 wt. % of the total weight of the composition. By way of further example, in one embodiment, the polyphosphate composition contains more than trace amounts of each of calcium and magnesium and, in combination, calcium and magnesium constitute at least 15 wt. % of the total weight of the composition. By way of further example, in one embodiment, the polyphosphate composition contains more than trace amounts of each of calcium and magnesium and, in combination, calcium and magnesium constitute at least 20 wt. % of the total weight of the composition.

In general, when the composition contains both calcium and magnesium, it is generally preferred that the atomic ratio of calcium to magnesium be greater than 0.2:1 (calcium:magnesium). For example, the atomic ratio of calcium to magnesium may be greater than 0.5:1 (calcium:magnesium). In certain embodiments, the composition contains more calcium than magnesium. Thus, for example, the atomic ratio of calcium to magnesium may exceed 1.25:1 (calcium:magnesium). In one such preferred embodiment, the atomic ratio of calcium to magnesium exceeds 1.5:1 (calcium:magnesium). In one such preferred embodiment, the atomic ratio of calcium to magnesium exceeds 1.75:1 (calcium:magnesium). In one such preferred embodiment, the atomic ratio of calcium to magnesium exceeds 2:1 (calcium:magnesium). In one such preferred embodiment, the atomic ratio of calcium to magnesium exceeds 4:1 (calcium:magnesium). In one such preferred embodiment, the atomic ratio of calcium to magnesium exceeds 5:1 (calcium:magnesium).

Advantageously, the polyphosphates of the present invention are water-insoluble. That is, the phosphates do not appreciably dissolve in deionized water at room temperature (25° C.) water and neutral pH; for example, the polyphosphates will not release more than 20% of the combined amounts of calcium and magnesium contained by the polyphosphate composition within 10 minutes, and preferably within an hour. Water-insolubility may be conveniently assessed, for example, by reference to the dissolution of the polyphosphate in moderate strength mineral acid. For example, the combined amounts of calcium and magnesium (and any micronutrient metals selected from the group consisting of chromium, cobalt, copper, iron, manganese, selenium, and zinc) contained by the polyphosphate composition that dissolves from the inorganic polyphosphate composition during a 30 minute period in deionized water at room-temperature (25° C.) is less than 20% (by weight) of the combined amount of calcium and magnesium (and any micronutrient metals selected chromium, cobalt, copper, iron, manganese, selenium and zinc) that dissolves from the inorganic polyphosphate composition during a 30 minute period in 0.1N HCl at room-temperature (25° C.). In one preferred embodiment, the amount of such metals that dissolve in DI water is less than 15% of the amount of such metals that dissolve in 0.1N HCl under such conditions. In one preferred embodiment, the amount of such metals that dissolve in DI water is less than 10% of the amount of such metals that dissolve in 0.1N HCl under such conditions. In one preferred embodiment, the amount of such metals that dissolve in DI water is less than 9% of the amount of such metals that dissolve in 0.1N HCl under such conditions. In one preferred embodiment, the amount of such metals that dissolve in DI water is less than 8% of the amount of such metals that dissolve in 0.1N HCl under such conditions.

The polyphosphates dissolve relatively rapidly at room temperature in dilute citric acid. Stated differently, the extent of dissolution in a one hour period in dilute citric acid, such as 6.9 wt. %, 2 wt. %, 1 wt. % or even 0.2 wt % or 0.1 wt. % citric acid, at room temperature is a substantial fraction of the extent of dissolution in significantly stronger acids such as 0.1N HCl acid at room temperature. For example, the combined amount of calcium and magnesium (and any chromium, cobalt, copper, iron, manganese, selenium and zinc) that dissolves from the inorganic polyphosphate composition during a 20 minute period in 6.9 wt. % citric acid at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.); in certain more preferred embodiments, the amount that dissolves in the 2 wt. % citric acid is at 80%, 85%, 90% or even 95% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.). For example, the combined amount of calcium and magnesium (and any chromium, cobalt, copper, iron, manganese, selenium and zinc) that dissolves from the inorganic polyphosphate composition during a 20 minute period in 2 wt. % citric acid at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.); in certain more preferred embodiments, the amount that dissolves in the 2 wt. % citric acid is at 80%, 85%, 90% or even 95% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.). By way of further example, in one embodiment the combined amount of calcium and magnesium (and any chromium, cobalt, copper, iron, manganese, selenium and zinc) that dissolves from the inorganic polyphosphate composition during a 20 minute period in 1 wt. % citric acid at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.); in certain more preferred embodiments, the amount that dissolves in the 1 wt. % citric acid is at 80%, 85%, 90% or even 95% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.). By way of further example, in one embodiment the combined amount of calcium and magnesium (and any chromium, cobalt, copper, iron, manganese, selenium and zinc) that dissolves from the inorganic polyphosphate composition during a 20 minute period in 0.2 wt. % citric acid at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.); in certain more preferred embodiments, the amount that dissolves in the 0.2 wt. % citric acid is at 80%, 85%, 90% or even 95% of the combined amount of calcium and magnesium (and any chromium, cobalt, copper, iron, manganese, selenium and zinc) that dissolves from the inorganic polyphosphate composition during a 20 minute period in 0.1 N HCl at room-temperature (25° C.). By way of further example, in one embodiment the combined amount of calcium and magnesium (and any chromium, cobalt, copper, iron, manganese, selenium and zinc) that dissolves from the inorganic polyphosphate composition during a 20 minute period in 0.1 wt. % citric acid at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.); in certain more preferred embodiments, the amount that dissolves in the 0.1 wt. % citric acid is at 80%, 85%, 90% or even 95% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.).

In one embodiment, the polyphosphate composition preferably also dissolves relatively rapidly at room temperature in dilute ethylenediaminetetraacetic acid (EDTA). Stated differently, the extent of dissolution in a one hour period in 0.005 M EDTA is preferably a substantial fraction of the extent of dissolution in significantly stronger acids such as 0.1N HCl acid at room temperature. For example, the combined amount of calcium and magnesium (and any chromium, cobalt, copper, iron, manganese, selenium and zinc) that dissolves from the inorganic polyphosphate composition during a 20 minute period in 0.005M EDTA at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.). In one preferred embodiment, the amount of such metals that dissolve in 0.005M EDTA is at least 80% of the amount of such metals that dissolve in 0.1N HCl under such conditions. In one preferred embodiment, the amount of such metals that dissolve in 0.005M EDTA is at least 85% of the amount of such metals that dissolve in 0.1 N HCl under such conditions. In one preferred embodiment, the amount of such metals that dissolve in 0.005M EDTA is at least 90% of the amount of such metals that dissolve in 0.1N HCl under such conditions. In one preferred embodiment, the amount of such metals that dissolve in 0.005M EDTA is at least 95% of the amount of such metals that dissolve in 0.1N HCl under such conditions.

In one embodiment, the polyphosphate composition preferably also dissolves relatively rapidly at room temperature in dilute HCl. Stated differently, the extent of dissolution in a one hour period in 0.01 N HCl at room temperature is a substantial fraction of the extent of dissolution in significantly stronger acids such as 0.1N HCl acid at room temperature. For example, the combined amount of calcium and magnesium (and any chromium, cobalt, copper, iron, manganese, selenium and zinc) that dissolves from the inorganic polyphosphate composition during a 20 minute period in 0.01N HCl at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.). In one preferred embodiment, the amount of such metals that dissolve in 0.01N HCl is at least 80% of the amount of such metals that dissolve in 0.1N HCl under such conditions. In one preferred embodiment, the amount of such metals that dissolve in 0.01 N HCl is at least 85% of the amount of such metals that dissolve in 0.1 N HCl under such conditions. In one preferred embodiment, the amount of such metals that dissolve in 0.01 N HCl is at least 90% of the amount of such metals that dissolve in 0.1 N HCl under such conditions. In one preferred embodiment, the amount of such metals that dissolve in 0.01 N HCl is at least 95% of the amount of such metals that dissolve in 0.1 N HCl under such conditions.

In one embodiment, the polyphosphate composition dissolves relatively rapidly at room temperature in 0.2 wt. % citric acid, 0.005M EDTA and 0.01N HCl. In addition, the extent of dissolution in a one hour period in dilute acids such as 0.2 wt. % citric acid, 0.005M EDTA and 0.01N HCl at room temperature is a substantial fraction of the extent of dissolution in significantly stronger acids such as 0.1N HCl acid at room temperature. For example, the combined amount of calcium and magnesium (and any chromium, cobalt, copper, iron, manganese, selenium and zinc) that dissolves from the inorganic polyphosphate composition during a 20 minute period in each of 0.2 wt. % citric acid, 0.005M EDTA and 0.01N HCl at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.). In one preferred embodiment, the amount of such metals that dissolve in each of the dilute acids is at least 80% of the amount of such metals that dissolve in 0.1 N HCl under such conditions. In one preferred embodiment, the amount of such metals that dissolve in each of the dilute acids is at least 85% of the amount of such metals that dissolve in 0.1N HCl under such conditions. In one preferred embodiment, the amount of such metals that dissolve in each of the dilute acids is at least 90% of the amount of such metals that dissolve in 0.1N HCl under such conditions. In one preferred embodiment, the amount of such metals that dissolve in each of the dilute acids is at least 95% of the amount of such metals that dissolve in 0.1 N HCl under such conditions.

In one embodiment, the polyphosphate composition dissolves relatively rapidly at room temperature in 0.1 wt. % citric acid, 0.005M EDTA and 0.01N HCl. In addition, the extent of dissolution in a one hour period in dilute acids such as 0.1 wt. % citric acid, 0.005M EDTA and 0.01N HCl at room temperature is a substantial fraction of the extent of dissolution in significantly stronger acids such as 0.1N HCl acid at room temperature. For example, the combined amount of calcium and magnesium (and any chromium, cobalt, copper, iron, manganese, selenium and zinc) that dissolves from the inorganic polyphosphate composition during a 20 minute period in each of 0.1 wt. % citric acid, 0.005M EDTA and 0.01N HCl at room-temperature (25° C.) is at least 75% of the combined amount of calcium and magnesium (and any chromium, cobalt, copper, iron, manganese, selenium and zinc) that dissolves from the inorganic polyphosphate composition during a 20 minute period in 0.1N HCl at room-temperature (25° C.). In one preferred embodiment, the amount of such metals that dissolve in each of the dilute acids is at least 80% of the amount of such metals that dissolve in 0.1 N HCl under such conditions. In one preferred embodiment, the amount of such metals that dissolve in each of the dilute acids is at least 85% of the amount of such metals that dissolve in 0.1 N HCl under such conditions. In one preferred embodiment, the amount of such metals that dissolve in each of the dilute acids is at least 90% of the amount of such metals that dissolve in 0.1N HCl under such conditions. In one preferred embodiment, the amount of such metals that dissolve in each of the dilute acids is at least 95% of the amount of such metals that dissolve in 0.1N HCl under such conditions.

Depending upon their composition, certain of the polyphosphates can be characterized by their X-ray diffraction reflections at one or more of the following positions: 5.96 (±0.03), 5.37 (±0.03), 5.01 (±0.025), 4.73, 4.61, 4.5, 4.15, 4.04, 3.7, 3.66(±0.01), 3.58(±0.01), 3.47(±0.01), 3.39(±0.01), 3.35(±0.01), 3.19(±0.01), 3.13(±0.01), 3.09(±0.01), 3.05(±0.01), 2.96(±0.009), 2.94(±0.009), 2.82 (±0.009), 2.76(±0.008), 2.73(±0.008), 2.59(±0.007), 2.53(±0.007), 2.5(±0.007), 2.43(±0.007), 2.41(±0.007), 2.37 (±0.007), 2.34(±0.006), 2.25(±0.006), 2.2(±0.006), 2.18(±0.005), 2.16(±0.005), 2.14(±0.005), 2.12(±0.005), 2.09(±0.005), 2.08(±0.005), 2.03(±0.005), 1.99(±0.004), 1.93(±0.004), 1.91(±0.004), 1.85(±0.003), 1.8(±0.003), 1.76 (±0.003), 1.72(±0.003), 1.68(±0.0028), 1.64(±0.0027), 1.59 (±0.0025), 1.57(±0.0024) Å.

Depending upon their composition, certain of the polyphosphates can be characterized by their X-ray diffraction reflections at one or more of the following positions: 7.54 (±0.03), 6.74(±0.03), 5.96 (±0.03), 5.37 (±0.03), 5.01 (±0.025), 4.73, 4.61, 4.5, 4.15, 4.04, 3.7, 3.66(±0.01), 3.58 (±0.01), 3.47(±0.01), 3.39(±0.01), 3.35(±0.01), 3.19(±0.01), 3.13(±0.01), 3.09(±0.01), 3.05(±0.01), 2.96(±0.009), 2.94(±0.009), 2.82(±0.009), 2.76(±0.008), 2.73(±0.008), 2.59(±0.007), 2.53(±0.007), 2.5(±0.007), 2.43(±0.007), 2.41 (±0.007), 2.37(±0.007), 2.34(±0.006), 2.25(±0.006), 2.2(±0.006), 2.18(±0.005), 2.16(±0.005), 2.14(±0.005), 2.12 (±0.005), 2.09(±0.005), 2.08(±0.005), 2.03(±0.005), 1.99(±0.004), 1.93(±0.004), 1.91(±0.004), 1.85(±0.003), 1.8 (±0.003), 1.76(±0.003), 1.72(±0.003), 1.68(±0.0028), 1.64 (±0.0027), 1.59(±0.0025), 1.57(±0.0024) Å.

Advantageously, the polyphosphate composition may comprise a range of metals and other ions other than calcium, magnesium, or a combination thereof.

In an embodiment, the polyphosphate contains zinc as the only micronutrient. In this embodiment, the polyphosphate includes at least about 10 weight percent zinc, based on the total weight of the polyphosphate. In another embodiment, the polyphosphate contains iron as the only micronutrient. In this embodiment, the polyphosphate includes at least about 7 weight percent iron, based on the total weight of the polyphosphate. In another embodiment, the polyphosphate contains manganese as the only micronutrient. In this embodiment, the polyphosphate includes at least about 5 weight percent manganese, based on the total weight of the polyphosphate. In another embodiment, the polyphosphate contains copper as the only micronutrient. In this embodiment, the polyphosphate includes at least about 5 weight percent copper, based on the total weight of the polyphosphate. In another embodiment, the polyphosphate contains chromium as the only micronutrient. In this embodiment, the polyphosphate includes at least about 3 weight percent chromium, based on the total weight of the polyphosphate. In another embodiment, the polyphosphate contains cobalt as the only micronutrient. In this embodiment, the polyphosphate includes at least 1 weight percent cobalt, based on the total weight of the polyphosphate. In another embodiment, the polyphosphate contains at least two different micronutrients. In this embodiment, the polyphosphate includes at least about 8 weight percent total micronutrient, based on the total weight of the polyphosphate. Alternatively, the polyphosphate preferably comprises at least about 10 weight percent, alternatively at least about 15 weight percent, alternatively at least about 20 weight percent, alternatively at least about 22 weight percent, alternatively at least about 25 weight percent, alternatively at least about 30 weight percent, alternatively at least about 35 weight percent, micronutrients based on the total weight of the polyphosphate. Alternately, the composition contains less than 30 wt. % of boron, chromium, cobalt, copper, iodine, iron, manganese, molybdenum, selenium, sulfur and zinc, in combination.

For example, the polyphosphate composition may comprise potassium as a nutrient ion. Typically in this embodiment, the polyphosphate composition preferably contains less than about 20 wt. % potassium, based on the total weight of the polyphosphate composition. In this embodiment, the polyphosphate composition may contain less than about 15 wt. % potassium, based on the total weight of the polyphosphate; in other such embodiments, the polyphosphate contains less than 10 wt. % potassium, less than 5 wt. % potassium, or even less than 1 wt. % potassium. When included, the polyphosphate will typically comprise about 10-15 wt. % potassium.

In one embodiment, the polyphosphate composition contains sodium (e.g., at least about 0.01 wt. % sodium) as a nutrient ion in addition to calcium, magnesium, or a combination thereof. In this embodiment, the polyphosphate composition may contains less than about 10 wt. % sodium, based on the total weight of the polyphosphate; in other such embodiments, the polyphosphate contains less than 7.5 wt. % sodium, less than 5 wt. % sodium, or even less than 1 wt. % sodium. When included, the polyphosphate will typically comprise about 1-5 wt. % sodium.

In one embodiment, the polyphosphate composition contains sulfur (e.g., at least about 0.01 wt. % sulfur) as a nutrient ion in addition to calcium, magnesium, or a combination thereof. In this embodiment, the polyphosphate composition preferably may contain less than about 10 wt. % sulfur, based on the total weight of the polyphosphate; in other such embodiments, the polyphosphate contains less than 7 wt. % sulfur, less than 5 wt. % sulfur, or even less than 1 wt. % sulfur. When included, the polyphosphate will typically comprise about 1 to 7 wt. % sulfur.

In one embodiment, the polyphosphate composition contains ammonium (e.g., at least about 0.01 wt. % ammonium) as a nutrient ion in addition to calcium, magnesium, or a combination thereof. In this embodiment, the polyphosphate composition may contain less than about 10 wt. % ammonium, based on the total weight of the polyphosphate; in other such embodiments, the polyphosphate contains less than 7.5 wt. % ammonium, less than 5 wt. % ammonium, or even less than 1 wt. % ammonium. When included, the polyphosphate will typically comprise about 1-10 wt. % ammonium. When included, the polyphosphate will typically comprise about 1-5 wt. % ammonium.

In one embodiment, the polyphosphate composition contains zinc (e.g., at least about 0.01 wt. % zinc) as a nutrient ion in addition to calcium, magnesium, or a combination thereof.

In this embodiment, the polyphosphate composition may contain less than about 9 weight percent zinc, based on the total weight of the polyphosphate; in other such embodiments, the polyphosphate contains less than 6 wt. % zinc, less than 5 wt. % zinc, less than 4 wt. % zinc, less than 3 wt. % zinc, less than 2 wt. % zinc, less than 1 wt. % zinc, less than 0.5 wt. % zinc, less than 0.25 wt. % zinc, or even less than 0.1 wt. % zinc. When included, the polyphosphate will typically comprise about 1-35 wt. % zinc.

In one embodiment, the polyphosphate composition contains iron (e.g., at least about 0.01 wt. % iron) as a nutrient ion in addition to calcium, magnesium, or a combination thereof. In this embodiment, the polyphosphate composition may contain less than about 6 weight percent iron, based on the total weight of the polyphosphate; in other such embodiments, the polyphosphate contains less than 5 wt. % iron, less than 4 wt. % iron, less than 3 wt. % iron, less than 2 wt. % iron, less than 1 wt. % iron, less than 0.5 wt. % iron, less than 0.25 wt. % iron, or even less than 0.1 wt. % iron. When included, the polyphosphate will typically comprise about 1-10 wt. % iron.

In one embodiment, the polyphosphate composition contains manganese (e.g., at least about 0.01 wt. % manganese) as a nutrient ion in addition to calcium, magnesium, or a combination thereof. In this embodiment, the polyphosphate composition may contain less than about 5 weight percent manganese, based on the total weight of the polyphosphate; 4 weight percent manganese, based on the total weight of the polyphosphate; in other such embodiments, the polyphosphate contains less than 4 wt. % manganese, less than 3 wt. % manganese, less than 2 wt. % manganese, less than 1 wt. manganese, less than 0.5 wt. % manganese, less than 0.25 wt. % manganese, or even less than 0.1 wt. % manganese. When included, the polyphosphate will typically comprise about 1-10 wt. % manganese.

In one embodiment, the polyphosphate composition contains copper (e.g., at least about 0.01 wt. % copper) as a nutrient ion in addition to calcium, magnesium, or a combination thereof. In this embodiment, the polyphosphate composition may contain less than about 12 weight percent copper, 4 weight percent copper, based on the total weight of the polyphosphate; in other such embodiments, the polyphosphate contains less than 5 wt. % copper, less than 4 wt. % copper, less than 3 wt. % copper, less than 2 wt. % copper, less than 1 wt. % copper, less than 0.5 wt. % copper, less than 0.25 wt. % copper, or even less than 0.1 wt. % copper. When included, the polyphosphate will typically comprise about 1-35 wt. % copper.

In one embodiment, the polyphosphate composition contains chromium (e.g., at least about 0.01 wt. % chromium) as a nutrient ion in addition to calcium, magnesium, or a combination thereof. In this embodiment, the polyphosphate composition may contain less than about 5 weight percent chromium, based on the total weight of the polyphosphate; in other such embodiments, the polyphosphate contains less than 4 wt. % chromium, less than 3 wt. % chromium, less than 2 wt. % chromium, less than 1 wt. % chromium, less than 0.5 wt. % chromium, less than 0.25 wt. % chromium, or even less than 0.1 wt. % chromium.

In one embodiment, the polyphosphate composition contains cobalt (e.g., at least about 0.01 wt. % cobalt) as a nutrient ion in addition to calcium, magnesium, or a combination thereof. In this embodiment, the polyphosphate composition may contain less than about 15 weight percent cobalt, based on the total weight of the polyphosphate; in other such embodiments, the polyphosphate contains less than 4 wt. % cobalt, less than 3 wt. % cobalt, less than 2 wt. % cobalt, less than 1 wt. % cobalt, less than 0.9 wt. % cobalt, less than 0.75 wt. % cobalt, less than 0.5 wt. % cobalt, less than 0.25 wt. % cobalt, less than 0.1 wt. % cobalt, or even less than 0.05 wt. % cobalt.

In one embodiment, the polyphosphate composition contains selenium (e.g., at least about 0.01 wt. % selenium) as a nutrient ion in addition to calcium, magnesium, or a combination thereof. In this embodiment, the polyphosphate composition may contain less than about 10 weight percent selenium, based on the total weight of the polyphosphate; in other such embodiments, the polyphosphate contains less than 5 wt. % selenium, less than 3 wt. % selenium, less than 1 wt. % selenium, less than 0.5 wt. % selenium, less than 0.5 wt. % selenium, less than 0.9 wt. % selenium, less than 0.75 wt. % selenium, less than 0.5 wt. % selenium, less than 0.25 wt. % selenium, less than 0.1 wt. % selenium, or even less than 0.05 wt. % selenium.

In one embodiment, the polyphosphate composition contains boron (e.g., at least about 0.01 wt. % boron) as a nutrient ion in addition to calcium, magnesium, or a combination thereof. In this embodiment, the polyphosphate composition may contain less than about 10 weight percent boron, based on the total weight of the polyphosphate; in other such embodiments, the polyphosphate contains less than 5 wt. % boron, less than 2 wt. % boron, less than 1.75 wt. % boron, less than 1.5 wt. % boron, less than 1.25 wt. % boron, less than 1 wt. % boron, less than 0.75 wt. % boron, less than 0.5 wt. % boron, less than 0.25 wt. % boron, less than 0.1 wt. % boron, less than 0.075 wt. % boron, less than 0.05 wt. % boron, less than 0.025 wt. % boron, or even about 0.01 wt. % boron.

In one embodiment, the polyphosphate composition contains iodine (e.g., at least about 0.01 wt. % iodine) as a nutrient ion in addition to calcium, magnesium, or a combination thereof.

In one embodiment, the polyphosphate composition contains molybdenum (e.g., at least about 0.01 wt. % molybdenum) as a nutrient ion in addition to calcium, magnesium, or a combination thereof. In this embodiment, the polyphosphate composition may contain less than about 10 weight percent molybdenum, based on the total weight of the polyphosphate; in other such embodiments, the polyphosphate contains less than 5 wt. % molybdenum, less than 3 wt. % molybdenum, less than 2 wt. % molybdenum, less than 1 wt. % molybdenum, less than 0.09 wt. % molybdenum, less than 0.075 wt. % molybdenum, less than 0.05 wt. % molybdenum, less than 0.025 wt. % molybdenum, or even about 0.01 wt. % molybdenum.

In one embodiment, the polyphosphate composition contains at least 0.01 wt. % of each of at least two different nutrients selected from the group consisting of boron, chromium, cobalt, copper, iodine, iron, manganese, molybdenum, selenium, sulfur and zinc. For example in one such embodiment, the polyphosphate composition contains up to about 15 weight percent of such nutrients, combined, based on the total weight of the polyphosphate composition. For example, in one such embodiment, the polyphosphate composition contains less than about 10 weight percent of such nutrients, combined, based on the total weight of the polyphosphate composition. By way of further example, in one such embodiment, the polyphosphate composition contains less than about 7 weight percent of such nutrients, combined, based on the total weight of the polyphosphate composition. By way of further example, in one such embodiment, the polyphosphate composition contains less than about 6 weight percent of such nutrients, combined, based on the total weight of the polyphosphate composition. By way of further example, in one such embodiment, the polyphosphate composition contains less than about 5 weight percent of such nutrients, combined, based on the total weight of the polyphosphate composition. By way of further example, in one such embodiment, the polyphosphate composition contains less than about 4.5 weight percent of such nutrients, combined, based on the total weight of the polyphosphate composition. By way of further example, in one such embodiment, the polyphosphate composition contains less than about 4 weight percent of such nutrients, combined, based on the total weight of the polyphosphate composition. By way of further example, in one such embodiment, the polyphosphate composition contains less than about 3.5 weight percent of such nutrients, combined, based on the total weight of the polyphosphate composition. By way of further example, in one such embodiment, the polyphosphate composition contains less than about 3 weight percent of such nutrients, combined, based on the total weight of the polyphosphate composition. By way of further example, in one such embodiment, the polyphosphate composition contains less than about 2.5 weight percent of such nutrients, combined, based on the total weight of the polyphosphate composition. By way of further example, in one such embodiment, the polyphosphate composition contains less than about 2 weight percent of such nutrients, combined, based on the total weight of the polyphosphate composition. By way of further example, in one such embodiment, the polyphosphate composition contains less than about 1.5 weight percent of such nutrients, combined, based on the total weight of the polyphosphate composition. By way of further example, in one such embodiment, the polyphosphate composition contains less than about 1 weight percent of such nutrients, combined, based on the total weight of the polyphosphate composition. By way of further example, in one such embodiment, the polyphosphate composition contains less than about 0.5 weight percent of such nutrients, combined, based on the total weight of the polyphosphate composition.

For use as a fertilizer, the polyphosphate compositions of the present invention may optionally contain, in addition to one or more of ammonium, boron, chromium, cobalt, copper, iodine, iron, manganese, molybdenum, potassium, selenium, sodium, sulfur and zinc, other components that contribute to the nutritional, material handling, or other characteristics of the fertilizer. For example, the fertilizer composition may contain a water-soluble N-P-K macronutrient fertilizer composition that has been blended or otherwise combined with the alkaline earth metal polyphosphate composition. By way of further example, the fertilizer may contain organic materials like plant residues that have been blended or otherwise combined with the micronutrient metal polyphosphate composition to improve the material handling characteristics of the fertilizer.

In general, the alkaline earth metal polyphosphate is preferably a solid, free-flowing particulate material. Particle size is not narrowly critical but is generally preferably less than 80 mesh BS. Stated differently, a mass of the particulate polyphosphate composition has a size distribution with substantially all of the particles having a size less than 80 mesh BS. In one embodiment, a significant fraction of the particles have a size less than 150 mesh BS. For example, in one embodiment the majority of the particles in a population of particles are less than 150 mesh BS. By way of further example, in one embodiment a significant fraction of the particles may be smaller than 300 mesh BS; in one such embodiment, the particles have a size distribution with about 20% by volume of the particles having a size less than 300 mesh BS.

In general, the polyphosphate composition is preferably a solid, free-flowing particulate material with relatively low moisture content. Typically, the polyphosphate composition comprises less than 20 wt. % moisture. For example, in certain embodiments, the polyphosphate composition comprises less than 10 wt. % moisture. For example, in certain embodiments, the polyphosphate composition comprises less than 8 wt. % moisture. By way of further example, in certain embodiments the polyphosphate composition comprises less than 5 wt. % moisture.

Alkaline Earth Metal Polyphosphates

In another embodiment, the polyphosphate composition comprises calcium as the only cation (other than protons). In such embodiments, the ratio of the combined number of moles of phosphorus, sulfur, boron, molybdenum, selenium (incorporated in the phosphate, sulfate, borate, molybdate and selenate repeat units) to moles of calcium in the calcium polyphosphate may be greater than 0.5:1, respectively. By way of further example, the ratio of the moles of phosphorus, sulfur, boron, molybdenum, selenium (incorporated in the phosphate, sulfate, borate, molybdate and selenate repeat units) to moles of calcium in the calcium polyphosphate may be greater than 0.66:1, respectively. By way of further example, the ratio of the moles of phosphorus, sulfur, boron, molybdenum, selenium (incorporated in the phosphate, sulfate, borate, molybdate and selenate repeat units) to moles of calcium in the calcium polyphosphate may be greater than 1.1:1, respectively. By way of further example, the ratio of the moles of phosphorus, sulfur, boron, molybdenum, selenium (incorporated in the phosphate, sulfate, borate, molybdate and selenate repeat units) to moles of calcium in the calcium polyphosphate may be greater than 1.67:1, respectively.

In certain embodiments, the ratio of the moles of phosphorus to moles of calcium in the calcium polyphosphate may be greater than 0.5:1, respectively. By way of further example, the ratio of the moles of phosphorus to moles of calcium in the calcium polyphosphate may be greater than 0.66:1, respectively. By way of further example, the ratio of the moles of phosphorus to moles of calcium in the calcium polyphosphate may be greater than 1.1:1, respectively. By way of further example, the ratio of the moles of phosphorus to moles of calcium in the calcium polyphosphate may be greater than 1.67:1, respectively.

In another embodiment, the polyphosphate composition comprises magnesium as the only cation (other than protons). In such embodiments, the ratio of the combined number of moles of phosphorus, sulfur, boron, molybdenum, selenium (incorporated in the phosphate, sulfate, borate, molybdate and selenate repeat units) to moles of magnesium in the magnesium polyphosphate may be greater than 0.5:1, respectively. By way of further example, the ratio of the moles of phosphorus, sulfur, boron, molybdenum, selenium (incorporated in the phosphate, sulfate, borate, molybdate and selenate repeat units) to moles of magnesium in the magnesium polyphosphate may be greater than 0.66:1, respectively. By way of further example, the ratio of the moles of phosphorus, sulfur, boron, molybdenum, selenium (incorporated in the phosphate, sulfate, borate, molybdate and selenate repeat units) to moles of magnesium in the magnesium polyphosphate may be greater than 1.1:1, respectively. By way of further example, the ratio of the moles of phosphorus, sulfur, boron, molybdenum, selenium (incorporated in the phosphate, sulfate, borate, molybdate and selenate repeat units) to moles of magnesium in the magnesium polyphosphate may be greater than 1.67:1, respectively.

In some embodiments, the ratio of the moles of phosphorus to moles of magnesium in the magnesium polyphosphate may be greater than 0.5:1, respectively. By way of further example, the ratio of the moles of phosphorus to moles of magnesium in the magnesium polyphosphate may be greater than 0.66:1, respectively. By way of further example, the ratio of the moles of phosphorus to moles of magnesium in the magnesium polyphosphate may be greater than 1.1:1, respectively. By way of further example, the ratio of the moles of phosphorus to moles of magnesium in the magnesium polyphosphate may be greater than 1.67:1, respectively.

In another embodiment, the polyphosphate composition comprises calcium and magnesium as the only cations (other than protons). For example, the ratio of moles of calcium to moles of magnesium may be greater than 0.2:1, respectively. By way of further example, the ratio of the moles of calcium to moles of magnesium may be greater than 0.5:1, respectively. By way of further example, the ratio of the moles of calcium to moles of magnesium may be greater than 1:1, respectively. By way of further example, the ratio of the moles of calcium to moles of magnesium may be greater than 2:1, respectively. By way of further example, the ratio of moles of calcium to moles of magnesium may be greater than 4:1, respectively. By way of further example, the ratio of the moles of calcium to moles of magnesium may be greater than 5:1, respectively. By way of further example, the ratio of the combined number of moles of phosphorus, sulfur, boron, molybdenum, and selenium (incorporated in the phosphate, sulfate, borate, molybdate and selenate repeat units) to moles of calcium and magnesium (in combination) in the polyphosphate may be greater than 0.67:1, respectively. By way of further example, the ratio of the combined number of moles of phosphorus, sulfur, boron, molybdenum, and selenium (incorporated in the phosphate, sulfate, borate, molybdate and selenate repeat units) to moles of calcium and magnesium (in combination) in the polyphosphate may be greater than 0.74:1, respectively. By way of further example, the ratio of the combined number of moles of phosphorus, sulfur, boron, molybdenum, and selenium (incorporated in the phosphate, sulfate, borate, molybdate and selenate repeat units) to moles of calcium and magnesium (in combination) in the polyphosphate may be greater than 0.83:1, respectively. By way of further example, the ratio of the combined number of moles of phosphorus, sulfur, boron, molybdenum, and selenium (incorporated in the phosphate, sulfate, borate, molybdate and selenate repeat units) to moles of calcium and magnesium (in combination) in the polyphosphate may be greater than 0.95:1, respectively. By way of further example, the ratio of the combined number of moles of phosphorus, sulfur, boron, molybdenum, and selenium (incorporated in the phosphate, sulfate, borate, molybdate and selenate repeat units) to moles of calcium and magnesium (in combination) in the polyphosphate may be greater than 1.1:1, respectively. By way of further example, the ratio of the combined number of moles of phosphorus, sulfur, boron, molybdenum, and selenium (incorporated in the phosphate, sulfate, borate, molybdate and selenate repeat units) to moles of calcium and magnesium (in combination) in the polyphosphate may be greater than 1.33:1, respectively. By way of further example, the ratio of the combined number of moles of phosphorus, sulfur, boron, molybdenum, and selenium (incorporated in the phosphate, sulfate, borate, molybdate and selenate repeat units) to moles of calcium and magnesium (in combination) in the polyphosphate may be equal to 1.67.1, respectively.

In certain embodiments, the ratio of the moles of phosphorus to moles of calcium and magnesium (in combination) in the polyphosphate may be greater than 0.5:1, respectively. By way of further example, the ratio of the moles of phosphorus to moles of calcium and magnesium (in combination) in the polyphosphate may be greater than 0.67:1, respectively. By way of further example, the ratio of the moles of phosphorus to moles of calcium and magnesium (in combination) in the polyphosphate may be greater than 0.74:1, respectively. By way of further example, the ratio of the moles of phosphorus to moles of calcium and magnesium (in combination) in the polyphosphate may be greater than 0.83:1, respectively. By way of further example, the ratio of the moles of phosphorus to moles of calcium and magnesium (in combination) in the polyphosphate may be greater than 0.95:1, respectively. By way of further example, the ratio of the moles of phosphorus to moles of calcium and magnesium (in combination) in the polyphosphate may be greater than 1.1:1, respectively. By way of further example, the ratio of the moles of phosphorus to moles of calcium and magnesium (in combination) in the polyphosphate may be greater than 1.33:1, respectively. By way of further example, the ratio of the moles of phosphorus to moles of calcium and magnesium (in combination) in the polyphosphate may be equal to 1.67.1, respectively.

In one embodiment, the polyphosphate composition comprises calcium, magnesium and one nutrient ion as the only cations (other than protons). For example, alkaline earth metal polyphosphate composition may comprise only calcium and magnesium and zinc as the only cations (other than protons). By way of further example, the ratio of the combined number of moles of phosphorus, sulfur, boron, molybdenum and selenium incorporated in the repeat units to moles of zinc in the polyphosphate may be at least 2:1, respectively. By way of further example, the ratio of the combined number of moles of phosphorus, sulfur, boron, molybdenum and selenium incorporated in the repeat units to moles of zinc in the polyphosphate may be greater than 5:1, respectively. By way of further example, the ratio of the moles of phosphorus to moles of zinc in the polyphosphate may be greater than 5:1, respectively. By way of further example, the ratio of the combined number of moles of phosphorus, sulfur, boron, molybdenum and selenium incorporated in the repeat units to moles of zinc in the polyphosphate may be greater than 10:1, respectively. By way of further example, the ratio of the moles of phosphorus to moles of zinc in the polyphosphate may be greater than 10:1, respectively. By way of further example, the ratio of the combined number of moles of phosphorus, sulfur, boron, molybdenum and selenium incorporated in the repeat units to moles of zinc in the polyphosphate may be greater than 20:1, respectively. By way of further example, the ratio of the moles of phosphorus to moles of zinc in the polyphosphate may be greater than 20:1, respectively.

In one embodiment, the polyphosphate composition comprises calcium, magnesium and one nutrient ion as the only cations (other than protons). For example, alkaline earth metal polyphosphate composition may comprise only calcium and magnesium and zinc as the only cations (other than protons). The ratio of the equivalents of zinc to phosphorous in the alkaline earth metal polyphosphate when the polyphosphate composition comprises calcium, magnesium and one nutrient ion as the only cations (other than protons). In one embodiment, the alkaline earth metal polyphosphate composition comprises zinc as the only primary micronutrient metal. In such embodiments, the ratio of the equivalents of zinc to phosphorous in the polyphosphate may be 0.33:1, respectively. By way of further example, in one embodiment in which zinc is the only primary micronutrient metal, the ratio of the equivalents of zinc to phosphorous in the alkaline earth metal polyphosphate may be less than 0.33:1, respectively. By way of further example, in one embodiment in which zinc is the only primary micronutrient metal, the ratio of the equivalents of zinc to phosphorous in the alkaline earth metal polyphosphate may be less than 0.3:1, respectively. By way of further example, in one embodiment in which zinc is the only primary micronutrient metal, the ratio of the equivalents of zinc to phosphorous in the alkaline earth metal polyphosphate may be less than 0.2:1, respectively. By way of further example, in one embodiment in which zinc is the only primary micronutrient metal, the ratio of the equivalents of zinc to phosphorous in the alkaline earth metal polyphosphate may be less than 0.1:1, respectively.

In one embodiment, the polyphosphate composition comprises calcium, magnesium and one nutrient ion as the only cations (other than protons). For example, the polyphosphate composition may comprise only calcium, magnesium and iron as the only cations (other than protons). By way of further example, the ratio of the combined number of moles of phosphorus, sulfur, boron, molybdenum and selenium incorporated in the repeat units to moles of iron in the polyphosphate may be greater than 3:1. By way of further example, the ratio of the combined number of moles of phosphorus, sulfur, boron, molybdenum and selenium incorporated in the repeat units to moles of iron in the polyphosphate may be greater than 5:1, respectively. By way of further example, the ratio of the moles of phosphorus to moles of iron in the polyphosphate may be greater than 5:1, respectively. By way of further example, the ratio of the combined number of moles of phosphorus, sulfur, boron, molybdenum and selenium incorporated in the repeat units to moles of iron in the polyphosphate may be greater than 10:1, respectively. By way of further example, the ratio of the moles of phosphorus to moles of iron in the polyphosphate may be greater than 10:1, respectively. By way of further example, the ratio of the combined number of moles of phosphorus, sulfur, boron, molybdenum and selenium incorporated in the repeat units to moles of iron in the polyphosphate may be greater than 20:1, respectively. By way of further example, the ratio of the moles of phosphorus to moles of iron in the polyphosphate may be greater than 20:1, respectively.

In one embodiment, the polyphosphate composition comprises calcium, magnesium and one nutrient ion as the only cations (other than protons). For example, alkaline earth metal polyphosphate composition may comprise only calcium and magnesium and iron as the only cations (other than protons). In one embodiment, the alkaline earth metal polyphosphate composition comprises iron as the only primary micronutrient metal. In such embodiments, the ratio of the equivalents of iron to phosphorous in the polyphosphate may be 0.33:1, respectively. By way of further example, in one embodiment in which iron is the only primary micronutrient metal, the ratio of the equivalents of iron to phosphorous in the alkaline earth metal polyphosphate may be less than 0.33:1, respectively. By way of further example, in one embodiment in which iron is the only primary micronutrient metal, the ratio of the equivalents of iron to phosphorous in the alkaline earth metal polyphosphate may be less than 0.3:1, respectively. By way of further example, in one embodiment in which iron is the only primary micronutrient metal, the ratio of the equivalents of iron to phosphorous in the alkaline earth metal polyphosphate may be less than 0.2:1, respectively. By way of further example, in one embodiment in which iron is the only primary micronutrient metal, the ratio of the equivalents of zinc to phosphorous in the alkaline earth metal polyphosphate may be less than 0.1:1, respectively.

In one embodiment, the polyphosphate composition comprises calcium, magnesium and one nutrient ion as the only cations (other than protons). For example, polyphosphate composition may comprise only calcium and magnesium and manganese as the only cations (other than protons). By way of further example, the ratio of the combined number of moles of phosphorus, sulfur, boron, molybdenum and selenium incorporated in the repeat units to moles of manganese in the polyphosphate may be greater than 2:1, respectively. By way of further example, the ratio of the combined number of moles of phosphorus, sulfur, boron, molybdenum and selenium incorporated in the repeat units to moles of manganese in the polyphosphate may be greater than 4:1, respectively. By way of further example, the ratio of the combined number of moles of phosphorus, sulfur, boron, molybdenum and selenium incorporated in the repeat units to moles of manganese in the polyphosphate may be greater than 3:1, respectively. By way of further example, the ratio of the combined number of moles of phosphorus, sulfur, boron, molybdenum and selenium incorporated in the repeat units to moles of manganese in the polyphosphate may be greater than 5:1, respectively. By way of further example, the ratio of the moles of phosphorus to moles of manganese to in the polyphosphate may be greater than 5:1, respectively. By way of further example, the ratio of the combined number of moles of phosphorus, sulfur, boron, molybdenum and selenium incorporated in the repeat units to moles of manganese in the polyphosphate may be greater than 10:1, respectively. By way of further example, the ratio of the moles of phosphorus to moles of manganese to in the polyphosphate may be greater than 10:1, respectively. By way of further example, the ratio of the combined number of moles of phosphorus, sulfur, boron, molybdenum and selenium incorporated in the repeat units to moles of manganese in the polyphosphate may be greater than 20:1, respectively. By way of further example, the ratio of the moles of phosphorus to moles of manganese in the polyphosphate may be greater than 20:1, respectively.

In one embodiment, the polyphosphate composition comprises calcium, magnesium and one nutrient ion as the only cations (other than protons). For example, alkaline earth metal polyphosphate composition may comprise only calcium and magnesium and manganese as the only cations (other than protons). In one embodiment, the alkaline earth metal polyphosphate composition comprises manganese as the only primary micronutrient metal. In such embodiments, the ratio of the equivalents of manganese to phosphorous in the polyphosphate may be 0.33:1, respectively. By way of further example, in one embodiment in which manganese is the only primary micronutrient metal, the ratio of the equivalents of manganese to phosphorous in the alkaline earth metal polyphosphate may be less than 0.33:1, respectively. By way of further example, in one embodiment in which manganese is the only primary micronutrient metal, the ratio of the equivalents of manganese to phosphorous in the alkaline earth metal polyphosphate may be less than 0.3:1, respectively. By way of further example, in one embodiment in which manganese is the only primary micronutrient metal, the ratio of the equivalents of manganese to phosphorous in the alkaline earth metal polyphosphate may be less than 0.2:1, respectively. By way of further example, in one embodiment in which manganese is the only primary micronutrient metal, the ratio of the equivalents of zinc to phosphorous in the alkaline earth metal polyphosphate may be less than 0.1:1, respectively.

In one embodiment, the alkaline earth metal polyphosphate composition comprises calcium, magnesium and one nutrient ion as the only cations (other than protons). For example, alkaline earth metal polyphosphate composition may comprise calcium, magnesium and boron as the only cations (other than protons). By way of further example, the ratio of the moles of phosphorus to moles of boron to in the polyphosphate may be greater than 2:1, respectively. By way of further example, the ratio of the moles of phosphorus to moles of boron to in the polyphosphate may be greater than 5:1, respectively. By way of further example, the ratio of the moles of phosphorus to moles of boron to in the polyphosphate may be greater than 10:1, respectively. By way of further example, the ratio of the moles of phosphorus to moles of boron in the polyphosphate may be greater than 20:1, respectively.

In one embodiment, the alkaline earth metal polyphosphate composition comprises calcium, magnesium and one nutrient ion as the only cations (other than protons). For example, alkaline earth metal polyphosphate composition may comprise calcium, magnesium and copper as the only cations (other than protons). By way of further example, the ratio of the combined number of moles of phosphorus, sulfur, boron, molybdenum and selenium incorporated in the repeat units to moles of copper in the polyphosphate may be greater than 2:1, respectively. By way of further example, the ratio of the moles of phosphorus to moles of copper in the polyphosphate may be greater than 3:1, respectively. By way of further example, the ratio of the combined number of moles of phosphorus, sulfur, boron, molybdenum and selenium incorporated in the repeat units to moles of copper in the polyphosphate may be greater than 5:1, respectively. By way of further example, the ratio of the moles of phosphorus to moles of copper in the polyphosphate may be greater than 5:1, respectively. By way of further example, the ratio of the combined number of moles of phosphorus, sulfur, boron, molybdenum and selenium incorporated in the repeat units to moles of copper in the polyphosphate may be greater than 10:1, respectively. By way of further example, the ratio of the moles of phosphorus to moles of copper in the polyphosphate may be greater than 10:1, respectively. By way of further example, the ratio of the combined number of moles of phosphorus, sulfur, boron, molybdenum and selenium incorporated in the repeat units to moles of copper in the polyphosphate may be greater than 20:1, respectively. By way of further example, the ratio of the moles of phosphorus to moles of copper in the polyphosphate may be greater than 20:1, respectively.

In one embodiment, the polyphosphate composition comprises calcium, magnesium and one nutrient ion as the only cations (other than protons). For example, alkaline earth metal polyphosphate composition may comprise only calcium and magnesium and copper as the only cations (other than protons). In one embodiment, the alkaline earth metal polyphosphate composition comprises copper as the only primary micronutrient metal. In such embodiments, the ratio of the equivalents of copper to phosphorous in the polyphosphate may be 0.33:1, respectively. By way of further example, in one embodiment in which copper is the only primary micronutrient metal, the ratio of the equivalents of copper to phosphorous in the alkaline earth metal polyphosphate may be less than 0.33:1, respectively. By way of further example, in one embodiment in which copper is the only primary micronutrient metal, the ratio of the equivalents of copper to phosphorous in the alkaline earth metal polyphosphate may be less than 0.3:1, respectively. By way of further example, in one embodiment in which copper is the only primary micronutrient metal, the ratio of the equivalents of copper to phosphorous in the alkaline earth metal polyphosphate may be less than 0.2:1, respectively. By way of further example, in one embodiment in which copper is the only primary micronutrient metal, the ratio of the equivalents of zinc to phosphorous in the alkaline earth metal polyphosphate may be less than 0.1:1, respectively.

In one embodiment, the alkaline earth metal polyphosphate composition comprises calcium, magnesium, and one nutrient ion as the only cations (other than protons). For example, alkaline earth metal polyphosphate composition may comprise calcium, magnesium and selenium as the only cations (other than protons). By way of further example, the ratio of the moles of phosphorus to moles of selenium in the polyphosphate may be greater than 2:1, respectively. By way of further example, the ratio of the moles of phosphorus to moles of selenium in the polyphosphate may be greater than 5:1, respectively. By way of further example, the ratio of the moles of phosphorus to moles of selenium in the polyphosphate may be greater than 10:1, respectively. By way of further example, the ratio of the moles of phosphorus to moles of selenium in the polyphosphate may be greater than 20:1, respectively.

In one embodiment, the alkaline earth metal polyphosphate composition comprises calcium, magnesium, and one nutrient ion as the only cations (other than protons). For example, alkaline earth metal polyphosphate composition may comprise calcium, magnesium and molybdenum as the only cations (other than protons). By way of further example, the ratio of the moles of phosphorus to moles of molybdenum in the polyphosphate may be greater than 2:1, respectively. By way of further example, the ratio of the moles of phosphorus to moles of molybdenum in the polyphosphate may be greater than 5:1, respectively. By way of further example, the ratio of the moles of phosphorus to moles of molybdenum in the polyphosphate may be greater than 10:1, respectively. By way of further example, the ratio of the moles of phosphorus to moles of molybdenum in the polyphosphate may be greater than 20:1, respectively.

More generally, in certain embodiments the ratio of the moles of phosphorus to moles of nutrient ions (selected from among boron, chromium, cobalt, copper, iodine, iron, manganese, molybdenum, selenium, sulfur and zinc) will be greater than 2:1, respectively. For example, in one embodiment in which the polyphosphate comprises two or more nutrient ions (selected from among boron, chromium, cobalt, copper, iodine, iron, manganese, molybdenum, selenium and zinc), the ratio of the moles of phosphorus to moles of the nutrient ions will be greater than 5:1, respectively. For example, in one embodiment in which the polyphosphate comprises two or more nutrient ions (selected from among boron, chromium, cobalt, copper, iodine, iron, manganese, molybdenum, selenium and zinc), the ratio of the moles of phosphorus to moles of the nutrient ions will be greater than 10:1, respectively. For example, in one embodiment in which the polyphosphate comprises two or more nutrient ions (selected from among boron, chromium, cobalt, copper, iodine, iron, manganese, molybdenum, selenium, sulfur and zinc), the ratio of the moles of phosphorus to moles of the nutrient ions will be greater than 20:1, respectively.

As described elsewhere herein, the polyphosphate compositions may be neutralized post-polymerization for improved material handling characteristics. In general, it is preferred that the equilibrium pH of an aqueous mixture of ten parts by weight of water at neutral pH and one part by weight of the neutralized polyphosphate be at least pH 2. More preferably, the equilibrium pH of an aqueous mixture of ten parts by weight of water at neutral pH and one part by weight of the neutralized polyphosphate be at least pH 3. Still more preferably, the equilibrium pH of an aqueous mixture of ten parts by weight of water at neutral pH and one part by weight of the neutralized polyphosphate be at least pH 4. Still more preferably, the equilibrium pH of an aqueous mixture of ten parts by weight of water at neutral pH and one part by weight of the neutralized polyphosphate be at least pH 5. In certain embodiments, the equilibrium pH of an aqueous mixture of ten parts by weight of water at neutral pH and one part by weight of the neutralized polyphosphate be at least pH 6. For example, in one embodiment, the equilibrium pH of an aqueous mixture of ten parts by weight of water at neutral pH and one part by weight of the neutralized polyphosphate will be in the range of pH 4-8.

Calcium Polyphosphate Compositions

In one embodiment, the polyphosphate composition of the present invention comprises calcium as a cation. In general, polyphosphate compositions containing calcium as a cation contain at least 7 wt. % calcium. Typically, polyphosphate compositions containing calcium as a cation contain at least 10 wt. % calcium. In certain embodiments, polyphosphate compositions containing calcium as a cation contain at least 13 wt. % calcium. In certain embodiments, polyphosphate compositions containing calcium as a cation contain at least 15 wt. % calcium. In other embodiments, polyphosphate compositions containing calcium as a cation contain at least 20 wt. % calcium. In other embodiments, polyphosphate compositions containing calcium as a cation contain at least 25 wt. % calcium. For example, in one embodiment, the polyphosphate compositions containing calcium as a cation contain 7-25 wt. % calcium. By way of further example, in one embodiment, the polyphosphate compositions containing calcium as a cation contain 7-35 wt. % calcium. In each of these embodiments, the calcium polyphosphate may optionally contain magnesium and one or more of the other nutrient ions described herein, or yet other compositions that may contribute to the nutritional, material or handling characteristics of the polyphosphate composition as a fertilizer.

Calcium polyphosphate fertilizers compositions of the present invention may optionally contain other components that contribute to the nutritional, material handling, or other characteristics of the fertilizer. For example, the calcium micronutrient fertilizer may contain a water-soluble N-P-K macronutrient fertilizer that has been blended or otherwise combined with the calcium polyphosphate composition. By way of further example, the calcium polyphosphate fertilizer may contain water-soluble or even water-insoluble nutrient compounds that has been blended or otherwise combined with the calcium polyphosphate composition. By way of further example, the calcium polyphosphate fertilizer may contain organic materials like plant residues that have been blended or otherwise combined with the calcium polyphosphate composition to improve the material handling characteristics of calcium polyphosphate fertilizer.

Calcium polyphosphate compositions may be prepared by combining a calcium source material, phosphoric acid and, optionally, one or more additional materials to form a reaction mixture and reacting the components of the mixture to form the calcium polyphosphate. The polyphosphate is neutralized with calcium oxide or carbonate. The optional additional materials include, for example, magnesium and one or more of the other nutrient ions described herein. The calcium source material may be any source of calcium that is compatible with the polymerization process of the present invention. Such sources include, for example, calcium oxide, calcium carbonate, limestone, rock phosphate (apatite), calcium sulfate and calcium chloride.

Magnesium Polyphosphate Compositions

In one embodiment, the polyphosphate composition of the present invention comprises magnesium as a cation. In general, polyphosphate compositions containing magnesium as a cation contain at least 7 wt. % magnesium. Typically, polyphosphate compositions containing magnesium as a cation contain at least 10 wt. % magnesium. In certain embodiments, polyphosphate compositions containing magnesium as a cation contain at least 13 wt. % magnesium. In certain embodiments, polyphosphate compositions containing magnesium as a cation contain at least 15 wt % magnesium. In other embodiments, polyphosphate compositions containing magnesium as a cation contain at least 20 wt. % magnesium. In other embodiments, polyphosphate compositions containing magnesium as a cation contain at least 25 wt. % magnesium. By way of further example, in one embodiment, the polyphosphate compositions containing calcium as a cation contain 7-35 wt. % magnesium. In each of these embodiments, the magnesium polyphosphate may optionally contain calcium and one or more of the other nutrient ions described herein, or yet other compositions that may contribute to the nutritional, material or handling characteristics of the polyphosphate composition as a fertilizer.

Magnesium polyphosphate fertilizers of the present invention may optionally contain other components that contribute to the nutritional, material handling, or other characteristics of the polyphosphate composition. For example, the magnesium micronutrient composition may contain a water-soluble N-P-K macronutrient fertilizer that has been blended or otherwise combined with the magnesium polyphosphate composition. By way of further example, the magnesium polyphosphate composition may contain water-soluble or even water-insoluble nutrient compounds that has been blended or otherwise combined with the magnesium polyphosphate composition. By way of further example, the magnesium polyphosphate composition may contain organic materials like plant residues that have been blended or otherwise combined with the magnesium polyphosphate composition to improve the material handling characteristics of the composition.

Magnesium polyphosphate compositions may be prepared by combining a magnesium source material, phosphoric acid and, optionally, one or more additional materials to form a reaction mixture and reacting the components of the mixture to form the magnesium polyphosphate. The magnesium polyphosphate is neutralized with a basic magnesium source that may include magnesium oxide and magnesium carbonate. The optional additional materials include, for example, calcium and one or more of the other nutrient ions described herein. The magnesium source material may be any source of magnesium that is compatible with the polymerization process of the present invention. Such sources include, for example, magnesium oxide, magnesium carbonate, magnesite, magnesium sulfate, and magnesium chloride.

Polyphosphate Fertilizers Containing Two Alkaline Earth Metal Ions

As noted, the polyphosphate may contain one or more alkaline earth metal and one or more nutrient ions. In general fertilizers that contain two alkaline earth metals contain at least 7 wt. % alkaline earth metals, more typically at least 10 wt. % of alkaline earth metals. Additionally, the alkaline earth metals may be present in any of the concentrations recited herein in connection with the calcium polyphosphate fertilizers and magnesium polyphosphate fertilizers. For example, the fertilizer may contain 7-35 wt. % calcium and/or 7-35 wt. % magnesium. By way of further example, the fertilizer may contain 7-25 wt. % calcium and/or 7-25 wt. % magnesium. In addition, the fertilizer may optionally comprise one or more of the nutrient ions such as one or more of potassium, ammonium, sodium, zinc, iron, manganese, copper, boron, molybdenum, selenium, iodine and cobalt.

For certain applications, it is preferred that the alkaline earth metal polyphosphate contains a combination of nutrient ions. In one such embodiment, the alkaline earth metals polyphosphate contains potassium as nutrient ion. For example, in one such embodiment, the potassium constitutes at least 0.01 wt. % of the alkaline earth metals polyphosphate composition. By way of further example, in one such embodiment, the potassium constitutes at least 2 wt. % of the alkaline earth metals polyphosphate composition. By way of further example, in one such embodiment, the potassium constitutes at least 10 wt. % of the alkaline earth metals polyphosphate composition. By way of further example, in one such embodiment, the potassium constitutes at least 20 wt. % of the alkaline earth metals polyphosphate composition.

For other applications it is preferred that the alkaline earth metal polyphosphate contain ammonium as nutrient ion. For example, in one such embodiment, the ammonium constitutes at least 0.01 wt. % of the alkaline earth metal polyphosphate composition. By way of further example, in one such embodiment, the ammonium constitutes at least 4 wt. % of the alkaline earth metal polyphosphate composition. By way of further example, in one such embodiment, the ammonium constitutes at least 10 wt. % of the alkaline earth metal polyphosphate composition. By way of further example, in one such embodiment, the ammonium constitutes 4-15 wt. % of the alkaline earth metal polyphosphate composition.

For other applications it is preferred that the alkaline earth metal polyphosphate contains zinc as nutrient ion. For example, in one such embodiment, the zinc constitutes at least 0.01 wt. % of the alkaline earth metal polyphosphate composition. By way of further example, in one such embodiment, the zinc constitutes less than 9 wt. % of the alkaline earth metal polyphosphate composition. By way of further example, in one such embodiment, the zinc constitutes less than 5 wt. % of the alkaline earth metal polyphosphate composition. By way of further example, in one such embodiment, the zinc constitutes less than 2 wt. % of the alkaline earth metal polyphosphate composition.

For other applications it is preferred that the alkaline earth metal polyphosphate contains iron as nutrient ion. For example, in one such embodiment, the iron constitutes at least 0.01 wt. % of the alkaline earth metal polyphosphate composition. By way of further example, in one such embodiment, the iron constitutes less than 6 wt. % of the alkaline earth metal polyphosphate composition. By way of further example, in one such embodiment, the iron constitutes less than 3 wt. % of the alkaline earth metal polyphosphate composition. By way of further example, in one such embodiment, the iron constitutes less than 1 wt. % of the alkaline earth metal polyphosphate composition.

For other applications it is preferred that the alkaline earth metal polyphosphate contains manganese as nutrient ion. For example, in one such embodiment, the manganese constitutes at least 0.01 wt. % of the alkaline earth metal polyphosphate composition. By way of further example, in one such embodiment, the manganese constitutes less than 5 wt. % of the alkaline earth metal polyphosphate composition. By way of further example, in one such embodiment, the manganese constitutes less than 2 wt. % of the alkaline earth metal polyphosphate composition. By way of further example, in one such embodiment, the manganese constitutes less than 1 wt. % of the alkaline earth metal polyphosphate composition.

For other applications it is preferred that the alkaline earth metal polyphosphate contains copper as nutrient ion. For example, in one such embodiment, the copper constitutes at least 0.01 wt. % of the alkaline earth metal polyphosphate composition. By way of further example, in one such embodiment, the copper constitutes less than 5 wt. % of the alkaline earth metal polyphosphate composition. By way of further example, in one such embodiment, the copper constitutes less than 2 wt. % of the alkaline earth metal polyphosphate composition. By way of further example, in one such embodiment, the copper constitutes less than 1 wt. % of the alkaline earth metal polyphosphate composition.

For other applications it is preferred that the alkaline earth metal polyphosphate contains boron as nutrient ion. For example, in one such embodiment, the boron constitutes at least 0.01 wt. % of the alkaline earth metal polyphosphate composition. By way of further example, in one such embodiment, the boron constitutes less than 5 wt. % of the alkaline earth metal polyphosphate composition. By way of further example, in one such embodiment, the boron constitutes less than 2 wt. % of the alkaline earth metal polyphosphate composition. By way of further example, in one such embodiment, the boron constitutes less than 1 wt. % of the alkaline earth metal polyphosphate composition.

For other applications it is preferred that the alkaline earth metal polyphosphate contains selenium as nutrient ion. For example, in one such embodiment, the selenium constitutes at least 0.01 wt. % of the alkaline earth metal polyphosphate composition. By way of further example, in one such embodiment, the selenium constitutes less than 5 wt. % of the alkaline earth metal polyphosphate composition. By way of further example, in one such embodiment, the selenium constitutes less than 2 wt. % of the alkaline earth metal polyphosphate composition. By way of further example, in one such embodiment, the selenium constitutes less than 1 wt. % of the alkaline earth metal polyphosphate composition For other applications it is preferred that the alkaline earth metal polyphosphate contain one or more of the nutrient ions disclosed herein. For example, in one embodiment the micronutrient metal polyphosphate may contain less than 5 wt. % zinc and less than 2 wt. % boron. By way of further example, in one embodiment the alkaline earth metal polyphosphate may contain less than 3 wt. % zinc and less than 2 wt. % boron. By way of further example, in one embodiment the micronutrient metal polyphosphate may contain less than 2 wt. % zinc and less than 0.2 wt. % boron.

For other applications it is preferred that the alkaline earth metal polyphosphate contain potassium, zinc, iron and manganese as nutrients. For example, in one such embodiment, the potassium, zinc, iron and manganese, in combination, constitute less than 20 wt. % of the alkaline earth metal polyphosphate composition. By way of further example, in one such embodiment, the potassium, zinc, iron and manganese, in combination, constitute less than 10 wt. % of the alkaline earth metal polyphosphate composition. By way of further example, in one such embodiment, the potassium, zinc, iron and manganese, in combination, constitute less than 5 wt. % of the alkaline earth metal polyphosphate composition Micronutrient Metal Polyphosphates In general, the micronutrient metal polyphosphates of the present invention may be polymerized to various degrees. As previously discussed in connection with the polyphosphate compositions, for example, the average chain length (number average) may be in the range of about 1.5 and 30 phosphate units (phosphorus atoms) per chain. In one embodiment, the average chain length (number average) is about 2 to 20 phosphate units (phosphorus atoms) per chain. In general, it is preferred that the chain length be at the shorter end of the range. For example, in certain embodiments it is preferred that the average chain length (number average) be between 5 and 8 phosphate units (phosphorus atoms) per chain.

Advantageously, the micronutrient metal polyphosphates of the present invention are water-insoluble. That is, the micronutrient metal polyphosphates do not appreciably dissolve in water at room temperature (25° C.) water and neutral pH; for example, the micronutrient metal polyphosphates will not release more than 15% of their micronutrient metals in water within 10 minutes, and preferably within an hour. The micronutrient metal polyphosphates, however, dissolve relatively rapidly at room temperature in dilute acids such as 2 wt. % citric acid and 0.005M diethylenetriaminepentaacetic acid (DTPA). In addition, the extent of dissolution in a one hour period in dilute acids such as 2 wt. % citric acid and 0.005M DTPA at room temperature is a substantial fraction of the extent of dissolution in significantly stronger acids such as 0.1 N HCl acid at room temperature. For example, the extent of dissolution in dilute acids such as 2 wt. % citric acid and 0.005M DTPA will typically be at least 50% of the extent of dissolution in 0.1N HCl in a one-hour period at room temperature. In certain preferred embodiments, the extent of dissolution in a one hour period in dilute acids such as 2 wt. % citric acid and 0.005M DTPA at room temperature will be at least 60% of the extent of dissolution in significantly stronger acids such as 0.1N HCl in a one-hour period at room temperature. In certain more preferred embodiments, the extent of dissolution in a one hour period in dilute acids such as 2 wt. % citric acid and 0.005M DTPA at room temperature will be at least 70% of the extent of dissolution in significantly stronger acids such as 0.1N HCl in a one-hour period at room temperature. In certain more preferred embodiments, the extent of dissolution in a one hour period in dilute acids such as 2 wt. % citric acid and 0.005M DTPA at room temperature will be at least 90% of the extent of dissolution in significantly stronger acids such as 0.1 N HCl in a one-hour period at room temperature. In certain more preferred embodiments, the extent of dissolution in a 30 minute period in dilute acids such as 6.9 wt. % citric acid at room temperature will be at least 70% of the extent of dissolution in significantly stronger acids such as 0.1 N HCl in a 30 minutes period at room temperature. In certain more preferred embodiments, the extent of dissolution in a one hour period in dilute acids such as 6.9 wt. % citric acid at room temperature will be at least 80% of the extent of dissolution in significantly stronger acids such as 0.1N HCl in a 30 minutes period at room temperature. In certain more preferred embodiments, the extent of dissolution in a one hour period in dilute acids such as 6.9 wt. % citric acid at room temperature will be at least 90% of the extent of dissolution in significantly stronger acids such as 0.1 N HCl in a 30 minutes period at room temperature.

In certain embodiments, zinc polyphosphates of the present invention are particularly soluble in dilute acids. For example, within ten minutes at room temperature, micronutrient metal polyphosphates containing zinc as the only primary micronutrient will dissolve to the same extent in dilute acids such as 2 wt. % citric acid and 0.005M DTPA as in significantly stronger acids such as 0.1N HCl acid.

In addition to being soluble in dilute acids, the micronutrient polyphosphate compositions of the present invention contain relatively large proportions of primary micronutrient metal concentrations. One manner of viewing this capacity is to compare the amount of primary micronutrient metal in the polyphosphate composition to the amount of phosphate (phosphorous atoms) in the polyphosphate composition.

In one embodiment, the micronutrient metal polyphosphate composition comprises zinc as the only primary micronutrient metal. In such embodiments, the ratio of the equivalents of zinc to phosphorous in the zinc polyphosphate may be greater than 0.33:1, respectively. By way of further example, in one embodiment in which zinc is the only primary micronutrient metal, the ratio of the equivalents of zinc to phosphorous in the zinc polyphosphate may be greater than 0.35:1, respectively. By way of further example, in one embodiment in which zinc is the only primary micronutrient metal, the ratio of the equivalents of zinc to phosphorous in the zinc polyphosphate may be greater than 0.375:1, respectively. By way of further example, in one embodiment in which zinc is the only primary micronutrient metal, the ratio of the equivalents of zinc to phosphorous in the zinc polyphosphate may be greater than 0.4:1, respectively. In general, however, the upper limit of zinc is the amount that would lead to the formation of the corresponding monohydrogen orthophosphate.

In another embodiment, the micronutrient metal polyphosphate composition comprises iron as the only primary micronutrient metal. In such embodiments, the ratio of the equivalents of iron to phosphorous in the iron polyphosphate may be greater than 0.12:1, respectively. By way of further example, the ratio of the equivalents of iron to phosphorous in the iron polyphosphate may be greater than 0.15:1, respectively. By way of further example, the ratio of the equivalents of iron to phosphorous in the iron polyphosphate may be greater than 0.2:1, respectively. By way of further example, in one embodiment in which iron is the only primary micronutrient metal, the ratio of the equivalents of iron to phosphorous in the iron polyphosphate may be greater than 0.25:1, respectively. By way of further example, in one embodiment in which iron is the only primary micronutrient metal, the ratio of the equivalents of iron to phosphorous in the iron polyphosphate may be greater than 0.3:1, respectively. By way of further example, in one embodiment in which iron is the only primary micronutrient metal, the ratio of the equivalents of iron to phosphorous in the iron polyphosphate may be greater than 0.35:1, respectively. In general, however, the upper limit of iron is the amount that would lead to the formation of the corresponding monohydrogen orthophosphate.

In another embodiment, the micronutrient metal polyphosphate composition comprises manganese as the only primary micronutrient metal. In such embodiments, the ratio of the equivalents of manganese to phosphorous in the iron polyphosphate may be greater than 0.2:1, respectively. By way of further example, in one embodiment in which manganese is the only primary micronutrient metal, the ratio of the equivalents of manganese to phosphorous in the manganese polyphosphate may be greater than 0.25:1, respectively. By way of further example, in one embodiment in which manganese is the only primary micronutrient metal, the ratio of the equivalents of manganese to phosphorous in the iron polyphosphate may be greater than 0.3:1, respectively. By way of further example, in one embodiment in which manganese is the only primary micronutrient metal, the ratio of the equivalents of manganese to phosphorous in the manganese polyphosphate may be greater than 0.35:1, respectively. By way of further example, in one embodiment in which manganese is the only primary micronutrient metal, the ratio of the equivalents of manganese to phosphorous in the manganese polyphosphate may be greater than 0.4:1, respectively. In general, however, the upper limit of manganese is the amount that would lead to the formation of the corresponding monohydrogen orthophosphate.

In another embodiment, the micronutrient metal polyphosphate composition comprises at least two of the primary micronutrients in micronutrient concentrations. For example, as illustrated in the following examples, the micronutrient metal polyphosphate may comprise a combination of primary micronutrients selected from among the following combinations: (i) zinc and manganese; (ii) zinc and iron; (iii) zinc, iron and manganese; (iv) zinc, iron, manganese and copper; and (v) iron, manganese and copper.

In one embodiment, the micronutrient metal polyphosphate composition comprises iron and manganese in micronutrient concentrations. For example, the ratio of the equivalents of iron and manganese (in combination) to phosphorous in the micronutrient metal polyphosphate may be greater than 0.12:1, respectively. By way of further example, the ratio of the equivalents of iron and manganese (in combination) to phosphorous in the micronutrient metal polyphosphate may be greater than 0.15:1, respectively. By way of further example, the ratio of the equivalents of iron and manganese (in combination) to phosphorous in the micronutrient metal polyphosphate may be greater than 0.2:1, respectively. By way of further example, the ratio of the equivalents of iron and manganese (in combination) to phosphorous in the micronutrient metal polyphosphate may be greater than 0.25:1, respectively. By way of further example, the ratio of the equivalents of iron and manganese (in combination) to phosphorous in the micronutrient metal polyphosphate may be greater than 0.3:1, respectively. By way of further example, the ratio of the equivalents of iron and manganese (in combination) to phosphorous in the micronutrient metal polyphosphate may be greater than 0.35:1, respectively. In general, however, the upper limit of each of these metals is the amount that would lead to the formation of the corresponding monohydrogen orthophosphate.

In one embodiment, the micronutrient metal polyphosphate composition comprises iron, manganese and copper in micronutrient concentrations. For example, the ratio of the equivalents of iron, manganese and copper (in combination) to phosphorous in the micronutrient metal polyphosphate may be greater than 0.15:1, respectively. By way of further example, the ratio of the equivalents of iron, manganese and copper (in combination) to phosphorous in the micronutrient metal polyphosphate may be greater than 0.2:1, respectively. By way of further example, the ratio of the equivalents of iron, manganese and copper (in combination) to phosphorous in the micronutrient metal polyphosphate may be greater than 0.25:1, respectively. By way of further example, the ratio of the equivalents of iron, manganese and copper (in combination) to phosphorous in the micronutrient metal polyphosphate may be greater than 0.3:1, respectively. By way of further example, the ratio of the equivalents of iron, manganese and copper (in combination) to phosphorous in the micronutrient metal polyphosphate may be greater than 0.35:1, respectively. In general, however, the upper limit of each of these metals is the amount that would lead to the formation of the corresponding monohydrogen orthophosphate.

In one embodiment, the micronutrient metal polyphosphate composition comprises zinc, iron, and manganese in micronutrient concentrations. For example, the ratio of the equivalents of zinc, iron, and manganese (in combination) to phosphorous in the micronutrient metal polyphosphate may be greater than 0.2:1, respectively. By way of further example, the ratio of the equivalents of zinc, iron, and manganese (in combination) to phosphorous in the micronutrient metal polyphosphate may be greater than 0.25:1, respectively. By way of further example, the ratio of the equivalents of zinc, iron, and manganese (in combination) to phosphorous in the micronutrient metal polyphosphate may be greater than 0.3:1, respectively. By way of further example, the ratio of the equivalents of zinc, iron, and manganese (in combination) to phosphorous in the micronutrient metal polyphosphate may be greater than 0.35:1, respectively. In general, however, the upper limit of each of these metals is the amount that would lead to the formation of the corresponding monohydrogen orthophosphate.

In one embodiment, the micronutrient metal polyphosphate composition comprises zinc, iron, manganese and copper in micronutrient concentrations. For example, the ratio of the equivalents of zinc, iron, manganese and copper (in combination) to phosphorous in the micronutrient metal polyphosphate may be greater than 0.23:1, respectively. By way of further example, the ratio of the equivalents of zinc, iron, manganese and copper (in combination) to phosphorous in the micronutrient metal polyphosphate may be greater than 0.25:1, respectively. By way of further example, the ratio of the equivalents of zinc, iron, manganese and copper (in combination) to phosphorous in the micronutrient metal polyphosphate may be greater than 0.3:1, respectively. By way of further example, the ratio of the equivalents of zinc, iron, manganese and copper (in combination) to phosphorous in the micronutrient metal polyphosphate may be greater than 0.35:1, respectively. In general, however, the upper limit of each of these metals is the amount that would lead to the formation of the corresponding monohydrogen orthophosphate.

More generally, in certain embodiments the ratio of the equivalents of the primary micronutrient metals (in combination) to phosphorous in the micronutrient metal polyphosphate will be greater than 0.23:1, respectively. For example, in one embodiment in which micronutrient metal polyphosphate comprises two or more primary micronutrient metals, the ratio of the equivalents of the primary micronutrient metals (in combination) to phosphorous in the micronutrient metal polyphosphate will be greater than 0.25:1, respectively. By way of further example, in one embodiment in which micronutrient metal polyphosphate comprises two or more primary micronutrient metals, the ratio of the equivalents of the primary micronutrient metals (in combination) to phosphorous in the micronutrient metal polyphosphate may be greater than 0.275:1, respectively. By way of further example, in one embodiment in which micronutrient metal polyphosphate comprises two or more primary micronutrient metals, the ratio of the equivalents of the primary micronutrient metals (in combination) to phosphorous in the micronutrient metal polyphosphate may be greater than 0.3:1, respectively. By way of further example, in one embodiment in which micronutrient metal polyphosphate comprises two or more primary micronutrient metals, the ratio of the equivalents of the primary micronutrient metals (in combination) to phosphorous in the micronutrient metal polyphosphate may be greater than 0.35:1, respectively. By way of further example, in one embodiment in which micronutrient metal polyphosphate comprises two or more primary micronutrient metals, the ratio of the equivalents of the primary micronutrient metals (in combination) to phosphorous in the micronutrient metal polyphosphate may be greater than 0.4:1, respectively. By way of further example, in one embodiment in which micronutrient metal polyphosphate comprises two or more primary micronutrient metals, the ratio of the equivalents of the primary micronutrient metals (in combination) to phosphorous in the micronutrient metal polyphosphate may be greater than 0.5:1, respectively. In general, however, the upper limit of each of these metals is the amount that would lead to the formation of the corresponding monohydrogen orthophosphate.

Depending upon their composition, certain of the micronutrient metal polyphosphates can be characterized by their X-ray diffraction reflections. For example, certain zinc polyphosphate compositions of the present invention, with or without iron, manganese, copper, boron or molybdenum, may be characterized by having an X-ray diffraction reflection at one or more of the following positions: 8.72 ($\pm$0.09), 6.88 ($\pm$0.07), 4.834 ($\pm$0.025), 4.710 ($\pm$0.025), 4.24 ($\pm$0.02), 4.20 ($\pm$0.02), 3.969($\pm$0.0175), 3.68 ($\pm$0.01), 3.58 ($\pm$0.01), 3.38 ($\pm$0.01), 2.848 ($\pm$0.009), 2.585($\pm$0.007), 2.430 ($\pm$0.007), 2.071 (±0.005), 1.934 (±0.004), 1.80 (±0.003), 1.721 (±0.0029), 1.667 (±0.0028), 1.660 (±0.0027), 1.620 (±0.0027), 1.615 (±0.0026), 1.594 (±0.0025), and 1.564 (±0.0024) Å. In one embodiment, zinc polyphosphate compositions of the present invention, with or without iron, manganese, copper, boron or molybdenum, may be characterized by having an X-ray diffraction reflection at two or more of said positions. In another embodiment, zinc polyphosphate compositions of the present invention, with or without iron, manganese, copper, boron or molybdenum, may be characterized by having an X-ray diffraction reflection at three or more of said positions. In another embodiment, zinc polyphosphate compositions of the present invention, with or without iron, manganese, copper, boron or molybdenum, may be characterized by having an X-ray diffraction reflection at four or more of said positions. In another embodiment, zinc polyphosphate compositions of the present invention, with or without iron, manganese, copper, boron or molybdenum, may be characterized by having an X-ray diffraction reflection at five or more of said positions.

Similarly, certain iron, manganese or copper polyphosphate composition of the present invention may be characterized by having an X-ray diffraction reflection at one or more of the following positions: 8.17(±0.09), 5.98 (±0.03), 5.16 (±0.03), 4.82 (±0.025), 4.52 (±0.025), 4.27(±0.02), 4.16(±0.02), 3.48 (±0.01), 3.44 (±0.01), 2.87 (±0.009), 2.85 (±0.009), 2.59 (±0.007), 2.57 (±0.007), 2.52 (±0.007), 2.15 (±0.005), 1.96 (±0.004), and 1.75 (±0.003) Å. In one embodiment, certain iron, manganese or copper polyphosphate composition of the present invention may be characterized by having an X-ray diffraction reflection at two or more of said positions. In one embodiment, certain iron, manganese or copper polyphosphate composition of the present invention may be characterized by having an X-ray diffraction reflection at three or more of said positions. In one embodiment, certain iron, manganese or copper polyphosphate composition of the present invention may be characterized by having an X-ray diffraction reflection at four or more of said positions. In one embodiment, certain iron, manganese or copper polyphosphate composition of the present invention may be characterized by having an X-ray diffraction reflection at five or more of said positions.

As described elsewhere herein, the micronutrient metal polyphosphate is neutralized post-polymerization for improved material handling characteristics. In general, it is preferred that the equilibrium pH of an aqueous mixture of ten parts by weight of water at neutral pH and one part by weight of the neutralized micronutrient metal polyphosphate be at least pH 2. More preferably, the equilibrium pH of an aqueous mixture of ten parts by weight of water at neutral pH and one part by weight of the neutralized micronutrient metal polyphosphate be at least pH 3. Still more preferably, the equilibrium pH of an aqueous mixture of ten parts by weight of water at neutral pH and one part by weight of the neutralized micronutrient metal polyphosphate be at least pH 4. Still more preferably, the equilibrium pH of an aqueous mixture of ten parts by weight of water at neutral pH and one part by weight of the neutralized micronutrient metal polyphosphate be at least pH 5. In certain embodiments, the equilibrium pH of an aqueous mixture of ten parts by weight of water at neutral pH and one part by weight of the neutralized micronutrient metal polyphosphate be at least pH 6. For example, in one embodiment, the equilibrium pH of an aqueous mixture of ten parts by weight of water at neutral pH and one part by weight of the neutralized micronutrient metal polyphosphate will be in the range of pH 5-8.

In general, the micronutrient metal polyphosphate is preferably a solid, free-flowing particulate material. Particle size is not narrowly critical but is generally preferably in the range of about 80 mesh to about 150 mesh. Still preferably the particle size is in the range of 150 mesh to 300 mesh. Still preferably the particle size is in less than 300 mesh.

Cobalt Micronutrient Fertilizers

In one embodiment, the micronutrient fertilizer of the present invention comprises cobalt as a micronutrient. In general, fertilizers containing cobalt as a micronutrient contain at least 0.1 wt. % cobalt. Typically, fertilizers containing cobalt as a micronutrient contain at least 1 wt. % cobalt. In certain embodiments, fertilizers containing cobalt as a micronutrient contain at least 2 wt. % cobalt. In other embodiments, fertilizers containing cobalt as a micronutrient contain at least 3 wt. % cobalt. For example, in one embodiment, the fertilizers containing cobalt as a micronutrient contain 1-5 wt. % cobalt. In each of these embodiments, the cobalt micronutrient fertilizer may optionally contain one or more of the other primary nutrients described herein, one or more of the secondary micronutrients described herein, other macronutrients or micronutrients, or yet other compositions that may contribute to the nutritional, material or handling characteristics of the fertilizer.

Cobalt micronutrient fertilizers compositions of the present invention contain, as a component thereof, a micronutrient metal polyphosphate composition of the present invention, containing cobalt as a micronutrient. Such cobalt micronutrient fertilizer compositions may optionally contain other components that contribute to the nutritional, material handling, or other characteristics of the fertilizer. For example, the cobalt micronutrient fertilizer may contain a water-soluble N-P-K macronutrient fertilizer that has been blended or otherwise combined with the cobalt polyphosphate composition. By way of further example, the cobalt micronutrient fertilizer may contain water-soluble or even water-insoluble micronutrient compounds that has been blended or otherwise combined with the cobalt polyphosphate composition. By way of further example, the cobalt micronutrient fertilizer may contain organic materials like plant residues that have been blended or otherwise combined with the cobalt polyphosphate composition to improve the material handling characteristics of the cobalt micronutrient fertilizer.

Cobalt polyphosphate compositions may be prepared by combining a cobalt source material, phosphoric acid (preferably containing no more than 60% $P_2O_5$), and, optionally, one or more additional materials to form a reaction mixture and reacting the components of the mixture to form the cobalt polyphosphate. The optional additional materials include, for example, one or more of the other primary micronutrients described herein, one or more of the secondary micronutrients described herein and other macronutrient or micronutrient compositions desirably included in the polyphosphate composition. The cobalt source material may be any source of cobalt that is compatible with the polymerization process of the present invention. Such sources include, for example, cobaltous oxide cobaltic oxide, cobalt sulfate, and cobalt chloride.

Chromium Micronutrient Fertilizers

In one embodiment, the micronutrient fertilizer of the present invention comprises chromium as a micronutrient. In general, fertilizers containing chromium as a micronutrient contain at least 0.1 wt. % chromium. Typically, fertilizers containing chromium as a micronutrient contain at least 1 wt. % chromium. In certain embodiments, fertilizers containing chromium as a micronutrient contain at least 2 wt. % chromium. In certain embodiments, fertilizers containing chromium as a micronutrient contain at least 3 wt. % chromium. In other embodiments, fertilizers containing chromium as a micronutrient contain at least 5 wt. % chromium. For example, in one embodiment, the fertilizers containing chromium as a micronutrient contain 3-7 wt. % chromium. In each of these embodiments, the chromium micronutrient fertilizer may optionally contain one or more of the other primary nutrients described herein, one or more of the secondary micronutrients described herein, other macronutrients or micronutrients, or yet other compositions that may contribute to the nutritional, material or handling characteristics of the fertilizer.

Chromium micronutrient fertilizers compositions of the present invention contain, as a component thereof, a micronutrient metal polyphosphate composition of the present invention, containing chromium as a micronutrient. Such chromium micronutrient fertilizer compositions may optionally contain other components that contribute to the nutritional, material handling, or other characteristics of the fertilizer. For example, the chromium micronutrient fertilizer may contain a water-soluble N-P-K macronutrient fertilizer that has been blended or otherwise combined with the chromium polyphosphate composition. By way of further example, the chromium micronutrient fertilizer may contain water-soluble or even water-insoluble micronutrient compounds that has been blended or otherwise combined with the chromium polyphosphate composition. By way of further example, the chromium micronutrient fertilizer may contain organic materials like plant residues that have been blended or otherwise combined with the chromium polyphosphate composition to improve the material handling characteristics of the chromium micronutrient fertilizer.

Chromium polyphosphate compositions may be prepared by combining a chromium source material, phosphoric acid (preferably containing no more than 60% $P_2O_5$), and, optionally, one or more additional materials to form a reaction mixture and reacting the components of the mixture to form the chromium polyphosphate. The optional additional materials include, for example, one or more of the other primary micronutrients described herein, one or more of the secondary micronutrients described herein and other macronutrient or micronutrient compositions desirably included in the polyphosphate composition. The chromium source material may be any source of chromium that is compatible with the polymerization process of the present invention. Such sources include, for example, chromium (III) oxides, chromium (VI) oxide, chromium(III) sulfate, chromium(III) chloride, and dichromate salts.

Copper Micronutrient Fertilizers

In one embodiment, the micronutrient fertilizer of the present invention comprises copper as a micronutrient. In general, fertilizers containing copper as a micronutrient contain at least 0.1 wt. % copper. Typically, fertilizers containing copper as a micronutrient contain at least 1 wt. % copper. In certain embodiments, fertilizers containing copper as a micronutrient contain at least 5 wt. % copper. In other embodiments, fertilizers containing copper as a micronutrient contain at least 10 wt. % copper. For example, in one embodiment, the fertilizers containing copper as a micronutrient contain 14-20 wt. % copper. In each of these embodiments, the copper micronutrient fertilizer may optionally contain one or more of the other primary nutrients described herein, one or more of the secondary micronutrients described herein, other macronutrients or micronutrients, or yet other compositions that may contribute to the nutritional, material or handling characteristics of the fertilizer.

Copper micronutrient fertilizers compositions of the present invention contain, as a component thereof, a micronutrient metal polyphosphate composition of the present invention, containing copper as a micronutrient. Such copper micronutrient fertilizer compositions may optionally contain other components that contribute to the nutritional, material handling, or other characteristics of the fertilizer. For example, the copper micronutrient fertilizer may contain a water-soluble N-P-K macronutrient fertilizer that has been blended or otherwise combined with the copper polyphosphate composition. By way of further example, the copper micronutrient fertilizer may contain water-soluble or even water-insoluble micronutrient compounds that has been blended or otherwise combined with the copper polyphosphate composition. By way of further example, the copper micronutrient fertilizer may contain organic materials like plant residues that have been blended or otherwise combined with the copper polyphosphate composition to improve the material handling characteristics of the copper micronutrient fertilizer.

Copper polyphosphate compositions may be prepared by combining a copper source material, phosphoric acid (preferably containing no more than 60% $P_2O_5$), and, optionally, one or more additional materials to form a reaction mixture and reacting the components of the mixture to form the copper polyphosphate. The optional additional materials include, for example, one or more of the other primary micronutrients described herein, one or more of the secondary micronutrients described herein and other macronutrient or micronutrient compositions desirably included in the polyphosphate composition. The copper source material may be any source of copper that is compatible with the polymerization process of the present invention. Such sources include, for example, cupric carbonate, cupric hydroxide, cupric hydroxide carbonate, cupric sulfate, cupric chloride, and cupric oxide.

Manganese Micronutrient Fertilizers

In one embodiment, the micronutrient fertilizer of the present invention comprises manganese as a micronutrient. In general, fertilizers containing manganese as a micronutrient contain at least 0.1 wt. % manganese. Typically, fertilizers containing manganese as a micronutrient contain at least 1 wt. % manganese. In certain embodiments, fertilizers containing manganese as a micronutrient contain at least 5 wt. % manganese. In other embodiments, fertilizers containing manganese as a micronutrient contain at least 8 wt. % manganese. For example, in one embodiment, the fertilizers containing manganese as a micronutrient contain 10-20 wt. % manganese. In each of these embodiments, the manganese micronutrient fertilizer may optionally contain one or more of the other primary nutrients described herein, one or more of the secondary micronutrients described herein, other macronutrients or micronutrients, or yet other compositions that may contribute to the nutritional, material or handling characteristics of the fertilizer.

Manganese micronutrient fertilizers compositions of the present invention contain, as a component thereof, a micronutrient metal polyphosphate composition of the present invention, containing manganese as a micronutrient. Such manganese micronutrient fertilizer compositions may optionally contain other components that contribute to the nutritional, material handling, or other characteristics of the fertilizer. For example, the manganese micronutrient fertilizer may contain a water-soluble N-P-K macronutrient fertilizer that has been blended or otherwise combined with the manganese polyphosphate composition. By way of further example, the manganese micronutrient fertilizer may contain water-soluble or even water-insoluble micronutrient compounds that has been blended or otherwise combined with the manganese polyphosphate composition. By way of further example, the manganese micronutrient fertilizer may contain organic materials like plant residues that have been blended or otherwise combined with the manganese polyphosphate composition to improve the material handling characteristics of the manganese micronutrient fertilizer.

Manganese polyphosphate compositions may be prepared by combining a manganese source material, phosphoric acid (preferably containing no more than 60% $P_2O_5$), and, optionally, one or more additional materials to form a reaction mixture and reacting the components of the mixture to form the manganese polyphosphate. The optional additional materials include, for example, one or more of the other primary micronutrients described herein, one or more of the secondary micronutrients described herein and other macronutrient or micronutrient compositions desirably included in the polyphosphate composition. The manganese source material may be any source of manganese that is compatible with the polymerization process of the present invention. Such sources include, for example, manganous carbonate, manganous oxide, manganese dioxide, manganous sulfate, and manganous chloride.

Zinc Micronutrient Fertilizers

In one embodiment, the micronutrient fertilizer of the present invention comprises zinc as a micronutrient. In general, fertilizers containing zinc as a micronutrient contain at least 0.1 wt. % zinc. Typically, fertilizers containing zinc as a micronutrient contain at least 1 wt. % zinc. In certain embodiments, fertilizers containing zinc as a micronutrient contain at least 10 wt. % zinc. In other embodiments, fertilizers containing zinc as a micronutrient contain 20-30 wt. % zinc. For example, in one embodiment, the fertilizers containing zinc as a micronutrient contain 20-25 wt. % zinc. By way of further example, in one embodiment, the fertilizers containing zinc as a micronutrient contain 24-30 wt. % zinc. In each of these embodiments, the zinc micronutrient fertilizer may optionally contain one or more of the other primary nutrients described herein, one or more of the secondary micronutrients described herein, other macronutrients or micronutrients, or yet other compositions that may contribute to the nutritional, material or handling characteristics of the fertilizer.

Zinc micronutrient fertilizers compositions of the present invention contain, as a component thereof, a micronutrient metal polyphosphate composition of the present invention, containing zinc as a micronutrient. Such zinc micronutrient fertilizer compositions may optionally contain other components that contribute to the nutritional, material handling, or other characteristics of the fertilizer. For example, the zinc micronutrient fertilizer may contain a water-soluble N-P-K macronutrient fertilizer that has been blended or otherwise combined with the zinc polyphosphate composition. By way of further example, the zinc micronutrient fertilizer may contain water-soluble or even water-insoluble micronutrient compounds that has been blended or otherwise combined with the zinc polyphosphate composition. By way of further example, the zinc micronutrient fertilizer may contain organic materials like plant residues that have been blended or otherwise combined with the zinc polyphosphate composition to improve the material handling characteristics of the zinc micronutrient fertilizer.

Zinc polyphosphate compositions may be prepared by combining a zinc source material, phosphoric acid (preferably containing no more than 60% $P_2O_5$), and, optionally, one or more additional materials to form a reaction mixture and reacting the components of the mixture to form the zinc polyphosphate. The optional additional materials include, for example, one or more of the other primary micronutrients described herein, one or more of the secondary micronutrients described herein and other macronutrient or micronutrient compositions desirably included in the polyphosphate composition. The zinc source material may be any source of zinc that is compatible with the polymerization process of the present invention. Such sources include, for example, zinc oxide, zinc metal, zinc ash, zinc sulfate, zinc carbonate and zinc chloride.

Iron Micronutrient Fertilizers

In one embodiment, the micronutrient fertilizer of the present invention comprises iron as a micronutrient. In general, fertilizers containing iron as a micronutrient contain at least 0.1 wt. % iron. Typically, fertilizers containing iron as a micronutrient contain at least 1 wt. % iron. In certain embodiments, fertilizers containing iron as a micronutrient contain at least 3 wt. % iron. In other embodiments, fertilizers containing iron as a micronutrient contain at least 4 wt. % iron. For example, in one embodiment, the fertilizers containing iron as a micronutrient contain 5-15 wt. % iron. In each of these embodiments, the iron micronutrient fertilizer may optionally contain one or more of the other primary nutrients described herein, one or more of the secondary micronutrients described herein, other macronutrients or micronutrients, or yet other compositions that may contribute to the nutritional, material or handling characteristics of the fertilizer.

Iron micronutrient fertilizers compositions of the present invention contain, as a component thereof, a micronutrient metal polyphosphate composition of the present invention, containing iron as a micronutrient. Such iron micronutrient fertilizer compositions may optionally contain other components that contribute to the nutritional, material handling, or other characteristics of the fertilizer. For example, the iron micronutrient fertilizer may contain a water-soluble N-P-K macronutrient fertilizer that has been blended or otherwise combined with the iron polyphosphate composition. By way of further example, the iron micronutrient fertilizer may contain water-soluble or even water-insoluble micronutrient compounds that has been blended or otherwise combined with the iron polyphosphate composition. By way of further example, the iron micronutrient fertilizer may contain organic materials like plant residues that have been blended or otherwise combined with the iron polyphosphate composition to improve the material handling characteristics of the iron micronutrient fertilizer.

Iron polyphosphate compositions may be prepared by combining an iron source material, phosphoric acid (preferably containing no more than 60% $P_2O_5$), and, optionally, one or more additional materials to form a reaction mixture and reacting the components of the mixture to form the iron polyphosphate. The optional additional materials include, for example, one or more of the other primary micronutrients described herein, one or more of the secondary micronutrients described herein and other macronutrient or micronutrient compositions desirably included in the polyphosphate composition. The iron source material may be any source of iron that is compatible with the polymerization process of the present invention. Such sources include, for example, goethite, hematite iron hydroxide, ferrous oxide, ferric sulfate, ferrous sulfate, ferric chloride, and ferric sulfate.

Fertilizers Containing Two or More Micronutrients

As noted, the micronutrient metal polyphosphate may contain two or more primary micronutrients, one or more primary micronutrients and one or more secondary micronutrients. In general fertilizers that contain two or more primary micronutrients contain at least 0.1 wt. % primary nutrients, more typically at least 1 wt. % of each of the primary micronutrients. Additionally, the primary micronutrient metals may be present in any of the concentrations recited herein in connection with the cobalt micronutrient fertilizers, chromium micronutrient fertilizers, copper micronutrient fertilizers, iron micronutrient fertilizers, manganese micronutrient fertilizers, and zinc micronutrient fertilizers. For example, the fertilizer may contain 1-5 wt. % cobalt, 1-20 wt. % copper, 1-7 wt. % chromium, 1-15 wt. % iron, 1-20 wt. % manganese, and/or 1-30 wt. % zinc. In addition, the fertilizer may optionally comprise one or more of the secondary micronutrients such as one or more of boron, molybdenum and selenium. By way of further example, in one such composition contains less than 30 wt. % of boron, chromium, cobalt, copper, iodine, iron, manganese, molybdenum, selenium, sulfur and zinc, in combination.

For certain applications, it is preferred that the micronutrient metal polyphosphate contain a combination of primary micronutrient metals. In one such embodiment, the micronutrient metal polyphosphate contains zinc, iron, and manganese as micronutrient metals. For example, in one such embodiment, the zinc, iron and manganese, in combination, constitute at least 5 wt. % of the micronutrient metal polyphosphate composition. By way of further example, in one such embodiment, the zinc, iron and manganese, in combination, constitute at least 12 wt. % of the micronutrient metal polyphosphate composition.

For other applications it is preferred that the micronutrient metal polyphosphate contain zinc, iron, manganese and copper as micronutrient metals. For example, in one such embodiment, the zinc, iron, manganese, and copper, in combination, constitute at least 10 wt. % of the micronutrient metal polyphosphate composition. By way of further example, in one such embodiment, the zinc, iron, manganese, and copper, in combination, constitute at least 14 wt. % of the micronutrient metal polyphosphate composition. By way of further example, in one such embodiment, the zinc, iron, manganese, and copper, in combination, constitute about 15-25 wt. % of the micronutrient metal polyphosphate composition. Individually, zinc may constitute about 5-15 wt %, iron may constitute about 3-5 wt. %, manganese may constitute about 1-2 wt. % and copper may constitute about 0.5-1 wt. % of the composition.

For other applications it is preferred that the micronutrient metal polyphosphate contain iron and manganese as micronutrient metals. For example, in one such embodiment, the iron and manganese, in combination, constitute at least 5 wt. % of the micronutrient metal polyphosphate composition. By way of further example, in one such embodiment, the iron and manganese, in combination, constitute at least 10 wt. % of the micronutrient metal polyphosphate composition. Individually, for example, iron may constitute about 3-10 wt % and manganese may constitute about 3-10 wt. % of the composition.

For other applications it is preferred that the micronutrient metal polyphosphate contain iron, manganese and copper as micronutrient metals. For example, in one such embodiment, the iron, manganese, and copper, in combination, constitute at least 6 wt. % of the micronutrient metal polyphosphate composition. By way of further example, in one such embodiment, the iron, manganese, and copper, in combination, constitute at least 12 wt. % of the micronutrient metal polyphosphate composition.

For other applications it is preferred that the micronutrient metal polyphosphate contain one or more of the primary micronutrients and one or more of the secondary micronutrients disclosed herein. For example, in one embodiment the micronutrient metal polyphosphate may contain at least 2 wt. % zinc and at least 0.1 wt. % boron. By way of further example, in one embodiment the micronutrient metal polyphosphate may contain at least 22 wt. % zinc and at least 2 wt. % boron.

For other applications it is preferred that the micronutrient metal polyphosphate contain zinc, iron, manganese and molybdenum as micronutrients. For example, in one such embodiment, the zinc, iron, and manganese, in combination, constitute at least 5 wt. % and molybdenum constitutes at least 0.01 wt. % of the micronutrient metal polyphosphate composition. By way of further example, in one such embodiment, the zinc, iron, and manganese, in combination, constitute at least 13 wt. % and molybdenum constitutes at least 0.3 wt. % of the micronutrient metal polyphosphate composition.

For other applications it is preferred that the micronutrient metal polyphosphate contain zinc, iron, manganese, copper and boron as micronutrients. For example, in one such embodiment, the zinc, iron, copper, and manganese, in combination, constitute at least 5 wt. % and boron constitutes at least 0.05 wt. % of the micronutrient metal polyphosphate composition. By way of further example, in one such embodiment, the zinc, iron, copper, and manganese, in combination, constitute at least 14 wt. % and boron constitutes at least 0.9 wt. % of the micronutrient metal polyphosphate composition.

Methods of Producing Polyphosphate Compositions

In an illustrative embodiment, the polyphosphate compositions are produced by heating alkaline earth metal containing compounds such as oxides, carbonates, hydroxides, phosphates, sulfates or combinations thereof, with phosphoric acid, and optionally nutrient compounds and optionally water. In an embodiment, heating alkaline earth metal containing compounds such as metal oxides, metal carbonates, or combinations thereof, with phosphoric acid, and optionally water, produces polyphosphates. In an alternative embodiment, the polyphosphate compositions are produced by pre-heating phosphoric acid and optionally water to between about 60° C. and 140° C., or to between 60° C. and 200° C. and then combining alkaline earth metal containing compounds such as oxides, carbonates, hydroxides or combinations thereof and optionally nutrient compounds. In another alternative embodiment, the polyphosphate compositions are produced by heating alkaline earth metal containing compounds such as oxides, carbonates, hydroxides or combinations thereof, with phosphoric acid, and optionally water then adding optionally nutrient compounds and continuing the heating. In an embodiment, the polymerization step does not include a condensing agent such as urea. In an embodiment the heating is not continued till the stage when the polyphosphate becomes solid. In this embodiment, heating is done only till the stage that the polyphosphate remains a liquid.

After the alkaline earth metal compound is added to the phosphoric acid and optionally water, optionally sulfuric acid, boric acid, borax, molybdic acid or selenic acid or their salts may be added and the mixture may be heated to between about 70° C. and about 160° C., alternatively between about 80° C. and about 120° C., alternatively between about 80° C. and about 200° C., alternatively to about 105° C., and alternatively to about 110° C. Then, the nutrient ion compound and optionally sulfuric acid. boric acid, borax, molybdic acid or selenic acid or a salt thereof may be added to the mixture of alkaline earth metal compound and phosphoric acid. Contemporaneously with the addition of nutrient ion compound, water is preferably added to the mixture. The mixture of the alkaline earth metal compound, phosphoric acid, optionally nutrient ion compound, and water is preferably heated to between about 70° C. and about 160° C., alternatively between about 80° C. and about 120° C., alternatively between about 80° C. and about 200° C., alternatively to about 105° C., alternatively to about 110° C., and polymerization occurs.

Preferably, during the polymerization stage, for any alkaline earth metal ion $M^{2+}$, the molar ratio of phosphorous to metal is greater than about 1.5:1. Thus, for producing a calcium polyphosphate, the molar ratio of phosphorous to calcium taken for polymerization is more than 2:1, preferably about 2.2:1, or preferably about 2.5:1, or preferably about 3:1. Alternately, for producing a calcium-magnesium polyphosphate, the molar ratio of phosphorous to calcium and magnesium (in combination), taken for polymerization is more than 2:1, preferably about 2.7:1. Alternately, for producing a calcium-magnesium polyphosphate, the molar ratio of phosphorous to calcium and magnesium (in combination), taken for polymerization is more than 2:1, preferably about 3:1

In an alternative embodiment, for any optional nutrient metal ion $M^{n+}$, where n+ is the valance of the metal ion, excess phosphoric acid has to be taken where the molar ratio of phosphorous to metal is greater than about n:1. For example, if the metal ion has a valence of +3, the molar ratio of phosphorous to the metal is greater than 3:1 (e.g., 5 moles or more of phosphorous for every mole of metal).

The polymerization step may be terminated when the product is soluble in about 6.9 wt % citric acid, two weight percent citric acid or 0.1 normal hydrochloric acid. Without wishing to be bound by the theory, the product is preferably heated until just before it becomes insoluble in 0.1 wt. % citric acid or 0.01 normal hydrochloric acid, as over-polymerization may cause insolubilization in acid and reduce the availability of the nutrients to plants.

The polyphosphate composition product may be poured out of the reactor and cooled. When the product temperature reaches below about 90° C., water may be added to increase the product's fluidity; additionally, the polyphosphate composition product may be stirred to further enhance and/or maintain fluidity. The polyphosphate composition product may also be neutralized with a neutralizing base, dried and ground to a powder.

Preferable neutralizing bases include magnesium oxides, magnesium carbonates, calcium oxides, calcium carbonates, ammonium hydroxides, ammonium carbonates, sodium hydroxides, sodium carbonates, potassium hydroxides, potassium carbonates and combinations thereof. Bases are mixed with water prior to their use for neutralizing the polyphosphate. Without wishing to be bound by the theory, addition of water to the base reduces lumping of the neutralized polyphosphate. Preferably, the polyphosphate composition product is ground to an average particle size of less than about 200 mesh, alternatively less than about 150 mesh, alternatively less than about 100 mesh.

Having described the invention in detail, it will be apparent that modifications and variations are possible without departing the scope of the invention defined in the appended claims. The following non-limiting examples are provided to further illustrate the present invention and those of skill in the art should, in light of the present disclosure, appreciate that many changes can be made in the specific embodiments that are disclosed and still obtain a like or similar result without departing from the spirit and scope of the invention.

EXAMPLES

The following methods were used to characterize the materials in the examples below:

Total cation content: 50 milligrams of sample was dissolved in 3 milliliters of concentrated sulphuric acid by heating for a few minutes. The solution was diluted and filtered. Cations in solution were analysed by atomic absorption spectroscopy Maximum adsorption by urea/DAP/MAP/SSP: A weighed amount of polyphosphate fertilizer was mixed with a weighed amount of urea/DAP/MAP/SSP granules. This was mixed thoroughly and then sieved through 80 mesh BS. The amount of polyphosphate that came out of the sieve was weighed.

Total phosphorus content: 50 milligrams of sample was fused with sodium hydroxide in a nickel crucible and taken into solution with water. Phosphorus was determined by the molybdenum blue color method. (Soil Chemical Analysis, ML Jackson, 1973, Prentice Hall, New Delhi).

Number Average Chain Length: The titrimetric method reported by Van Wazer was followed for the determination of number average chain length excluding ortho using the equation: $[\{2(\text{total P-orthophosphate P})\}/\{\text{endgroup P-orthophosphate P}\}]$ (Van Wazer, J. R. 1966. Phosphorus and its compounds, Vol. 1. Interscience, New York, N.Y; Ray S K, Chandra P K, Varadachari C and Ghosh K (1998)). For removing micronutrient metal cation interferences prior to titrimetric determination of polyphosphate chain length, the sample was dissolved in 0.1 N HCl and stirred with a cation exchange resin in H-form. The supernatant solution which was free of cations (except hydrogen) was titrated for polyphosphate chain length by the method of Van Wazer J. R. 1966 referred above).

For solubilities, mesh size of less than 150 mesh was used.

Water solubility: 50 milligrams of sample was placed in a conical flask and 50 milliliters of water was added to it. This was placed in a rotary shaker for 30 minutes, then filtered washed and made to volume. Cations in solution were analysed by atomic absorption spectroscopy. Amount of cation solubilized was expressed as a percentage of total cation determined as described above.

0.1 N HCl solubility: Solubility of the samples in 0.1 N HCl was determined as described above for citrate solubility.

Citrate solubility: 25 milligrams of samples was placed in a conical flask and 50 milliliters of 0.1 wt. %, 0.2 wt. % citric acid, 2 wt % citric acid or 6.9 wt % citric acid was added to it. It was placed in a rotary shaker for 20, 30 minutes or 60 minutes. It was then filtered washed and made to volume. Cations in solution were determined as described in the paragraph above. Solubilities in citrate are expressed as a percentage of that dissolved by 0.1N HCl.

DTPA solubility: Solubility of the samples in 0.005 M DTPA was determined as described above for citrate solubility. Solubilities in DTPA are expressed as a percentage of that dissolved by 0.1 N HCl.

EDTA solubility: Solubility of the samples in 0.005 M EDTA was determined as described above for citrate solubility. Solubilities in citrate are expressed as a percentage of that dissolved by 0.1 N HCl.

0.01N HCl solubility: Solubility of the samples in 0.01N HCl was determined as described above for citrate solubility. Solubilities in citrate are expressed as a percentage of that dissolved by 0.1 N HCl.

pH: pH of the fertilizers was recorded on a pH meter in a stirred suspension containing 1 gram of fertilizer powder in 10 milliliters water.

X-ray diffraction: XRD of the powdered sample was recorded in a X-ray diffractometer using Cu K$_a$ radiation at a scan rate of 2° 2 theta per minute.

Example 1

Zinc Fertilizer Coated on Urea

A. Production of Zinc Fertilizer

The fertilizer was produced from phosphoric acid (58.4% $P_2O_5$) and zinc oxide (50% Zn, 6.8% Fe, 6% Mg) in the molar ratio Zn:P=1:2.5. Commercial grade phosphoric acid (58.4% $P_2O_5$), 348 grams, was placed in a borosilicate beaker. In another beaker, 600 milliliters of water was taken and to it 150 grams of commercial grade zinc oxide (50% Zn) was added and stirred to form a slurry. The phosphoric acid was heated in an oil bath till its temperature reached 100° C. Then the slurry of zinc oxide was added to the phosphoric acid with stirring. The reaction was exothermic, and the temperature was raised to about 70° C. due to exothermic heat of the reaction. The beaker was further heated with stirring for about 20 minutes until the temperature of the liquid was 103° C. The beaker was then taken out of the heating unit and allowed to cool to around 90° C. Then a slurry of 105 grams of magnesium oxide (54% Mg) in 700 milliliters of water was added to it with stirring whereupon a white suspension was formed. This was mixed well in a blender and dried in a tray drier at 70° C. The dried material was powdered in a pulverizer to pass through 150 mesh.

The product included 11.2 weight percent zinc, 8.4 weight percent magnesium, 1.5 weight percent iron and 13.2 weight percent phosphorous. It had a pH of 5.4. The ratio of equivalent of Zn to equivalent of P was 0.27. In 2 weight percent citric acid the product released 96.8% of total zinc and 94% of total magnesium. In 0.005 molar DTPA the product released 96.1% of total zinc and 92.2% of total magnesium with respect to the total in 0.1 N HCl. In water 0.32% of total Zn, 4.76% of total magnesium and 7.9% of total P was solubilized. Dissolution in weakly acidic solution of pH 4 was 0.69% of total zinc and 4.7% of total magnesium. In a weakly alkaline solution, 0.46% of total zinc and 4.62% of total magnesium was dissolved. In 0.02M EDTA at pH 4.65, 95.8% of total Zn and 94.8% of total magnesium was solubilized. In 1N ammonium citrate at pH 8.5, 98.5% of total Zn and 96.3% of total magnesium was solubilized. X-ray diffraction diagram for the product shows peaks at 26.5, 20.75, 9.61, 9.096, 6.7, 6.37, 5.857, 5.422, 4.736, 4.536, 4.287, 3.91, 3.597, 3.496, 3.405, 3.244, 3.195, 3.167, 3.091, 2.975, 2.855, 2.643, 2.537, 2.434, 2.416, 2.373, 2.321, 2.265, 2.218, 2.148, 2.076, 2.033, 1.982, 1.964, 1.93, 1.92, 1.8325, 1.7991, 1.753, 1.6198, 1.5932, 1.5483 Å.

B. Coating on Urea 100 grams of urea granules (1-3 mm, 46% N) was weighed into a dry glass jar and 4 grams of the zinc fertilizer (of 150 mesh size) was added to it. It was shaken by hand to mix the contents thoroughly. The zinc fertilizer adhered to the urea and did not sediment at the bottom. The product mainly contained 0.43 weight percent zinc, 0.51 weight percent phosphorus, 0.32 weight percent magnesium and 44.2 weight percent nitrogen. When the urea was added to water, the zinc fertilizer particles immediately dispersed and urea dissolved. This forms a convenient method of applying the zinc fertilizer in the field. It also enriches the urea with micronutrient.

A maximum of 4.5 grams of this zinc fertilizer can be coated on 100 grams of urea.

Example 2

Zinc Fertilizer Coated on MAP (Mono Ammonium Phosphate)

A. Production of Zinc Fertilizer

The fertilizer of example 1 was used.

B. Coating on MAP (Method I)

100 grams of MAP granules (2-4 mm, 22.7% P, 11% N) was weighed into a dry glass jar and 1.5 grams of the zinc fertilizer (of 150 mesh size) was added to it. It was shaken by hand to mix the contents thoroughly. The product mainly contained 0.16 weight percent zinc, 22.6 weight percent phosphorus, 0.12 weight percent magnesium and 10.8 weight percent nitrogen. When the product was added to water, the zinc fertilizer particles immediately dispersed. This forms a convenient method of applying the zinc fertilizer in the field. It also enriches the MAP with micronutrient.

A maximum of 1.8 grams of this zinc fertilizer can be coated on 100 grams of MAP.

C. Coating on MAP (Method II)

100 grams of MAP granules (2-4 mm) was weighed into a tray and 20 grams of the zinc fertilizer (of 150 mesh size) was added to it. It was moistened with 10 milliliters water and dried with a hot air blower (at 60° C.) with constant mixing of the mass. The zinc fertilizer coated on to the surface of MAP. The product contained 1.87 weight percent zinc, 1.4 weight percent magnesium, 21.1 weight percent phosphorus and 9.2 weight percent nitrogen. When the product was added to water, the zinc fertilizer particles dispersed in about 30 minutes. This forms a convenient method of applying the zinc fertilizer in the field. It also enriches the MAP with micronutrient.

Example 3

Zinc Fertilizer Coated on DAP

A. Production of Zinc Fertilizer

The fertilizer of example 1 was used.

B. Coating on DAP (Method I)

100 grams of DAP granules (1-4 mm, 18% N, 17.9% P) was weighed into a dry glass jar and 3.5 grams of the zinc fertilizer (of 150 mesh size) was added to it. It was shaken by hand to mix the contents thoroughly. The zinc fertilizer adhered to the DAP and did not sediment at the bottom. The product contained 0.38 weight percent zinc, 0.28 weight percent magnesium, 17.7 weight percent phosphorus and 17.4 weight percent nitrogen. When the DAP was added to water, the zinc fertilizer particles immediately dispersed and DAP dissolved. This forms a convenient method of applying the zinc fertilizer in the field. It also enriches the DAP with micronutrient.

A maximum of 4 grams of this zinc fertilizer can be coated on 100 grams of DAP.

C. Coating on DAP (Method II)

100 grams of DAP granules (as described in B above) was weighed into a tray and its surface was moistened with about 8 milliliters water. Then 20 grams of the zinc fertilizer (of 150 mesh size) was added to it and mixed thoroughly. The mass was dried with a hot air drier (at 60° C.) with constant mixing of the mass. The zinc fertilizer coated on to the surface of DAP. The coating was firm and did not come off when rubbed between the fingers. The product contained 1.87 weight percent zinc, 1.4 weight percent magnesium, 17.1 weight percent phosphorus and 15 weight percent nitrogen. When the product was added to water, the zinc fertilizer particles dispersed over 30 minutes. This forms a convenient method of applying the zinc fertilizer in the field. It also enriches the DAP with micronutrient.

Example 4

Zinc Fertilizer Coated on SSP

A. Production of Zinc Fertilizer
The fertilizer of example 1 was used.
B. Coating on SSP
100 grams of SSP granules (2-4 mm, 7% P) was weighed into a dry glass jar and 5 grams of the zinc fertilizer (of 150 mesh size) was added to it. It was shaken by hand to mix the contents thoroughly. The zinc fertilizer adhered to the SSP and did not sediment at the bottom. The product contained 0.5 weight percent zinc and 7.3 weight percent phosphorus. When the product was added to water, the particles dispersed in 5 minutes. This enriches the SSP with micronutrient and forms a convenient carrier for the micronutrient.
C. Coating on SSP (Method II)
100 grams of SSP granules (2-4 mm, 7% P) was weighed into a tray and its surface was moistened with about 10 milliliters water. Then 25 grams of the zinc fertilizer (of 150 mesh size) was added to it and mixed thoroughly. The mass was dried with a hot air drier (at 60° C.) with constant mixing of the mass. The zinc fertilizer coated on to the surface of SSP. The product mainly contained 2.2 weight percent zinc, 1.7 weight percent magnesium and 8.2 weight percent phosphorus. When the product was added to water, the particles dispersed in a 20 minutes. This enriches the SSP with micronutrient and forms a carrier for zinc fertilizer application.

Example 5

Zinc Fertilizer Granulated

A. Production of Zinc Fertilizer
The fertilizer of example 1 was used.
B. Granulation (Method I)
100 grams of zinc fertilizer powder (80 mesh) was mixed with 15 grams of bentonite powder and granulated. The granules were hard and of good quality. The product mainly contained 9.7 weight percent zinc, 7.3 weight percent magnesium and 11.5 weight percent phosphorus. When the product was added to water, the particles dispersed in 10 minutes. This forms a convenient means of delivering the micronutrient.
C. Granulation (Method II)
100 grams of zinc fertilizer powder (80 mesh) was mixed with water and then granulated. These granules are softer than in method B above. The product contained 11.2 weight percent zinc, 13.2 weight percent phosphorus and 8.4 weight percent magnesium. When the product was added to water, the particles dispersed in 5 minutes. This forms a means of delivering the micronutrient.

Example 6

Zinc Fertilizer Coated on Urea

A. Production of Zinc Fertilizer Zn 200 3.058 P 158.4
The fertilizer was produced from green phosphoric acid (54% $P_2O_5$ and containing sludge) and zinc oxide (80% Zn) in the molar ratio Zn:P=1:1.75. Commercial grade phosphoric acid (54% $P_2O_5$), 672 grams (with 50 milliliters of sludge), was placed in a borosilicate beaker. The beaker was then placed in a heated oil bath and heated with stirring for 25 minutes until the temperature of the liquid was 120° C. Then 250 grams of commercial grade zinc oxide (80% Zn) was added to the hot phosphoric acid. The reaction was exothermic, and the temperature was raised to about 128° C. due to exothermic heat of the reaction. It was further heated till its temperature reached 130° C. Then 100 milliliters of water was added to the and heating was continued for 15 minutes until the temperature of the liquid reached 119° C. The beaker was then taken out of the heating unit. When the liquid temperature cooled to 90° C., a slurry of magnesium oxide (120 grams) in 400 milliliters of water was added to it with stirring whereupon a white suspension was formed. This was mixed well in a blender and dried in a tray drier at 70° C. The dried material was powdered in a pulverizer to pass through 150 mesh.

The product included 22.3 weight percent zinc, 8.45 weight percent magnesium, 7.24 weight percent calcium and 19.1 weight percent phosphorous. The ratio of equivalent of Zn to equivalent of P was 0.37. Number average chain length of the polyphosphate (excluding orthophosphate) was 4.76. Number average chain length of the polyphosphate (including orthophosphate) was 2.17. It had an orthophosphate content of 19%. In 2 weight percent citric acid the product released 98.5% of total zinc, 93.4% of total magnesium and 88.4% of total magnesium. In 0.005 molar DTPA the product released 93.4% of zinc, 90.1% of total magnesium and 87.7% of total calcium. In water 0.47% of total Zn, 4.6% of total magnesium, 0.25% of total calcium and 8.2% of total P was solubilized. Dissolution in weakly acidic solution of pH 4 was 0.79% of total zinc, 0.57% of total calcium and 4.6% of total magnesium. In a weakly alkaline solution, 0.56% of total zinc, 1% of total calcium and 4.33% of total magnesium was dissolved. In 0.02M EDTA at pH 4.65, 92.4% of total Zn, 95.2% of total calcium and 90.5% of total magnesium was solubilized. In 1N ammonium citrate at pH 8.5, 93.5% of total Zn and 92.7% of total calcium and 92.6% of total magnesium was solubilized. X-ray diffraction diagram for the product shows peaks at 23.62, 16.58, 11.17, 8.936, 8.067, 7.603, 6.177, 6.077, 5.913, 5.762, 5.627, 5.329, 5.245, 5.034, 4.913, 4.709, 4.559, 4.488, 4.399, 4.125, 4.083, 3.993, 3.878, 3.789, 3.652, 3.561, 3.452, 3.381, 3.183, 3.125, 3.069, 3.034, 2.949, 2.907, 2.845, 2.836, 2.787, 2.764, 2.712, 2.623, 2.605, 2.576, 2.514, 2.47, 2.426, 2.402, 2.368, 2.331, 2.263, 2.217, 2.152, 2.143, 2.1296, 2.0942, 1.9766, 1.9371, 1.9143, 1.8682, 1.8275, 1.7982, 1.7894, 1.7554, 1.7166, 1.6956, 1.6339, 1.5913, 1.5546 Å.

B. Coating on Urea
The process was the same as described in Example 1 except that 10 grams of the zinc fertilizer (of 150 mesh size) of this example was added to it. The product contained 2 weight percent zinc, 0.8 weight percent magnesium, 0.66 weight percent calcium, 1.74 weight percent phosphorus and 41.8 weight percent nitrogen. When the urea was added to water, the particles immediately dispersed and urea dissolved.

The maximum amount of zinc fertilizer that can be retained on the urea surface is 19.5 grams per 100 grams of urea.

Example 7

Zinc Fertilizer Coated on MAP

A. Production of Zinc Fertilizer
The fertilizer of example 6 was used.
B. Coating on MAP (Method I)
The process described in Example 2B was used except that 0.4 grams of the zinc fertilizer of the example 6 was added to it. The zinc fertilizer adhered well to the urea and did not sediment at the bottom. The product contained 0.1 weight percent zinc, 0.1 weight percent phosphorus and 46 weight percent nitrogen. When the MAP was added to water, the particles immediately dispersed and urea dissolved.

A maximum of 0.4 grams of this zinc fertilizer can be coated on 100 grams of urea.

C. Coating on MAP (Method II)

The process described in Example 2C was used except that 20 grams of the zinc fertilizer of the example 6 was added to it. The product contained 3.72 weight percent zinc, 1.4 weight percent magnesium, 1.2 weight percent calcium, 22.1 weight percent phosphorus and 9.2 weight percent nitrogen. When the product was added to water, the particles dispersed in about 30 minutes. This forms a convenient method of applying the zinc fertilizer in the field. It also enriches the urea with micronutrient.

Example 8

Zinc Fertilizer Granulated with SSP

A. Production of Zinc Fertilizer

The fertilizer of example 6 was used.

B. Granulation with SSP 100 grams of SSP powder (7% P) was mixed with 10 grams of the zinc fertilizer (of 150 mesh size). Water was added to moisten it. It was broken into small lumps and dried. The dried granules of large size were broken and sieved to obtain 2 mm granules. The product contained 2 weight percent zinc and 8.1 weight percent phosphorus. When the product was added to water, the particles dispersed in 60 minutes. The zinc fertilizer acts as a binder to promote granulation of SSP. It also enriches the SSP with micronutrient and forms a convenient carrier for the micronutrient.

Example 9

Zinc Fertilizer Coated on DAP

A. Production of Zinc Fertilizer

The fertilizer of example 6 was used.

B. Coating on DAP (Method I)

The process described in Example 3B was used except that 5 grams of the zinc fertilizer of the example 6 was added to it. The product contained 1 weight percent zinc, 0.4 weight percent magnesium, 0.34 weight percent calcium, 18 weight percent phosphorus and 17.1 weight percent nitrogen. When the DAP was added to water, the particles immediately dispersed. This forms a convenient method of applying the zinc fertilizer in the field. It also enriches the DAP with micronutrient.

A maximum of 5.5 grams of this zinc fertilizer can be coated on 100 grams of DAP.

C. Coating on DAP (Method II)

The process described in Example 3C was used except that 20 grams of the zinc fertilizer of the example 6 was added to it. The product contained 3.7 weight percent zinc, 1.4 weight percent magnesium, 1.2 weight percent calcium, 18.1 weight percent phosphorus and 15 weight percent nitrogen. When the DAP was added to water, the particles dispersed in about 45 minutes. The coating was firm and did not come off when rubbed between the fingers.

Example 10

Zinc Fertilizer Granulated with Mono Ammonium Phosphate (MAP) and its Use as a Granulating Agent A. Production of Zinc Fertilizer The fertilizer of example 6 was used.

B. Granulation 100 grams of MAP (crystalline powder) was mixed with 20 grams of zinc fertilizer powder and 8 milliliters of water and granulated by drying at 60° C. Hard granules were formed. The product contained 3.7 weight percent zinc, 1.4 weight percent magnesium, 1.2 weight percent calcium, 22.1 weight percent phosphorus and 9.17 weight percent nitrogen. When the product was added to water, the particles dispersed in 5 minutes. This forms a convenient means of granulating MAP and simultaneously delivering the micronutrient.

Example 11

Zinc Fertilizer Coated on Organic Granules

C. Production of Zinc Fertilizer

The fertilizer of example 6 was used.

D. Granulation 100 grams of composted plant waste granules was mixed with 30 grams of zinc fertilizer powder and 8 milliliters of water and granulated by drying at 60° C. Hard granules were formed. The product contained mainly 5.4 weight percent zinc, 4.9 weight percent phosphorus and 1.7 weight percent nitrogen. When the product was added to water, the particles dispersed in 5 minutes. This forms a convenient means of delivering the micronutrient.

Example 12

Zinc Fertilizer Coated on Seeds

A. Production of Zinc Fertilizer

The fertilizer of example 6 was used except it was further ground to size less than 300 mesh.

B. Coating on Seeds (Rice Seeds)

100 grams of rice seeds was weighed into a tray. In a beaker, 40 milliliters of water was taken and 5 grams bentonite powder was added to it and stirred. To the bentonite slurry 25 grams of the zinc fertilizer (300 mesh) was added and stirred. The slurry was poured over the rice seeds and then dried with an air blower at 40° C. with constant mixing. The product is rice seed with 4.3 weight percent zinc, 1.6 weight percent magnesium, 1.4 weight percent calcium, 3.7 weight percent phosphorus When the seeds were placed in water, the fertilizer dispersed immediately. This forms a convenient method of applying the zinc fertilizer in the field. It also enriches the DAP with micronutrient.

In an alternative method, the coating was produced by substituting bentonite with 10 grams of organic plant waste compost.

Example 13

Zinc-Manganese Fertilizer Coated on Urea

The fertilizer of this example was produced from phosphoric acid, zinc oxide, manganous oxide and magnesium oxide.

Phosphoric acid (green acid containing 54% $P_2O_5$ and sludge) 563 grams (with 50 milliliters of sludge), was placed in a borosilicate beaker. Then 100 grams of zinc oxide (80%

Zn) was added to the phosphoric acid in the beaker, with stirring. The reaction was exothermic. The beaker was placed in a heated oil bath and stirred for 10 minutes until the temperature of the liquid was 90° C. Then 133.4 grams of manganous oxide (60% Mn) was made into a slurry with 800 milliliters of water and added to the phosphoric acid-zinc oxide liquid with stirring. Further heating was done for 15 minutes until the temperature of the liquid reached 100° C. The beaker was then taken out of the heating unit and neutralized 55 grams of magnesium oxide in 350 milliliters water. A white suspension was formed. This was mixed well in a blender and dried in a tray drier at 70° C. The dried material was powdered in a pulverizer to pass through 150 mesh.

The product included 9.2 weight percent zinc, 9.4 weight percent manganese, 7.6 weight percent magnesium, 8 weight percent calcium and 16.2 weight percent phosphorous. The pH of this product was 4.1. The ratio of equivalent of Zn+Mn to equivalent of P was 0.4. Number average chain length of the polyphosphate (excluding orthophosphate) was 5.1. Number average chain length of the polyphosphate (including orthophosphate) was 1.62. It had an orthophosphate content of 33 wt %. In 2 weight percent citric acid the product released 97.8% of total zinc and 97.7% of total manganese, 92.2% of total magnesium and 90.4% of total calcium. In 0.005 M DTPA the product released 96.3% of total zinc and 95.4% of total manganese, 90.7% of total magnesium and 88.5% of total calcium. In water 1% of total Zn, 5.2% of total manganese, 5% of total magnesium, 0.5% of total calcium and 7.9% of total P was solubilized. Dissolution in weakly acidic solution of pH 4 was 1.2% of total zinc, 5.4% of total manganese, 0.8% of total calcium and 5.1% of total magnesium. In a weakly alkaline solution of pH 8, 1.5% of total zinc, 5.2% of total manganese, 1.3% of total calcium and 5% of total magnesium was dissolved. In 0.02M EDTA at pH 4.65, 95.6% of total Zn, 94.6% of total manganese, 89.3% of total calcium and 87.1% of total magnesium was solubilized. In 1N ammonium citrate at pH 8.5, 97.3% of total Zn, 95.5% of total manganese, 91.3% of total calcium and 88.3% of total magnesium was solubilized. X-ray diffraction diagram for the product shows peaks at 23.9, 17.3, 14.2, 13.2, 8.97, 8.06, 6.29, 5.953, 5.396, 5.132, 5.055, 4.936, 4.743, 4.622, 4.865, 4.152, 4.097, 3.944, 3.896, 3.809, 3.67, 3.55, 3.459, 3.377, 3.241, 3.132, 3.068, 2.918, 2.869, 2.832, 2.776, 2.731, 2.674, 2.655, 2.625, 2.592, 2.566, 2.533, 2.405, 2.375, 2.34, 2.294, 2.25, 2.223, 2.215, 2.174, 2.153, 2.131, 2.106, 1.969, 1.9454, 1.8729, 1.8458, 1.8355, 1.8199, 1.743, 1.7347, 1.6682, 1.6449, 1.607, 1.5631, 1.5591 Å.

B. Coating on Urea

The process was the same as described in Example 1 except that 20 grams of the zinc-manganese fertilizer (of 150 mesh size) of this example was added to it. The product contained 1.5 weight percent zinc, 1.6 weight percent manganese, 1.3 weight percent magnesium, 1.3 weight percent calcium, 2.7 weight percent phosphorus and 38.3 weight percent nitrogen. When the urea was added to water, the particles of micronutrient fertilizer immediately dispersed and urea dissolved.

This fertilizer can be coated to the maximum extent of 40 grams for every 100 grams of urea.

Example 14

Zinc-Manganese Fertilizer Coated on DAP

A. Production of Zinc-Manganese Fertilizer
The fertilizer of example 13 was used.
B. Coating on DAP (Method I)
The process was as described in Example 3B except that 5 grams of the zinc-manganese fertilizer of the example 13 was used. The product contained 0.4 weight percent zinc, 0.4 weight percent manganese, 0.4 weight percent magnesium, 0.4 weight percent calcium, 17.8 weight percent phosphorus and 17.1 weight percent nitrogen. When the product was added to water, the particles of micronutrient fertilizer immediately dispersed.

This fertilizer can be coated to the maximum extent of 7 grams for every 100 grams of DAP.

C. Coating on DAP (Method II)
The process described in Example 3C was used except that 20 grams of the zinc-manganese fertilizer of the example 13 was used. The product contained 1.5 weight percent zinc, 1.6 weight percent manganese, 1.3 weight percent magnesium, 1.3 weight percent calcium, 17.6 weight percent phosphorus and 15 weight percent nitrogen. When added to water the micronutrient dispersed slowly over 60 minutes.

Example 15

Zinc-Manganese Fertilizer Coated on MAP

A. Production of Zinc-Manganese Fertilizer
The fertilizer of example 13 was used.
B. Coating on MAP (Method I)
The process was as described in Example 2B except that 0.3 grams of the zinc-manganese fertilizer of the example 13 was used. The product contained 0.27 weight percent zinc, 0.27 weight percent manganese, 0.22 weight percent magnesium, 0.23 weight percent calcium, 22.5 weight percent phosphorus and 10.7 weight percent nitrogen. When the product was added to water, the particles immediately dispersed.

A maximum of 3.5 grams of this zinc-manganese fertilizer can be coated on 100 grams of MAP.

C. Coating on MAP (Method II)
The process described in Example 2C was used except that 20 grams of the zinc fertilizer of the example 13 was added to it. The product contained 1.5 weight percent zinc, 1.6 weight percent manganese, 1.3 weight percent magnesium, 1.3 weight percent calcium, 21.6 weight percent phosphorus and 9.2 weight percent nitrogen. When the product was added to water, the particles dispersed in about 30 minutes.

Example 16

Manganese Fertilizer Coated on Urea

B. Production of Manganese Fertilizer
The fertilizer was produced from green phosphoric acid (54% $P_2O_5$ and containing sludge) and manganous oxide (60% Mn) in the molar ratio Mn:P=1:1.5. Commercial grade phosphoric acid (54% $P_2O_5$), 437 grams (with 25 milliliters of sludge), was placed in a borosilicate beaker and 220 milliliters water was added to it. The beaker was then placed in a heated oil bath and heated 60° C. Then 194 grams of commercial grade manganous oxide (60.8% Mn) was mixed with 700 milliliters water and the slurry was added to the hot phosphoric acid. It was further heated for about 20 minutes till its temperature reached 102° C. The beaker was then taken out of the heating unit. When the liquid temperature cooled to 90° C., a slurry of magnesium oxide (50 grams, 60% Mn) in 350 milliliters of water was added to it with stirring whereupon a white suspension was formed. This was mixed well in a blender and dried in a tray drier at 70° C. The dried material was powdered in a pulverizer to pass through 150 mesh.

The product included 16.3 weight percent manganese, 8.3 weight percent magnesium, 6.6 weight percent calcium and 15.8 weight percent phosphorous. The pH of a 10% suspension was 4.56. The ratio of equivalent of Mn to equivalent of P was 0.39. In 2 weight percent citric acid the product released 95.6% of total manganese, 93.1% of total magnesium and 89.3% of total calcium. In 0.005 molar DTPA the product released 94.6% of total manganese, 90.6% of total magnesium and 86.3% of total calcium. In water 4.8% of total manganese, 4.6% of total magnesium and 0.4% of total calcium and 8% of total P was solubilized. Dissolution in weakly acidic solution of pH 4 was 4% of total manganese, 4.6% of total magnesium and 0.7% of total calcium. In a weakly alkaline solution, 3.9% of total manganese, 1.2% of total calcium and 4.6% of total magnesium was dissolved. In 0.02M EDTA at pH 4.65, 93.4% of total manganese, 90.4% of total calcium and 90.3% of total magnesium was solubilized. In 1N ammonium citrate at pH 8.5, 96.4% of total manganese, 93% of total calcium and 94.5% of total magnesium was solubilized. X-ray diffraction diagram for the product shows peaks at 24, 11.9, 8.65, 8.06, 7.42, 6.89, 6.49, 6.246, 5.945, 5.723, 5.383, 5.297, 4.694, 4.608, 4.316, 4.221, 4.117, 3.978, 3.845, 3.789, 3.445, 3.263, 3.144, 3.04, 2.97, 2.786, 2.728, 2.573, 2.549, 2.5, 2.353, 2.305, 2.1604, 2.1285, 2.0924, 2.0436, 1.9025, 1.8463, 1.8244, 1.7994, 1.6811, 1.6731 Å.

B. Coating on Urea

The process was the same as described in Example 1 except that 10 grams of the manganese fertilizer (of 150 mesh size) of this example was added to it. The product contained 1.5 weight percent manganese, 0.73 weight percent magnesium, 0.6 weight percent calcium, 1.4 weight percent phosphorus and 41.8 weight percent nitrogen. When the urea was added to water, the particles immediately dispersed and urea dissolved.

The maximum amount of manganese fertilizer that can be retained on the urea surface is 30 grams per 100 grams of urea.

Example 17

Manganese Fertilizer Coated on MAP

C. Production of Zinc Fertilizer
The fertilizer of example 16 was used.
D. Coating on MAP (Method I)

The process described in Example 2B was used except that 2 grams of the manganese fertilizer of the example 16 was added to it. The product contained 0.32 weight percent manganese, 0.16 weight percent magnesium, 0.13 weight percent calcium, 22.5 weight percent phosphorus and 10.8 weight percent nitrogen. When the MAP was added to water, the micronutrient fertilizer particles immediately dispersed.

A maximum of 2 grams of this zinc fertilizer can be coated on 100 grams of urea.

C. Coating on MAP (Method II)

The process described in Example 2C was used except that 15 grams of the manganese fertilizer of the example 16 was added to it. The product contained 2.1 weight percent manganese, 1.1 weight percent magnesium, 0.86 weight percent calcium, 21.8 weight percent phosphorus and 9.6 weight percent nitrogen. When the product was added to water, the particles dispersed in about 30 minutes.

Example 18

Manganese Fertilizer coated on DAP

C. Production of Manganese Fertilizer
The fertilizer of example 16 was used.
D. Coating on DAP (Method I)

The process described in Example 3B was used except that 1 grams of the manganese fertilizer of the example 16 was added to it. The product contained 0.16 weight percent manganese, 0.08 weight percent magnesium, 0.06 weight percent calcium, 17.9 weight percent phosphorus and 17.8 weight percent nitrogen. When the DAP was added to water, the particles immediately dispersed.

A maximum of 1.6 grams of this manganese fertilizer can be coated on 100 grams of DAP.

C. Coating on DAP (Method II)

The process described in Example 3C was used except that 20 grams of the manganese fertilizer of the example 16 was added to it. The product contained 2.7 weight percent manganese, 1.4 weight percent magnesium, 1.1 weight percent calcium, 17.6 weight percent phosphorus and 15 weight percent nitrogen. When the DAP was added to water, the particles dispersed in about 45 minutes. The coating was firm and did not come off when rubbed between the fingers.

Example 19

Manganese Fertilizer Coated on Urea

C. Production of Manganese Fertilizer

The fertilizer was produced from phosphoric acid (58.4% $P_2O_5$), manganous oxide (60% Mn) and magnesium oxide (54% Mg) in the molar ratio Mn:P=1:1.5. Commercial grade phosphoric acid (58.4% $P_2O_5$), 437 grams, was placed in a borosilicate beaker and 220 milliliters water was added to it. The beaker was then placed in a heated oil bath and heated for 10 minutes 60° C. Then 220 grams of commercial grade manganous oxide (60% Mn) was mixed with 200 milliliters water and the slurry was added to the hot phosphoric acid. A further 750 milliliters of water was added. The reaction was exothermic and liquid temperature increased to 80° C. It was further heated for about 20 minutes till its temperature reached 100° C. The beaker was then taken out of the heating unit. When the liquid temperature cooled to 80° C., a slurry of magnesium oxide (82 grams) in 150 milliliters of water was added to it with stirring whereupon a white suspension was formed. This was mixed well in a blender and dried in a tray drier at 70° C. The dried material was powdered in a pulverizer to pass through 150 mesh.

The product included 16.8 weight percent manganese, 6.4 weight percent magnesium and 14.3 weight percent phosphorous. The ratio of equivalent of Mn to equivalent of P was 0.44. The pH of this product in a 10% suspension was 6.76. In 2 weight percent citric acid the product released 96.7% of total manganese and 94.2% of total magnesium. In 0.005 molar DTPA the product released 92.2% of total manganese and 91.1% of total magnesium. In water 2.9% of total manganese, 6% of total magnesium and 8.4% of total P was solubilized. Dissolution in weakly acidic solution of pH 4 was 3.2% of total manganese, 5.9% of total magnesium. In a weakly alkaline solution, 3.4% of total manganese and 6.1% of total magnesium was dissolved. In 0.02M EDTA at pH 4.65, 98% of total manganese and 96.7% of total magnesium was solubilized. In 1N ammonium citrate at pH 8.5, 89.7% of total manganese and 94.2% of total magnesium was solubilized. X-ray diffraction diagram for the product shows peaks at 20.3, 17.8, 16.45, 15.16, 12.42, 10.15, 8.97, 7.91, 6.77, 6.356, 5.867, 5.791, 5.308, 4.954, 4.813, 4.652, 4.471, 3.829, 3.654, 3.446, 3.328, 3.26, 3.22, 3.173, 3.128, 3.063, 3.024, 2.969, 2.931, 2.918, 2.895, 2.857, 2.789, 2.679, 2.215, 2.179, 2.131, 2.095, 1.993, 1.926, 1.889, 1.878, 1.852, 1.829, 1.729, 1.719, 1.6354, 1.6163, 1.5991 Å.

B. Coating on Urea

The process was the same as described in Example 1 except that 10 grams of the manganese fertilizer (of 150 mesh size) of this example was added to it. The product contained 1.5 weight percent manganese, 0.58 weight percent magnesium, 1.3 weight percent phosphorus and 41.8 weight percent nitrogen. When the urea was added to water, the particles immediately dispersed and urea dissolved.

The maximum amount of manganese fertilizer that can be retained on the urea surface is 20 grams per 100 grams of urea.

Example 20

Manganese Fertilizer Coated on MAP

A. Production of Zinc Fertilizer
The fertilizer of example 19 was used.
B. Coating on MAP (Method I)
The process described in Example 2B was used except that 1 gram of the manganese fertilizer of the example 19 was added to it. The product contained 0.17 weight percent manganese, 0.06 weight percent magnesium, 22.6 weight percent phosphorus and 10.9 weight percent nitrogen. When the MAP was added to water, the particles immediately dispersed and urea dissolved.

A maximum of 1.2 grams of this manganese fertilizer can be coated on 100 grams of urea.

C. Coating on MAP (Method II)
The process described in Example 2C was used except that 10 grams of the manganese fertilizer of the example 19 was added to it. The product contained 1.53 weight percent manganese, 0.58 weight percent magnesium, 21.9 weight percent phosphorus and 10 weight percent nitrogen. When the product was added to water, the particles dispersed in about 30 minutes.

Example 21

Manganese Fertilizer Coated on DAP

E. Production of Manganese Fertilizer
The fertilizer of example 19 was used.
F. Coating on DAP (Method I)
The process described in Example 3B was used except that 1 gram of the manganese fertilizer of the example 19 was added to it. The product contained 0.17 weight percent manganese, 0.06 weight percent magnesium, 17.9 weight percent phosphorus and 17.8 weight percent nitrogen. When the DAP was added to water, the particles immediately dispersed.

A maximum of 2 grams of this manganese fertilizer can be coated on 100 grams of DAP.

C. Coating on DAP (Method II)
The process described in Example 3C was used except that 10 grams of the manganese fertilizer of the example 19 was added to it. The product contained 1.5 weight percent manganese, 0.58 weight percent magnesium, 17.6 weight percent phosphorus and 16.4 weight percent nitrogen. When the DAP was added to water, the particles dispersed in about 45 minutes. The coating was firm and did not come off when rubbed between the fingers.

Example 22

Iron-Manganese Fertilizer Coated on Urea

The fertilizer of this example was produced from phosphoric acid, magnetite ($Fe_3O_4$, 69% Fe), manganous oxide (60% Mn) and magnesium oxide (54% Mg).

Commercial grade phosphoric acid (58.5% $P_2O_5$), 199 grams, was placed in a borosilicate beaker and mixed with 100 milliliters water. This was placed in an oil bath and heated to 60° C. Then a slurry of 100 grams of manganous oxide in 350 milliliters water was made and this was added to the phosphoric acid. Heating was continued till the temperature of the liquid reached 101° C. In another beaker, 769 grams of phosphoric acid was taken. Magnetite (174 grams) was made into a slurry with 200 milliliters water. This slurry was added to the phosphoric acid in the beaker. A further 150 milliliters water was added. The reaction was very exothermic, and the temperature was raised to about 90° C. This magnetite containing liquid was then added to the manganous oxide containing liquid. A further 450 milliliters water was added. The beaker was then placed in an oil bath and heated again till the liquid temperature reached 62° C. The beaker was then taken out of the heating unit. Then 180 grams of magnesium oxide was made into a slurry with 2 liters water. This was added to the liquid with stirring. Then it was dried at 60° C. and powdered in a pulverizer to pass through 150 mesh.

The product included 10.4 weight percent iron, 5.3 weight percent manganese, 5.9 weight percent magnesium and 22 weight percent phosphorous. The ratio of equivalent of Zn to equivalent of P was 0.35. The pH of this product was 4.24. In 2 weight percent citric acid the product released 89.1% of total iron, 96.2 weight percent of total manganese, 93.5 weight percent of total magnesium. In 0.005 molar DTPA the product released 93.6% of total iron, 97.6 weight percent of total manganese, 90.4 weight percent of total magnesium. In water 0.12% of total iron, 3.98 weight percent of total manganese, 5.7 weight percent of total magnesium and 8.3% of total P was solubilized. Dissolution in weakly acidic solution of pH 4 was 0.02% of total iron, 4.5 weight percent of total manganese, 6.2 weight percent of total magnesium. In a weakly alkaline solution, 0.04% of total iron, 4.65 weight percent of total manganese, 6.34 weight percent of total magnesium was dissolved. In 0.02M EDTA at pH 4.65, 88.7% of total iron, 90.6 weight percent of total manganese, 94.2 weight percent of total magnesium was solubilized. In 1N ammonium citrate at pH 8.5, 85.4 weight percent of total iron, 88.6 weight percent of total manganese, 95.3 weight percent of total magnesium was solubilized. X-ray diffraction diagram for the product shows peaks at 24.9, 18.9, 14.4, 11.8, 8.7, 8.3, 7.0, 6.82, 6.71, 6.57, 5.91, 5.357, 5.056, 4.72, 4.469, 4.229, 4.137, 3.856, 3.671, 3.459, 3.341, 3.261, 3.196, 3.087, 3.030, 2.797, 2.728, 2.704, 2.632, 2.605, 2.596, 2.514, 2.375, 2.198, 2.138, 2.108, 2.062, 2.031, 1.990, 1.932, 1.902, 1.863, 1.846, 1.835, 1.825, 1.794, 1.773, 1.76, 1.746, 1.727, 1.685, 1.604, 1.586 Å.

B. Coating on Urea 100 grams of urea was weighed into a dry glass jar and 15 grams of the iron-manganese fertilizer (of 150 mesh size) was added to it. It was shaken by hand to mix the contents thoroughly. The iron-manganese fertilizer adhered to the urea and did not sediment at the bottom. The product contained 1.3 weight percent iron, 0.69 weight percent manganese, 0.77 weight percent magnesium, 2.9 weight percent phosphorus and 40 weight percent nitrogen. When the urea was added to water, the particles immediately dispersed and urea dissolved.

This fertilizer can be coated to the maximum extent of 30 grams for every 100 grams of urea.

Example 23

Iron-Manganese Fertilizer Coated on MAP

A. Production of Zinc Fertilizer
The fertilizer of example 6 was used.
B. Coating on MAP (Method I)
The process described in Example 2B was used except that 1 gram of the iron-manganese fertilizer of the example 22 was added to it. The product contained 0.1 weight percent iron, 0.05 weight percent manganese, 0.06 weight percent magnesium, 22.7 weight percent phosphorus and 10.9 weight percent nitrogen. When the product was added to water, the micronutrient fertilizer particles immediately dispersed.

A maximum of 1.2 grams of this iron-manganese fertilizer can be coated on 100 grams of MAP.

C. Coating on MAP (Method II)
The process described in Example 2C was used except that 5 grams of the iron-manganese fertilizer of the example 22 was added to it. The product contained 0.5 weight percent iron, 0.25 weight percent manganese, 0.28 weight percent magnesium, 22.7 weight percent phosphorus and 10.5 weight percent nitrogen. When the product was added to water, the particles dispersed in about 30 minutes.

Example 24

Iron-Manganese Fertilizer Coated on DAP

A. Production of Manganese Fertilizer
The fertilizer of example 22 was used.
B. Coating on DAP (Method I)
The process described in Example 3B was used except that 5 grams of the iron-manganese fertilizer of the example 22 was added to it. The product contained 0.5 weight percent iron, 0.25 weight percent manganese, 0.28 weight percent magnesium, 18.1 weight percent phosphorus and 17.1 weight percent nitrogen. When the DAP was added to water, the particles immediately dispersed. This forms a convenient method of applying the zinc fertilizer in the field. It also enriches the DAP with micronutrient.

A maximum of 7 grams of this iron-manganese fertilizer can be coated on 100 grams of DAP.

C. Coating on DAP (Method II)
The process described in Example 3C was used except that 15 grams of the iron-manganese fertilizer of the example 22 was added to it. The product contained 1.35 weight percent iron, 0.69 weight percent manganese, 0.77 weight percent magnesium, 18.4 weight percent phosphorus and 15.6 weight percent nitrogen. When the DAP was added to water, the particles dispersed in about 45 minutes. The coating was firm and did not come off when rubbed between the fingers.

Example 25

Calcium Polyphosphate Fertilizer Coated on Urea

The fertilizer of this example was produced from phosphoric acid and calcium carbonate. Commercial grade phosphoric acid (58.4% $P_2O_5$), 66 grams, was placed in a beaker. In another beaker 50 milliliters of water was taken and 25.06 grams calcium carbonate (40% Ca) was added to it to form a slurry. This slurry was added to the phosphoric acid with stirring. It was then heated in an oil bath for 10 minutes till the temperature of the liquid reached 70° C. At this stage the liquid became thick. A further 30 milliliters of water was added. It was heated for another 20 minutes till the liquid temperature reached 103° C.

The sample was removed from the oil bath and allowed to cool to about 80° C. Then 14 grams of calcium oxide was suspended in 100 milliliters of water and added to the phosphate liquid with stirring. The product was poured in a drying dish and dried in an oven at 70° C. After it was dry, the sample was ground and sieved through a 150 mesh sieve.

On analysis, the product showed 19.12 weight percent phosphorus and 22 weight percent calcium. The ratio of equivalents of P:Ca was 0.59:1. The pH of a 10% suspension in water was 5.56. The number average chain length of the product was 4.9. Solubility of calcium from this product in water was 1.1% of the total calcium. In 0.1 weight percent citric acid 97% of the total calcium dissolved. In 0.01 N hydrochloric acid 91% of the total calcium dissolved. In 0.005M EDTA, 99% of the total calcium dissolved.

B. Coating on Urea
100 grams of urea was weighed into a dry glass jar and 30 grams of the polyphosphate fertilizer (of 150 mesh size) was added to it. It was shaken by hand to mix the contents thoroughly. The zinc fertilizer adhered to the urea and did not sediment at the bottom. The product contained 5.1 weight percent calcium, 4.4 weight percent phosphorus and 35.6 weight percent nitrogen. When the urea was added to water, the particles immediately dispersed and urea dissolved.

This fertilizer can be coated to the maximum extent of 40 grams for every 100 grams of urea.

Example 26

Calcium Polyphosphate Fertilizer Coated on DAP

A. Production of Calcium Polyphosphate Fertilizer
The fertilizer of example 25 was used.
B. Coating on DAP (Method II)
The process described in Example 3C was used except that 5 grams of calcium polyphosphate of example 25 was used. The calcium polyphosphate fertilizer coated on to the surface of DAP. The coating was firm and did not come off when rubbed between the fingers. The product contained 1 weight percent calcium, 17.96 weight percent phosphorus and 17.1 weight percent nitrogen. When the product was added to water, the calcium polyphosphate fertilizer particles dispersed over 30 minutes.

Example 27

Calcium Polyphosphate Fertilizer Granulated

A. Production of Calcium Polyphosphate Fertilizer
The fertilizer of example 1 was used.
B. Granulation (Method I)
100 grams of calcium polyphosphate fertilizer powder (80 mesh) was mixed with 15 grams of bentonite powder and granulated. The granules were hard and of good quality. The product contained 19.1 weight percent calcium and 16.6 weight percent phosphorus. When the product was added to water, the particles dispersed in 10 minutes. This forms a convenient means of delivering the fertilizer.

C. Granulation (Method II)

100 grams of calcium polyphosphate fertilizer powder (80 mesh) was mixed with water and then granulated. These granules are softer than in method b above. The product contained 22 weight percent calcium and 19.12 weight percent phosphorus. When the product was added to water, the particles dispersed in 5 minutes. This forms a means of delivering the micronutrient.

Example 28

Calcium-Magnesium Polyphosphate Fertilizer Coated on Urea

The fertilizer of this example was produced from phosphoric acid, calcium carbonate and magnesium oxide. Commercial grade phosphoric acid (58.4% $P_2O_5$), 83 grams, was placed in a beaker. Then 25.06 grams calcium carbonate and 8.1 grams magnesium oxide was suspended in 80 milliliters of water and the suspension was added to the phosphoric acid with stirring. Exothermic reaction occurs and the liquid temperature is raised to 70° C. It was then heated in an oil bath for 40 minutes till the temperature of the liquid reached 107° C. The beaker was removed from the heating unit and when the liquid had cooled to about 80° C., a suspension of calcium oxide in water (10.5 g CaO in 20 milliliters water) was added in a stream with continuous stirring. The product was poured in a drying dish and dried in an oven at 75° C. After it was dry, the sample was ground in a mortar. It was sieved through a 150 mesh sieve.

On analysis, the product showed 19.85 weight percent phosphorus, 16.5 weight percent calcium and 4.6 weight percent magnesium. The ratio of equivalents of Ca+Mg to P was 0.62:1. The pH of a 10% suspension in water was 4.97. Solubility of calcium from this product in water was 0.6% of the total calcium and 4.7% of total magnesium. In 0.1 weight percent citric acid 98% of the total calcium and 98% of the total magnesium dissolved. In 0.01 N hydrochloric acid 97% of the total calcium and 98% of total magnesium dissolved. In 0.005M EDTA, 98% of the total calcium and magnesium dissolved. XRD for this product showed peaks at 6.8, 5.96, 5.37, 5.01, 4.7, 4.61, 4.5, 4.15, 3.7, 3.66, 3.58, 3.47, 3.39, 3.35, 3.19, 3.13, 3.09, 3.05, 2.96, 2.94, 2.82, 2.76, 2.73, 2.59, 2.53, 2.5, 2.43, 2.41, 2.39, 2.37, 2.34, 2.25, 2.2, 2.18, 2.16, 2.14, 2.12, 2.09, 2.08, 2.03, 1.99, 1.93, 1.91, 1.85, 1.8, 1.76, 1.72, 1.68, 1.64, 1.59 and 1.57 Å.

B. Coating on Urea

The process was the same as described in Example 1 except that 50 grams of the calcium-magnesium polyphosphate fertilizer (of 150 mesh size) of this example was added to it. The polyphosphate fertilizer showed excellent adhesion to urea and did not sediment at the bottom. The product contained 5.5 weight percent calcium, 1.5 weight percent magnesium, 6.6 weight percent phosphorus and 30.7 weight percent nitrogen. When the urea was added to water, the particles immediately dispersed and urea dissolved.

This fertilizer can be coated to the maximum extent of 67 grams for every 100 grams of urea.

Example 29

Calcium-Magnesium Polyphosphate Fertilizer Coated on MAP

A. Production of Calcium-Magnesium Polyphosphate Fertilizer

The fertilizer of example 28 was used.

B. Coating on MAP (Method I)

The process described in Example 2B was used except that 5 grams of the calcium-magnesium polyphosphate fertilizer of the example 28 was added to it. The product contained 0.78 weight percent calcium, 0.22 weight percent magnesium, 22.5 weight percent phosphorus and 10.5 weight percent nitrogen. When the MAP was added to water, the micronutrient fertilizer particles immediately dispersed.

A maximum of 7 grams of this calcium-magnesium polyphosphate fertilizer can be coated on 100 grams of MAP C. Coating on MAP (Method II)

The process described in Example 2C was used except that 10 grams of the calcium-magnesium polyphosphate fertilizer of the example 28 was added to it. The product contained 1.5 weight percent calcium, 0.42 weight percent magnesium, 22.4 weight percent phosphorus and 10 weight percent nitrogen. When the product was added to water, the particles dispersed in about 30 minutes.

Example 30

Calcium-Magnesium Polyphosphate Fertilizer Granulated

A. Production of Calcium-Magnesium Polyphosphate Fertilizer

The fertilizer of example 28 was used.

B. Granulation (Method I)

The process was the same as used in example 27 except that calcium-magnesium polyphosphate fertilizer of the example 28 was used. The granules were hard and of good quality. The product contained 14.3 weight percent calcium and 17.3 weight percent phosphorus. When the product was added to water, the particles dispersed in 10 minutes. This forms a convenient means of delivering the fertilizer.

C. Granulation (Method II)

100 grams of calcium polyphosphate fertilizer powder (80 mesh) was mixed with water and then granulated. These granules are softer than in method b above. The product contained 16.5 weight percent calcium, 4.6 weight percent magnesium and 19.8 weight percent phosphorus. When the product was added to water, the particles dispersed in 5 minutes.

Example 31

Calcium-Magnesium Polyphosphate Fertilizer Coated on Urea

The fertilizer of this example two was produced from phosphoric acid, calcium carbonate and magnesium oxide. Commercial grade phosphoric acid (58.4% $P_2O_5$), 83 grams, was placed in a beaker. Then 40 grams calcium carbonate and 8.1 grams magnesium oxide was suspended in 80 milliliters of water and the suspension was added to the phosphoric acid with stirring. Exothermic reaction occurs and the liquid temperature is raised to 70° C. It was then heated in an oil bath for 30 minutes till the temperature of the liquid reached 103° C. The beaker was removed from the heating unit and when the liquid had cooled to about 80° C., a suspension of calcium oxide in water (5 g CaO in 20 milliliters water) was added in a stream with continuous stirring. The product was poured in a drying dish and dried in an oven at 75° C. After it was dry, the sample was ground in a mortar. It was sieved through a 150 mesh sieve.

On analysis, the product showed 19.46 weight percent phosphorus, 17.6 weight percent calcium and 5.14 weight percent magnesium. The ratio of equivalents of (Ca+Mg) to P was 0.69. The pH of a 10% suspension in water was 5.1. The number average chain length of the product was 4.5. Solubility of calcium from this product in water was 0.4% of the total calcium and 4.9% of total magnesium. In 0.1 weight percent citric acid 95% of the total calcium and 96% of the total magnesium dissolved. In 0.01 N hydrochloric acid 96% of the total calcium and 98% of total magnesium dissolved. In 0.005M EDTA, 96% of the total calcium and 98% of total magnesium dissolved.

B. Coating on Urea

The process was the same as described in Example 1 except that 60 grams calcium-magnesium polyphosphate fertilizer of this example was used. The calcium-magnesium polyphosphate fertilizer showed very good adherence urea and did not sediment at the bottom. The product contained 6.6 weight percent calcium, 1.92 weight percent magnesium, 7.3 weight percent phosphorus and 28.7 weight percent nitrogen. When the urea was added to water, the particles immediately dispersed and urea dissolved.

This fertilizer can be coated to the maximum extent of 68 grams for every 100 grams of urea.

Example 32

Calcium-Magnesium Polyphosphate Fertilizer Coated on DAP

A. Production of Calcium-Magnesium Polyphosphate Fertilizer

The fertilizer of example 28 was used.

B. Coating on DAP (Method I)

The process described in Example 3B was used except that 10 grams of the calcium-magnesium polyphosphate fertilizer of the example 31 was added to it. The product contained 1.6 weight percent calcium, 0.41 weight percent magnesium, 18 weight percent phosphorus and 16.4 weight percent nitrogen. When the DAP was added to water, the particles immediately dispersed.

A maximum of 13.5 grams of this calcium-magnesium polyphosphate fertilizer can be coated on 100 grams of DAP.

C. Coating on DAP (Method II)

The process described in Example 3C was used except that 30 grams of the calcium-magnesium polyphosphate fertilizer of the example 31 was added to it. The product contained 4.1 weight percent calcium, 1 weight percent magnesium, 18.3 weight percent phosphorus and 13.8 weight percent nitrogen. When the DAP was added to water, the particles dispersed in about 45 minutes. The coating was firm and did not come off when rubbed between the fingers.

Example 33

Calcium-Magnesium Polyphosphate Fertilizer Granulated with Urea

A. Production of Calcium-Magnesium Polyphosphate Fertilizer

The fertilizer of example 31 was used.

B. Granulation with Urea 100 grams of urea was mixed with 50 grams of the calcium-magnesium polyphosphate fertilizer (of 150 mesh size). Water was added to moisten it and it was mixed thoroughly. It was dried at 65° C. The dried granules of large size were broken and sieved to obtain 2 mm granules. The granules were hard. The product contained 5.9 weight percent calcium, 1.7 weight percent magnesium, 6.5 weight percent phosphorus and 30.7 weight percent nitrogen.

Example 34

Calcium-Magnesium Polyphosphate Fertilizer Granulated with Ammonium Sulfate Use as a Binding Agent for Ammonium Sulfate Granulation C. Production of Calcium-Magnesium Polyphosphate Fertilizer The fertilizer of example 31 was used.

D. Granulation with Ammonium Sulfate

The process was similar to that described in example 33 except that 20 grams of the calcium-magnesium polyphosphate fertilizer of example 31 was used. The granules were hard. The product contained 2.9 weight percent calcium, 0.85 weight percent magnesium, 3.24 weight percent phosphorus, 20 weight percent sulfur and 17.5 weight percent nitrogen.

Example 35

Calcium-Zinc Polyphosphate Fertilizer Coated on Urea

The fertilizer of this example two was produced from phosphoric acid, calcium carbonate (40% Ca) and zinc oxide (80% Zn). Commercial grade phosphoric acid (58.4% $P_2O_5$), 71.6 grams, was placed in a beaker. Then 25.06 grams calcium carbonate and 1.61 grams zinc oxide was suspended in 50 milliliters of water and the suspension was added to the phosphoric acid with stirring. It was then heated in an oil bath for 45 minutes till the temperature of the liquid reached 105° C. The beaker was removed from the heating unit and allowed to cool to about 70° C. Then a suspension of calcium oxide in water (14.5 grams CaO in 30 milliliters water) was added in a stream with continuous stirring. At this stage a white suspension was formed. The product was poured in a drying dish and dried in an oven at 75° C. After it was dry, the sample was ground by hand in a mortar. It was sieved through a 150 mesh sieve.

On analysis, the product showed 18.56 weight percent phosphorus, 20.7 weight percent calcium and 1.3 weight percent zinc. The ratio of equivalents of Ca to P was 0.58:1. The pH of a 10% suspension in water was 6.52. Solubility of calcium from this product in water was 0.9% of the total calcium and 1% of total magnesium. In 0.1 weight percent citric acid 99% of the total calcium and 97% of the total zinc dissolved. In 0.01 N hydrochloric acid 99% of the total calcium and 98% of the total zinc dissolved. In 0.005M EDTA, 98% of the total calcium and 97% of total zinc dissolved.

B. Coating on Urea

The process was the same as described in example 1 except that 20 grams of calcium-zinc polyphosphate fertilizer of this example was used. The zinc fertilizer adhered to the urea and did not sediment at the bottom. The product contained 3.45 weight percent calcium, 0.22 weight percent zinc, 3.1 weight percent phosphorus, and 38.3 weight percent nitrogen. When the urea was added to water, the particles immediately dispersed and urea dissolved. This forms a convenient method of applying the zinc fertilizer in the field. It also enriches the urea with micronutrient.

This fertilizer can be coated to the maximum extent of 44 grams for every 100 grams of urea.

Example 36

Zinc Fertilizer Coated on Urea

B. Production of Zinc Fertilizer

The fertilizer was produced from phosphoric acid (52% $P_2O_5$) and zinc ash (72% Zn). Commercial grade phosphoric acid (52% $P_2O_5$), 160 grams, was placed in a stainless tray made of SS316L. Then zinc ash was added and stirred to form a slurry. The tray was placed in a muffle furnace and heated at 170° C. for 30 minutes followed by heating at 350° C. for 60 minutes till a thick paste was produced. The reacted material was allowed to cool to room temperature where upon it solidified. It was mixed with water to form a slurry and 59 milliliters of 25% ammonia solution was added to it with stirring whereupon a white suspension was formed. This was mixed well in a blender and dried in a tray drier at 80° C. The dried material was powdered in a pulverizer to pass through 100 mesh.

The product included 21 weight percent zinc, 5.1 weight percent nitrogen and 19.1 weight percent phosphorous. It had a pH of 4. The ratio of equivalent of Zn to equivalent of P was 0.347. In 6.9 weight percent citric acid (0.33M citric acid), 0.005 molar DTPA and 0.1N HCl the product released 100 wt % of zinc in 15 minutes. In water 7.5% of total Zn was solubilized. X-ray diffraction diagram for the product shows a broad hump at around 6 Å and peaks at 13.4, 9.21, 7.76, 7.25, 6.71, 6.51, 5.98, 5.61, 5.40, 4.79, 4.44, 3.480, 3.327, 3.198, 3.079, 2.998, 2.867, 2.797, 2.607, 2.481, 2.344, 2.036 Å.

B. Coating on Urea 5 kilograms grams of urea granules (1-3 mm, 46% N) was weighed into a mixer and 250 grams of the zinc fertilizer (of 100 mesh size) was added to it. It was mixed for 3 minutes and discharged. The zinc fertilizer adhered to the urea and did not sediment at the bottom. The product mainly contained 1 weight percent zinc, 0.91 weight percent phosphorus and 44 weight percent nitrogen. When the urea was added to water, the zinc fertilizer particles immediately dispersed and urea dissolved.

A maximum of 60 grams of this zinc fertilizer can be coated on each kilogram of urea.

Example 37

Zinc Fertilizer Coated on DAP

B. Production of Zinc Fertilizer
The fertilizer of example 36 was used.
A. Coating on DAP (Method I)

5 kilograms of DAP granules (1-4 mm, 18% N, 17.9% P) was weighed into a rapid mixer granulator and its surface was sprayed with about 200 milliliters water. Then 550 grams of the zinc fertilizer (of 150 mesh size) was added to it and mixed thoroughly. The mass was discharged and dried with a hot air drier (at 60° C.) with constant mixing of the mass. The zinc fertilizer coated on to the surface of DAP. The coating was firm and did not come off when rubbed between the fingers. The product contained 2 weight percent zinc, 18 weight percent phosphorus and 16.7 weight percent nitrogen. When the product was added to water, the zinc fertilizer particles dispersed over 35 minutes. This forms a convenient method of applying the zinc fertilizer in the field. It also enriches the DAP with micronutrient.

Example 38

Zinc Fertilizer Granulated

D. Production of Zinc Fertilizer

The fertilizer was produced as described in example 36. After neutralization with ammonia the suspension was partially dried to 50 wt % moisture and then transferred into a granulator.

E. Granulation 5 kilograms of moist zinc fertilizer was granulated in a rapid mixer granulator to a size of 1 mm. The granules were then transferred to a hot air drier and dried at 70° C. The granules were hard and were resistant to breaking between the thumb and first finger. The product contained 21 weight percent zinc, 19.1 weight percent phosphorus and 5.1 weight percent nitrogen. When the product was added to water, the particles dispersed in 10 minutes. This forms a means of delivering the micronutrient.

Example 39

Molybdenum Fertilizer Coated on Seeds

C. Production of Molybdenum Fertilizer

Phosphoric acid (122 g) containing 60% $P_2O_5$ was placed in a glass beaker and 7.5 g molybdenum trioxide ($MoO_3$ containing 66% Mo), 22 g magnesium oxide (60% Mg) and 11 g sodium carbonate (43% Na) were added to it with stirring. The mixture was poured into stainless steel trays and placed in a muffle furnace at 300° C. After 90 min of heating a solid product was obtained. It was ground and sieved through a 100 mesh. The product contained 4.1 wt % molybdenum, 12.7 wt % magnesium, 27.7 wt % phosphorus and 1.8 wt % sodium. In, 0.1 M HCl, and 0.33 M citric acid more than 98 wt % of the total molybdenum dissolved.

D. Coating on Seeds (Soybean Seeds)

1 kilogram of soybean seeds was weighed into a horizontal mixer. In a beaker, 200 milliliters of water was taken and 30 grams bentonite powder was added to it and stirred. To the bentonite slurry 50 grams of the molybdenum fertilizer (300 mesh) was added and stirred. The slurry was sprayed over the seeds and then dried with an air blower at 40° C. with constant mixing. The product is soybean seed with 0.2 weight percent molybdenum, and 1.4 weight percent phosphorus. When the seeds were placed in water, the fertilizer dispersed immediately. This forms a convenient method of applying the molybdenum fertilizer in the field. It also enriches the DAP with micronutrient.

Example 40

Zinc-Iron-Manganese Fertilizer Mixture with NPK Fertilizer

C. Production of Zinc-Iron-Manganese Fertilizer 10 kilograms of phosphoric acid (58.5% $P_2O_5$) was placed in a glass reactor vessel. To the acid, 360 grams of zinc ash (76.8% Zn) was added with stirring. The reactor was heated using oil heating at 80° C. for 20 min. Then 1.2 kilograms of hematite (46.3% Fe), 560 grams of pyrolusite (49.3% Mn) and 165 grams of magnesia (41.7% Mg) were added and stirred. The suspension was heated with stirring for 200 minutes till the liquid temperature was 135° C. The liquid was removed from the reactor, allowed to cool to room temperature and neutralized with 10 liters ammonia solution (25% $NH_3$). The pH of the product was 5.6. It was then dried in a hot air drier at 80° C., ground in a mortar and sieved through 150 mesh BS sieve.

The product included 2.3 wt % zinc, 4.6 wt % iron, 2.2 wt % manganese, 0.54 wt % magnesium, 14 wt % nitrogen and 22 wt % phosphorus. In 0.33M citric acid the amount of zinc, iron and manganese dissolved was 97 wt %, 95 wt % and 89 wt % respectively of the total zinc, iron and manganese in the fertilizer. In 0.005M DTPA the amount of zinc, iron, manganese dissolved was 89 wt %, 87 wt % and 85 wt % respectively, of the total zinc, iron and manganese in the fertilizer.

D. Mixing with NPK 5 kilograms of urea was taken in a mixer. 500 grams of the zinc-iron-manganese fertilizer of example 40A was added to it. The mixer was rotated for 4 minutes. The zinc-iron-manganese fertilizer adhered to the surface of urea. Then 2 kilograms DAP and 1 kilogram muriate of potash (potassium chloride) were added and the mixing was done for 5 minutes. The micronutrient was distributed uniformly in the mixture and did not sediment to the bottom. Due to electrostatic adhesion of the micronutrient fertilizer on urea surface it is possible to obtain good distribution of micronutrients in a NPK mixture.

C. Coating on DAP

The process described in Example 37 was used except that 1 kilogram of the zinc-iron-manganese fertilizer of the example 40 was added to it. The product contained 0.4 wt % zinc, 0.77 weight percent iron, 0.4 weight percent manganese, 0.09 weight percent magnesium, 18.7 weight percent phosphorus and 17.3 weight percent nitrogen. When the DAP was added to water, the particles dispersed in about 45 minutes. The coating was firm and did not come off when rubbed between the fingers.

What is claimed is:

1. A population of composite particles having an average size of greater than 80 mesh BS, the composite particles comprising a layer of a water-insoluble, dilute acid-soluble inorganic polyphosphate polymer composition overlying a discrete inner layer of a chemically distinct composition, the inorganic polyphosphate polymer composition containing 5 to 70 wt % orthophosphate and having a number average chain length of greater than 2 but less than 50 repeat units comprising phosphate when the orthophosphate content of the polyphosphate polymer is excluded from the average chain length calculation and a number average chain length of at least 1.1 but less than 50 repeat units comprising phosphate when the orthophosphate content of the polyphosphate polymer is included in the average chain length calculation, the chemically distinct composition being a plant seed or a water-soluble macronutrient fertilizer.

2. The population of particles of claim 1 wherein the particles have an average size greater than 2 mm.

3. The population of particles of claim 1, the population comprising about 0.1 to 50 wt. % of the water-insoluble, dilute acid-soluble polyphosphate composition.

4. The population of particles of claim 1, the inorganic polyphosphate composition containing at least 5 wt. % alkali metal, alkaline earth metal, ammonium, or a combination thereof.

5. The population of particles of claim 1, wherein the inorganic polyphosphate composition contains less than 30 wt. % of boron, chromium, cobalt, copper, iodine, iron, manganese, molybdenum, selenium, sulfur and zinc, in combination.

6. The population of particles of claim 1, wherein the inorganic polyphosphate composition contains calcium, magnesium, or a combination thereof, and optionally one or more micronutrients selected from boron, chromium, cobalt, copper, iodine, iron, manganese, molybdenum, selenium, sulfur and zinc, the inorganic polyphosphate having a ratio, A:P, having a value of 0.3:1 to 1:1 wherein A is the combined number of equivalents of calcium and magnesium incorporated in the inorganic polyphosphate composition and P is the number of equivalents of phosphorus, P, incorporated in the inorganic polyphosphate composition.

7. The population of particles of claim 1, the inorganic polyphosphate composition containing at least 5 wt. % calcium, magnesium, sodium, potassium or ammonium, in combination, and optionally, one or more nutrients selected from boron, chromium, cobalt, copper, iodine, iron, manganese, molybdenum, selenium, and zinc, the inorganic polyphosphate composition having a solubility in deionized water at 25° C. such that the combined amount of ammonium, calcium, chromium, cobalt, copper, iron, magnesium, manganese, potassium, selenium, sodium, and zinc that dissolves from the inorganic polyphosphate composition during a 30 minute period in deionized water at 25° C. is less than 20% of the combined amount of ammonium, calcium, chromium, cobalt, copper, iron, magnesium, manganese, potassium, selenium, sodium, and zinc that dissolves from the inorganic polyphosphate composition during a 30 minute period in 0.1 N HCl at 25° C.

8. The population of particles of claim 1, the inorganic polyphosphate composition containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in dilute citric acid at 25° C. such that the combined amount of ammonium, calcium, chromium, cobalt, copper, iron, magnesium, manganese, potassium, selenium, sodium, and zinc that dissolves from the inorganic polyphosphate composition during a 20 minute period in citric acid having a citric acid concentration not in excess of 6.9 wt. % citric acid at 25° C. is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1 N HCl at 25° C.

9. The population of particles claim 1, the inorganic polyphosphate composition containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in dilute citric acid at 25° C. such that the combined amount of ammonium, calcium, chromium, cobalt, copper, iron, magnesium, manganese, potassium, selenium, sodium, and zinc that dissolves from the inorganic polyphosphate composition during a 20 minute period in citric acid having a citric acid concentration not in excess of 2 wt. % citric acid at 25° C. is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1 N HCl at 25° C.

10. The population of particles of claim 1, the inorganic polyphosphate composition containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in dilute diethylenetriaminepentaacetic acid (DTPA) at 25° C. such that the combined amount of ammonium, calcium, chromium, cobalt, copper, iron, magnesium, manganese, potassium, selenium, sodium, and zinc that dissolves from the inorganic polyphosphate composition during a 20 minute period in 0.005M DTPA at 25° C. is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1 N HCl at 25° C.

11. The population of particles of claim 1, wherein the particles comprise an inorganic polyphosphate composition in solid form characterized by having an X-ray diffraction reflection at one or more of the following positions: 7.54 (±0.03), 6.74(±0.03), 5.96 (±0.03), 5.37 (±0.03), 5.01 (±0.025), 4.73, 4.61, 4.5, 4.15, 4.04, 3.7, 3.66(±0.01), 3.58 (±0.01), 3.47(±0.01), 3.39(±0.01), 3.35(±0.01), 3.19(±0.01), 3.13(±0.01), 3.09(±0.01), 3.05(±0.01), 2.96(±0.009), 2.94(±0.009), 2.82(±0.009), 2.76(±0.008), 2.73(±0.008), 2.59(±0.007), 2.53(±0.007), 2.5(±0.007), 2.43(±0.007), 2.41 (±0.007), 2.37(±0.007), 2.34(±0.006), 2.25(±0.006), 2.2(±0.006), 2.18(±0.005), 2.16(±0.005), 2.14(±0.005), 2.12 (±0.005), 2.09(±0.005), 2.08(±0.005), 2.03(±0.005), 1.99(±0.004), 1.93(±0.004), 1.91(±0.004), 1.85(±0.003), 1.8 (±0.003), 1.76(±0.003), 1.72(±0.003), 1.68(±0.0028), 1.64 (±0.0027), 1.59(±0.0025), 1.57(±0.0024) Å.

12. The population of particles of claim 1, wherein the inorganic polyphosphate composition comprises one or more micronutrient metal(s) selected from the group consisting of chromium, cobalt, copper, iron, manganese, zinc and combinations thereof with the ratio of the combined number of equivalents of the micronutrient metal(s), M, to the number of equivalents of phosphorus, P, in the micronutrient metal polyphosphate composition having a value of M:P wherein M:P is less than 0.4:1.

13. The population of particles of claim 1, wherein the repeat units comprise phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1 and wherein the water-insoluble, dilute acid-soluble inorganic polyphosphate composition has a ratio, M:Z, that is less than 0.4:1 wherein M is the combined number of equivalents of the micronutrient metal(s) in the water-insoluble, dilute acid-soluble inorganic polyphosphate composition and Z is the combined number of equivalents of phosphorus, sulfur, boron, molybdenum and selenium incorporated into the phosphate, sulfate, borate, molybdate or selenate repeat units.

14. The population of particles of claim 1, wherein the inorganic polyphosphate composition contains at least 0.01 wt. % of one or more of boron, chromium, cobalt, copper, iodine, iron, manganese, molybdenum, selenium, sulfur and zinc, the population of particles being a free-flowing powder or granule having a moisture content of less than 10%.

15. The population of particles of claim 1, wherein the inorganic polyphosphate has a number average chain length of between 2 and 15 phosphate units based upon the non-orthophosphate fraction of the polyphosphate.

16. The population of particles of claim 15, wherein the inorganic polyphosphate has a ratio, A:P, having a value of 0.3:1 to 1:1 wherein A is the combined number of equivalents of calcium and magnesium incorporated in the inorganic polyphosphate composition and P is the number of equivalents of phosphorus, P, incorporated in the inorganic polyphosphate composition.

17. The population of particles of claim 1, wherein the inorganic polyphosphate composition contains at least 7 wt. % but not more than 35 wt. % of calcium and magnesium, in combination.

18. The population of particles of claim 1, wherein the inorganic polyphosphate composition contains less than 5 wt. % of boron, chromium, cobalt, copper, iodine, iron, manganese, molybdenum, selenium and zinc, in combination.

19. The population of particles of claim 1, wherein the inorganic polyphosphate composition contains more than 5 wt. % of boron, chromium, cobalt, copper, iodine, iron, manganese, molybdenum, selenium and zinc, in combination.

20. The population of particles of claim 1 wherein the inorganic polyphosphate composition contains calcium and magnesium with atomic ratio of calcium to magnesium being at least 0.2:1 (calcium:magnesium).

21. A composite particle having a size greater than 0.2 mm, the composite particle comprising a water-insoluble, dilute acid-soluble inorganic polyphosphate polymer composition in solid form and a chemically distinct composition, the inorganic polyphosphate polymer composition and the chemically distinct composition being present in discontinuous regions of discrete composition in the particle, the inorganic polyphosphate polymer composition containing 5 to 70 wt % orthophosphate, and optionally one or more micronutrient metals selected from the group consisting of chromium, cobalt, copper, iron, manganese, and zinc, the inorganic polyphosphate polymer has a number average chain length of greater than 2 and less than 50 repeat units when the orthophosphate content of the inorganic polyphosphate polymer is excluded from the average chain length calculation and a number average chain length of at least 1.1 but less than 50 repeat units when the orthophosphate content of the inorganic polyphosphate polymer is included in the average chain length calculation, the repeat units comprising phosphate, sulfate, borate, molybdate, or selenate units, or a combination thereof, provided the ratio of phosphate units to the combined total of sulfate, borate, molybdate and selenate repeat units comprised by the inorganic polyphosphate composition is at least 2:1, the chemically distinct composition being a pesticide, agrichemical, macronutrient fertilizer or a plant seed.

22. The composite particle of claim 21 wherein composite particle comprises an inner layer or core of dilute acid-soluble inorganic polyphosphate composition, and an outer layer of the chemically distinct composition.

23. The composite particle of claim 21 wherein composite particle comprises an inner layer or core of the chemically distinct composition and an outer layer of the dilute acid-soluble inorganic polyphosphate composition.

24. The composite particle of claim 21, wherein the chemically distinct composition is monoammonium phosphate, diammonium phosphate, triple super phosphate, or urea.

25. The composite particle of claim 21, wherein the chemically distinct composition is a nitrogen-source, a phosphorus source, or a potassium source.

26. The composite particle of claim 21, wherein the composite particle comprises 0.5 to 20 wt % of the water-insoluble, dilute acid-soluble polyphosphate composition.

27. A population of particles comprising a composite particle of claim 21.

28. A fertilizer comprising the population of particles or a composite particle of claim 21.

29. The method of fertilizing plants or soil, the method comprising applying a fertilizer composition comprising a population of particles or a composite particle of claim 21 to the soil.

30. The population of particles of claim 1 wherein the chemically distinct composition is a macronutrient fertilizer comprising a nitrogen source selected from the group consisting of urea, ammonium sulfate and derivatives thereof.

31. The population of particles of claim 1 wherein the chemically distinct composition is a macronutrient fertilizer comprising a phosphorus source selected from the group consisting of superphosphate, triple superphosphate, calcium phosphate, nitrophosphate, potassium phosphate, ammonium phosphate, ammoniated superphosphate and mixtures thereof.

32. The population of particles of claim 1 wherein the chemically distinct composition is a macronutrient fertilizer comprising a potassium source selected from the group consisting of muriate of potash, potassium sulfate, potassium phosphate, potassium hydroxide, potassium nitrate, potassium carbonate and bicarbonate, potassium magnesium sulfate and mixtures thereof.

33. The population of particles of claim 1 wherein the chemically distinct composition is a plant seed.

34. The population of particles of claim 1 wherein the chemically distinct composition is a plant seed selected from the group consisting of soybean, corn, rice and wheat seeds.

35. The population of particles of claim 9 wherein the chemically distinct composition is a macronutrient fertilizer comprising a nitrogen source selected from the group consisting of urea, ammonium sulfate and derivatives thereof.

36. The population of particles of claim 9 wherein the chemically distinct composition is a macronutrient fertilizer comprising a phosphorus source selected from the group consisting of superphosphate, triple superphosphate, calcium phosphate, nitrophosphate, potassium phosphate, ammonium phosphate, ammoniated superphosphate and mixtures thereof.

37. The population of particles of claim 9 wherein the chemically distinct composition is a macronutrient fertilizer comprising a potassium source selected from the group consisting of muriate of potash, potassium sulfate, potassium phosphate, potassium hydroxide, potassium nitrate, potassium carbonate and bicarbonate, potassium magnesium sulfate and mixtures thereof.

38. The population of particles of claim 9 wherein the chemically distinct composition is a plant seed.

39. The population of particles of claim 9 wherein the chemically distinct composition is a plant seed selected from the group consisting of soybean, corn, rice and wheat seeds.

40. The composite particle of claim 21, the inorganic polyphosphate composition containing at least 5 wt. % of calcium, magnesium, sodium, potassium or ammonium, in combination, and optionally, one or more nutrients selected from boron, chromium, cobalt, copper, iodine, iron, manganese, molybdenum, selenium and zinc, the inorganic polyphosphate composition having a solubility in dilute citric acid at 25° C. such that the combined amount of ammonium, calcium, chromium, cobalt, copper, iron, magnesium, manganese, potassium, selenium, sodium, and zinc that dissolves from the inorganic polyphosphate composition during a 20 minute period in citric acid having a citric acid concentration not in excess of 2 wt. % citric acid at 25° C. is at least 75% of the combined amount of ammonium, calcium, chromium, cobalt, copper, iron, magnesium, manganese, potassium, selenium, sodium, and zinc that dissolves from the inorganic polyphosphate composition during a 20 minute period in 0.1 N HCl at 25° C.

41. The composite particle of claim 40 wherein the chemically distinct composition is a macronutrient fertilizer comprising a nitrogen source selected from the group consisting of urea, ammonium sulfate and derivatives thereof.

42. The composite particle of claim 40 wherein the chemically distinct composition is a macronutrient fertilizer comprising a phosphorus source selected from the group consisting of superphosphate, triple superphosphate, calcium phosphate, nitrophosphate, potassium phosphate, ammonium phosphate, ammoniated superphosphate and mixtures thereof.

43. The composite particle of claim 40 wherein the chemically distinct composition is a macronutrient fertilizer comprising a potassium source selected from the group consisting of muriate of potash, potassium sulfate, potassium phosphate, potassium hydroxide, potassium nitrate, potassium carbonate and bicarbonate, potassium magnesium sulfate and mixtures thereof.

44. The composite particle of claim 40 wherein the chemically distinct composition is a plant seed.

45. The composite particle of claim 40 wherein the chemically distinct composition is a plant seed selected from the group consisting of soybean, corn, rice and wheat seeds.

46. The composite particle of claim 40 wherein the chemically distinct composition is a macronutrient fertilizer comprising a nitrogen source selected from the group consisting of urea, ammonium sulfate and derivatives thereof.

47. The composite particle of claim 40 wherein the chemically distinct composition is a macronutrient fertilizer comprising a phosphorus source selected from the group consisting of superphosphate, triple superphosphate, calcium phosphate, nitrophosphate, potassium phosphate, ammonium phosphate, ammoniated superphosphate and mixtures thereof.

48. The composite particle of claim 40 wherein the chemically distinct composition is a potassium source selected from the group consisting of muriate of potash, potassium sulfate, potassium phosphate, potassium hydroxide, potassium nitrate, potassium carbonate and bicarbonate, potassium magnesium sulfate and mixtures thereof.

49. The composite particle of claim 40 wherein the chemically distinct composition is a plant seed.

50. The composite particle of claim 40 wherein the chemically distinct composition is a plant seed selected from the group consisting of soybean, corn, rice and wheat seeds.

* * * * *